US007491397B2

(12) United States Patent
Chong et al.

(10) Patent No.: US 7,491,397 B2

(45) Date of Patent: Feb. 17, 2009

(54) RECEPTOR BINDING POLYPEPTIDES

(75) Inventors: Pele Choi Sing Chong, Richmond Hill (CA); Shie-Liang Hsieh, Taipei (TW)

(73) Assignee: National Health Research Institutes, Miaoli County (TW)

( * ) Notice: Subject to any disclaimer, the term of this patent is extended or adjusted under 35 U.S.C. 154(b) by 380 days.

(21) Appl. No.: 11/033,455

(22) Filed: Jan. 10, 2005

(65) Prior Publication Data

US 2008/0213284 A1 Sep. 4, 2008

Related U.S. Application Data

(60) Provisional application No. 60/535,641, filed on Jan. 9, 2004.

(51) Int. Cl.

| | |
|---|---|
| ***A61K 39/12*** | (2006.01) |
| ***A61K 39/00*** | (2006.01) |
| ***A61K 39/38*** | (2006.01) |
| ***A61K 39/295*** | (2006.01) |
| ***A61K 38/00*** | (2006.01) |
| ***C07K 1/00*** | (2006.01) |
| ***C07K 14/00*** | (2006.01) |
| ***C07K 17/00*** | (2006.01) |

(52) U.S. Cl. .............. 424/186.1; 424/184.1; 424/185.1; 424/192.1; 424/202.1; 530/300; 530/350

(58) Field of Classification Search ....................... None
See application file for complete search history.

(56) References Cited

U.S. PATENT DOCUMENTS

2006/0257852 A1* 11/2006 Rappuoli et al. ............... 435/5

OTHER PUBLICATIONS

Li et al. Angiotensin-converting enzyme 2 is a functional receptor for the SARS coronavirus. Nature Nov. 27, 2003, vol. 426, p. 450-454.*

Test et al. Increased immunogenicity and induction of class switching by conjugation of complement C3d to pneumococcal serotype 14 capsular polysaccharide. Infection and Immunity, May 2001, vol. 69, No. 5, p. 3031-3040.*

Watanabe et al. Protection against influenza virus infection by intranasal administration of C3d-fused hemagglutinin. Vaccine Nov. 7, 2003, vol. 21(31), p. 4532-4538.*

Shortridge. SARS exposed, pandemic influenza lurks. The Lancet, May 10, 2003, vol. 361, p. 1649.*

Godeke et al., "Assembly of Spikes into Coronavirus Particles is Mediated by the Carboxy-Terminal Domain of the Spike Protein," Journal of Virology, 74(3):1566-1571 (2000).

Kuo et al., "Retargeting of Coronavirus by Substitution of the Spike Glycoprotein Ectodomain: Crossing the Host Cell Species Barrier," Journal of Virology, 74(3):1393-1406 (2000).

* cited by examiner

*Primary Examiner*—Bruce Campell
*Assistant Examiner*—Louise Humphrey
(74) *Attorney, Agent, or Firm*—Occhiuti Rohlicek & Tsao LLP

(57) ABSTRACT

Isolated polypeptides containing fragments of SARS CoV S protein and functional equivalents thereof. Also disclosed are isolated nucleic acids encoding the polypeptides, related expression vectors, related host cells, related antibodies, and related compositions. Methods of producing the polypeptide, diagnosing infection with a coronavirus, and identifying a test compound for treating infection with a coronavirus are also disclosed.

13 Claims, No Drawings

SEQUENCE LISTING

```
<160> NUMBER OF SEQ ID NOS: 214

<210> SEQ ID NO 1
<211> LENGTH: 29727
<212> TYPE: DNA
<213> ORGANISM: SARS coronavirus Urbani

<400> SEQUENCE: 1

atattaggtt tttacctacc caggaaaagc caaccaacct cgatctcttg tagatctgtt      60

ctctaaacga actttaaaat ctgtgtagct gtcgctcggc tgcatgccta gtgcacctac     120

gcagtataaa caataataaa ttttactgtc gttgacaaga aacgagtaac tcgtccctct     180

tctgcagact gcttacggtt tcgtccgtgt tgcagtcgat catcagcata cctaggtttc     240

gtccgggtgt gaccgaaagg taagatggag agccttgttc ttggtgtcaa cgagaaaaca     300

cacgtccaac tcagtttgcc tgtccttcag gttagagacg tgctagtgcg tggcttcggg     360

gactctgtgg aagaggccct atcggaggca cgtgaacacc tcaaaaatgg cacttgtggt     420

ctagtagagc tggaaaaagg cgtactgccc cagcttgaac agccctatgt gttcattaaa     480

cgttctgatg ccttaagcac caatcacggc cacaaggtcg ttgagctggt tgcagaaatg     540

gacggcattc agtacggtcg tagcggtata acactgggag tactcgtgcc acatgtgggc     600

gaaaccccaa ttgcataccg caatgttctt cttcgtaaga acggtaataa gggagccggt     660
```

-continued

```
ggtcatagct atggcatcga tctaaagtct tatgacttag gtgacgagct tggcactgat    720
cccattgaag attatgaaca aaactggaac actaagcatg gcagtggtgc actccgtgaa    780
ctcactcgtg agctcaatgg aggtgcagtc actcgctatg tcgacaacaa tttctgtggc    840
ccagatgggt accctcttga ttgcatcaaa gattttctcg cacgcgcggg caagtcaatg    900
tgcactcttt ccgaacaact tgattacatc gagtcgaaga gaggtgtcta ctgctgccgt    960
gaccatgagc atgaaattgc ctggttcact gagcgctctg ataagagcta cgagcaccag   1020
acacccttcg aaattaagag tgccaagaaa tttgacactt tcaaagggga atgcccaaag   1080
tttgtgtttc ctcttaactc aaaagtcaaa gtcattcaac cacgtgttga aaagaaaaag   1140
actgagggtt tcatggggcg tatacgctct gtgtaccctg ttgcatctcc acaggagtgt   1200
aacaatatgc acttgtctac cttgatgaaa tgtaatcatt gcgatgaagt ttcatggcag   1260
acgtgcgact ttctgaaagc cacttgtgaa cattgtggca ctgaaaattt agttattgaa   1320
ggacctacta catgtgggta cctacctact aatgctgtag tgaaaatgcc atgtcctgcc   1380
tgtcaagacc cagagattgg acctgagcat agtgttgcag attatcacaa ccactcaaac   1440
attgaaactc gactccgcaa gggaggtagg actagatgtt ttggaggctg tgtgtttgcc   1500
tatgttggct gctataataa gcgtgcctac tgggttcctc gtgctagtgc tgatattggc   1560
tcaggccata ctggcattac tggtgacaat gtggagacct tgaatgagga tctccttgag   1620
atactgagtc gtgaacgtgt taacattaac attgttggcg attttcattt gaatgaagag   1680
gttgccatca ttttggcatc tttctctgct tctacaagtg cctttattga cactataaag   1740
agtcttgatt acaagtcttt caaaaccatt gttgagtcct gcggtaacta taaagttacc   1800
aagggaaagc ccgtaaaagg tgcttggaac attggacaac agagatcagt tttaacacca   1860
ctgtgtggtt ttccctcaca ggctgctggt gttatcagat caatttttgc gcgcacactt   1920
gatgcagcaa accactcaat tcctgatttg caaagagcag ctgtcaccat acttgatggt   1980
atttctgaac agtcattacg tcttgtcgac gccatggttt atacttcaga cctgctcacc   2040
aacagtgtca ttattatggc atatgtaact ggtggtcttg tacaacagac ttctcagtgg   2100
ttgtctaatc ttttgggcac tactgttgaa aaactcaggc ctatctttga atggattgag   2160
gcgaaactta gtgcaggagt tgaatttctc aaggatgctt gggagattct caaatttctc   2220
attacaggtg tttttgacat cgtcaagggt caaatacagg ttgcttcaga taacatcaag   2280
gattgtgtaa aatgcttcat tgatgttgtt aacaaggcac tcgaaatgtg cattgatcaa   2340
gtcactatcg ctggcgcaaa gttgcgatca ctcaacttag gtgaagtctt catcgctcaa   2400
agcaagggac tttaccgtca gtgtatacgt ggcaaggagc agctgcaact actcatgcct   2460
cttaaggcac caaaagaagt aacctttctt gaaggtgatt cacatgacac agtacttacc   2520
tctgaggagg ttgttctcaa gaacggtgaa ctcgaagcac tcgagacgcc cgttgatagc   2580
ttcacaaatg gagctatcgt tggcacacca gtctgtgtaa atggcctcat gctcttagag   2640
attaaggaca aagaacaata ctgcgcattg tctcctggtt tactggctac aaacaatgtc   2700
tttcgcttaa aaggggggtgc accaattaaa ggtgtaacct ttggagaaga tactgtttgg   2760
gaagttcaag gttacaagaa tgtgagaatc acatttgagc ttgatgaacg tgttgacaaa   2820
gtgcttaatg aaaagtgctc tgtctacact gttgaatccg gtaccgaagt tactgagttt   2880
gcatgtgttg tagcagaggc tgttgtgaag actttacaac cagtttctga tctccttacc   2940
aacatgggta ttgatcttga tgagtggagt gtagctacat tctacttatt tgatgatgct   3000
ggtgaagaaa acttttcatc acgtatgtat tgttcctttt accctccaga tgaggaagaa   3060
```

-continued

```
gaggacgatg cagagtgtga ggaagaagaa attgatgaaa cctgtgaaca tgagtacggt   3120
acagaggatg attatcaagg tctccctctg gaatttggtg cctcagctga aacagttcga   3180
gttgaggaag aagaagagga agactggctg gatgatacta ctgagcaatc agagattgag   3240
ccagaaccag aacctacacc tgaagaacca gttaatcagt ttactggtta tttaaaactt   3300
actgacaatg ttgccattaa atgtgttgac atcgttaagg aggcacaaag tgctaatcct   3360
atggtgattg taaatgctgc taacatacac ctgaaacatg gtggtggtgt agcaggtgca   3420
ctcaacaagg caaccaatgg tgccatgcaa aaggagagtg atgattacat taagctaaat   3480
ggccctctta cagtaggagg gtcttgtttg ctttctggac ataatcttgc taagaagtgt   3540
ctgcatgttg ttggacctaa cctaaatgca ggtgaggaca tccagcttct taaggcagca   3600
tatgaaaatt tcaattcaca ggacatctta cttgcaccat tgttgtcagc aggcatattt   3660
ggtgctaaac cacttcagtc tttacaagtg tgcgtgcaga cggttcgtac acaggtttat   3720
attgcagtca atgacaaagc tctttatgag caggttgtca tggattatct tgataacctg   3780
aagcctagag tggaagcacc taaacaagag gagccaccaa acacagaaga ttccaaaact   3840
gaggagaaat ctgtcgtaca gaagcctgtc gatgtgaagc caaaaattaa ggcctgcatt   3900
gatgaggtta ccacaacact ggaagaaact aagtttctta ccaataagtt actcttgttt   3960
gctgatatca atggtaagct ttaccatgat tctcagaaca tgcttagagg tgaagatatg   4020
tctttccttg agaaggatgc accttacatg gtaggtgatg ttatcactag tggtgatatc   4080
acttgtgttg taataccctc caaaaaggct ggtggcacta ctgagatgct ctcaagagct   4140
ttgaagaaag tgccagttga tgagtatata accacgtacc ctggacaagg atgtgctggt   4200
tatacacttg aggaagctaa gactgctctt aagaaatgca aatctgcatt ttatgtacta   4260
ccttcagaag cacctaatgc taaggaagag attctaggaa ctgtatcctg gaatttgaga   4320
gaaatgcttg ctcatgctga agagacaaga aaattaatgc ctatatgcat ggatgttaga   4380
gccataatgg caaccatcca acgtaagtat aaaggaatta aaattcaaga gggcatcgtt   4440
gactatggtg tccgattctt cttttatact agtaaagagc ctgtagcttc tattattacg   4500
aagctgaact ctctaaatga gccgcttgtc acaatgccaa ttggttatgt gacacatggt   4560
tttaatcttg aagaggctgc gcgctgtatg cgttctctta aagctcctgc cgtagtgtca   4620
gtatcatcac cagatgctgt tactacatat aatggatacc tcacttcgtc atcaaagaca   4680
tctgaggagc actttgtaga aacagtttct ttggctggct cttacagaga ttggtcctat   4740
tcaggacagc gtacagagtt aggtgttgaa tttcttaagc gtggtgacaa aattgtgtac   4800
cacactctgg agagccccgt cgagtttcat cttgacggtg aggttctttc acttgacaaa   4860
ctaaagagtc tcttatccct gcgggaggtt aagactataa aagtgttcac aactgtggac   4920
aacactaatc tccacacaca gcttgtggat atgtctatga catatggaca gcagtttggt   4980
ccaacatact tggatggtgc tgatgttaca aaaattaaac ctcatgtaaa tcatgagggt   5040
aagactttct ttgtactacc tagtgatgac acactacgta gtgaagcttt cgagtactac   5100
catactcttg atgagagttt tcttggtagg tacatgtctg ctttaaacca cacaaagaaa   5160
tggaaatttc ctcaagttgg tggtttaact tcaattaaat gggctgataa caattgttat   5220
ttgtctagtg ttttattagc acttcaacag cttgaagtca aattcaatgc accagcactt   5280
caagaggctt attatagagc ccgtgctggt gatgctgcta acttttgtgc actcatactc   5340
gcttacagta ataaaactgt tggcgagctt ggtgatgtca gagaaactat gacccatctt   5400
```

-continued

```
ctacagcatg ctaatttgga atctgcaaag cgagttctta atgtggtgtg taaacattgt   5460
ggtcagaaaa ctactacctt aacgggtgta gaagctgtga tgtatatggg tactctatct   5520
tatgataatc ttaagacagg tgtttccatt ccatgtgtgt gtggtcgtga tgctacacaa   5580
tatctagtac aacaagagtc ttcttttgtt atgatgtctg caccacctgc tgagtataaa   5640
ttacagcaag gtacattctt atgtgcgaat gagtacactg gtaactatca gtgtggtcat   5700
tacactcata taactgctaa ggagaccctc tatcgtattg acggagctca ccttacaaag   5760
atgtcagagt acaaaggacc agtgactgat gttttctaca aggaaacatc ttacactaca   5820
accatcaagc ctgtgtcgta taaactcgat ggagttactt acacagagat tgaaccaaaa   5880
ttggatgggt attataaaaa ggataatgct tactatacag agcagcctat agaccttgta   5940
ccaactcaac cattaccaaa tgcgagtttt gataatttca aactcacatg ttctaacaca   6000
aaatttgctg atgatttaaa tcaaatgaca ggcttcacaa agccagcttc acgagagcta   6060
tctgtcacat tcttcccaga cttgaatggc gatgtagtgg ctattgacta tagacactat   6120
tcagcgagtt tcaagaaagg tgctaaatta ctgcataagc caattgtttg gcacattaac   6180
caggctacaa ccaagacaac gttcaaacca aacacttggt gtttacgttg tctttggagt   6240
acaaagccag tagatacttc aaattcattt gaagttctgg cagtagaaga cacacaagga   6300
atggacaatc ttgcttgtga aagtcaacaa cccacctctg aagaagtagt ggaaaatcct   6360
accatacaga aggaagtcat agagtgtgac gtgaaaacta ccgaagttgt aggcaatgtc   6420
atacttaaac catcagatga aggtgttaaa gtaacacaag agttaggtca tgaggatctt   6480
atggctgctt atgtggaaaa cacaagcatt accattaaga aacctaatga gctttcacta   6540
gccttaggtt taaaaacaat tgccactcat ggtattgctg caattaatag tgttccttgg   6600
agtaaaattt tggcttatgt caaaccattc ttaggacaag cagcaattac aacatcaaat   6660
tgcgctaaga gattagcaca acgtgtgttt aacaattata tgccttatgt gtttacatta   6720
ttgttccaat tgtgtacttt tactaaaagt accaattcta gaattagagc ttcactacct   6780
acaactattg ctaaaaatag tgttaagagt gttgctaaat tatgtttgga tgccggcatt   6840
aattatgtga agtcacccaa attttctaaa ttgttcacaa tcgctatgtg gctattgttg   6900
ttaagtattt gcttaggttc tctaatctgt gtaactgctg cttttggtgt actcttatct   6960
aattttggtg ctccttctta ttgtaatggc gttagagaat tgtatcttaa ttcgtctaac   7020
gttactacta tggatttctg tgaaggttct tttccttgca gcatttgttt aagtggatta   7080
gactcccttg attcttatcc agctcttgaa accattcagg tgacgatttc atcgtacaag   7140
ctagacttga caattttagg tctggccgct gagtgggttt tggcatatat gttgttcaca   7200
aaattctttt atttattagg tctttcagct ataatgcagg tgttctttgg ctattttgct   7260
agtcatttca tcagcaattc ttggctcatg tggtttatca ttagtattgt acaaatggca   7320
cccgtttctg caatggttag gatgtacatc ttctttgctt ctttctacta catatggaag   7380
agctatgttc atatcatgga tggttgcacc tcttcgactt gcatgatgtg ctataagcgc   7440
aatcgtgcca cacgcgttga gtgtacaact attgttaatg gcatgaagag atctttctat   7500
gtctatgcaa atggaggccg tggcttctgc aagactcaca attggaattg tctcaattgt   7560
gacacatttt gcactggtag tacattcatt agtgatgaag ttgctcgtga tttgtcactc   7620
cagtttaaaa gaccaatcaa ccctactgac cagtcatcgt atattgttga tagtgttgct   7680
gtgaaaaatg gcgcgcttca cctctacttt gacaaggctg gtcaaaagac ctatgagaga   7740
catccgctct cccattttgt caatttagac aatttgagag ctaacaacac taaaggttca   7800
```

-continued

```
ctgcctatta atgtcatagt ttttgatggc aagtccaaat gcgacgagtc tgcttctaag   7860
tctgcttctg tgtactacag tcagctgatg tgccaaccta ttctgttgct tgaccaagtt   7920
cttgtatcag acgttggaga tagtactgaa gtttccgtta agatgtttga tgcttatgtc   7980
gacacctttt cagcaacttt tagtgttcct atggaaaaac ttaaggcact tgttgctaca   8040
gctcacagcg agttagcaaa gggtgtagct ttagatggtg tcctttctac attcgtgtca   8100
gctgcccgac aaggtgttgt tgataccgat gttgacacaa aggatgttat tgaatgtctc   8160
aaactttcac atcactctga cttagaagtg acaggtgaca gttgtaacaa tttcatgctc   8220
acctataata aggttgaaaa catgacgccc agagatcttg gcgcatgtat tgactgtaat   8280
gcaaggcata tcaatgccca agtagcaaaa agtcacaatg tttcactcat ctggaatgta   8340
aaagactaca tgtctttatc tgaacagctg cgtaaacaaa ttcgtagtgc tgccaagaag   8400
aacaacatac cttttagact aacttgtgct acaactagac aggttgtcaa tgtcataact   8460
actaaaatct cactcaaggg tggtaagatt gttagtactt gttttaaact tatgcttaag   8520
gccacattat tgtgcgttct tgctgcattg gtttgttata tcgttatgcc agtacataca   8580
ttgtcaatcc atgatggtta cacaaatgaa atcattggtt acaaagccat tcaggatggt   8640
gtcactcgtg acatcatttc tactgatgat tgttttgcaa ataaacatgc tggttttgac   8700
gcatggttta gccagcgtgg tggttcatac aaaaatgaca aaagctgccc tgtagtagct   8760
gctatcatta caagagagat tggtttcata gtgcctggct taccgggtac tgtgctgaga   8820
gcaatcaatg gtgacttctt gcattttcta cctcgtgttt ttagtgctgt tggcaacatt   8880
tgctacacac cttccaaact cattgagtat agtgattttg ctacctctgc ttgcgttctt   8940
gctgctgagt gtacaatttt taaggatgct atgggcaaac ctgtgccata ttgttatgac   9000
actaatttgc tagagggttc tatttcttat agtgagcttc gtccagacac tcgttatgtg   9060
cttatggatg gttccatcat acagtttcct aacacttacc tggagggttc tgttagagta   9120
gtaacaactt ttgatgctga gtactgtaga catggtacat gcgaaaggtc agaagtaggt   9180
atttgcctat ctaccagtgg tagatgggtt cttaataatg agcattacag agctctatca   9240
ggagttttct gtggtgttga tgcgatgaat ctcatagcta acatctttac tcctcttgtg   9300
caacctgtgg gtgctttaga tgtgtctgct tcagtagtgg ctggtggtat tattgccata   9360
ttggtgactt gtgctgccta ctactttatg aaattcagac gtgtttttgg tgagtacaac   9420
catgttgttg ctgctaatgc acttttgttt ttgatgtctt tcactatact ctgtctggta   9480
ccagcttaca gctttctgcc gggagtctac tcagtctttt acttgtactt gacattctat   9540
ttcaccaatg atgtttcatt cttggctcac cttcaatggt ttgccatgtt ttctcctatt   9600
gtgccttttt ggataacagc aatctatgta ttctgtattt ctctgaagca ctgccattgg   9660
ttctttaaca actatcttag gaaaagagtc atgtttaatg gagttacatt tagtaccttc   9720
gaggaggctg ctttgtgtac ctttttgctc aacaaggaaa tgtacctaaa attgcgtagc   9780
gagacactgt tgccacttac acagtataac aggtatcttg ctctatataa caagtacaag   9840
tatttcagtg gagccttaga tactaccagc tatcgtgaag cagcttgctg ccacttagca   9900
aaggctctaa atgactttag caactcaggt gctgatgttc tctaccaacc accacagaca   9960
tcaatcactt ctgctgttct gcagagtggt tttaggaaaa tggcattccc gtcaggcaaa  10020
gttgaagggt gcatggtaca agtaacctgt ggaactacaa ctcttaatgg attgtggttg  10080
gatgacacag tatactgtcc aagacatgtc atttgcacag cagaagacat gcttaatcct  10140
```

-continued

```
aactatgaag atctgctcat tcgcaaatcc aaccatagct ttcttgttca ggctggcaat  10200
gttcaacttc gtgttattgg ccattctatg caaaattgtc tgcttaggct taaagttgat  10260
acttctaacc ctaagacacc caagtataaa tttgtccgta tccaacctgg tcaaacattt  10320
tcagttctag catgctacaa tggttcacca tctggtgttt atcagtgtgc catgagacct  10380
aatcatacca ttaaaggttc tttccttaat ggatcatgtg gtagtgttgg ttttaacatt  10440
gattatgatt gcgtgtcttt ctgctatatg catcatatgg agcttccaac aggagtacac  10500
gctggtactg acttagaagg taaattctat ggtccatttg ttgacagaca aactgcacag  10560
gctgcaggta cagacacaac cataacatta aatgttttgg catggctgta tgctgctgtt  10620
atcaatggtg ataggtggtt tcttaataga ttcaccacta ctttgaatga ctttaacctt  10680
gtggcaatga agtacaacta tgaacctttg acacaagatc atgttgacat attgggacct  10740
ctttctgctc aaacaggaat tgccgtctta gatatgtgtg ctgctttgaa agagctgctg  10800
cagaatggta tgaatggtcg tactatcctt ggtagcacta ttttagaaga tgagtttaca  10860
ccatttgatg ttgttagaca atgctctggt gttaccttcc aaggtaagtt caagaaaatt  10920
gttaagggca ctcatcattg gatgctttta actttcttga catcactatt gattcttgtt  10980
caaagtacac agtggtcact gtttttcttt gtttacgaga atgctttctt gccatttact  11040
cttggtatta tggcaattgc tgcatgtgct atgctgcttg ttaagcataa gcacgcattc  11100
ttgtgcttgt ttctgttacc ttctcttgca acagttgctt actttaatat ggtctacatg  11160
cctgctagct gggtgatgcg tatcatgaca tggcttgaat tggctgacac tagcttgtct  11220
ggttataggc ttaaggattg tgttatgtat gcttcagctt tagttttgct tattctcatg  11280
acagctcgca ctgtttatga tgatgctgct agacgtgttt ggacactgat gaatgtcatt  11340
acacttgttt acaaagtcta ctatggtaat gctttagatc aagctatttc catgtgggcc  11400
ttagttattt ctgtaacctc taactattct ggtgtcgtta cgactatcat gtttttagct  11460
agagctatag tgtttgtgtg tgttgagtat tacccattgt tatttattac tggcaacacc  11520
ttacagtgta tcatgcttgt ttattgtttc ttaggctatt gttgctgctg ctactttggc  11580
cttttctgtt tactcaaccg ttacttcagg cttactcttg gtgtttatga ctacttggtc  11640
tctacacaag aatttaggta tatgaactcc caggggcttt tgcctcctaa gagtagtatt  11700
gatgctttca agcttaacat taagttgttg ggtattggag gtaaaccatg tatcaaggtt  11760
gctactgtac agtctaaaat gtctgacgta aagtgcacat ctgtggtact gctctcggtt  11820
cttcaacaac ttagagtaga gtcatcttct aaattgtggg cacaatgtgt acaactccac  11880
aatgatattc ttcttgcaaa agacacaact gaagctttcg agaagatggt ttctcttttg  11940
tctgttttgc tatccatgca gggtgctgta gacattaata ggttgtgcga ggaaatgctc  12000
gataaccgtg ctactcttca ggctattgct tcagaattta gttctttacc atcatatgcc  12060
gcttatgcca ctgcccagga ggcctatgag caggctgtag ctaatggtga ttctgaagtc  12120
gttctcaaaa agttaaagaa atctttgaat gtggctaaat ctgagtttga ccgtgatgct  12180
gccatgcaac gcaagttgga aaagatggca gatcaggcta tgacccaaat gtacaaacag  12240
gcaagatctg aggacaagag ggcaaaagta actagtgcta tgcaaacaat gctcttcact  12300
atgcttagga agcttgataa tgatgcactt aacaacatta tcaacaatgc gcgtgatggt  12360
tgtgttccac tcaacatcat accattgact acagcagcca aactcatggt tgttgtccct  12420
gattatggta cctacaagaa cacttgtgat ggtaacacct ttacatatgc atctgcactc  12480
tgggaaatcc agcaagttgt tgatgcggat agcaagattg ttcaacttag tgaaattaac  12540
```

-continued

```
atggacaatt caccaaattt ggcttggcct cttattgtta cagctctaag agccaactca  12600
gctgttaaac tacagaataa tgaactgagt ccagtagcac tacgacagat gtcctgtgcg  12660
gctggtacca cacaaacagc ttgtactgat gacaatgcac ttgcctacta taacaattcg  12720
aagggaggta ggtttgtgct ggcattacta tcagaccacc aagatctcaa atgggctaga  12780
ttccctaaga gtgatggtac aggtacaatt tacacagaac tggaaccacc ttgtaggttt  12840
gttacagaca caccaaaagg gcctaaagtg aaatacttgt acttcatcaa aggcttaaac  12900
aacctaaata gaggtatggt gctgggcagt ttagctgcta cagtacgtct tcaggctgga  12960
aatgctacag aagtacctgc caattcaact gtgctttcct tctgtgcttt tgcagtagac  13020
cctgctaaag catataagga ttacctagca agtggaggac aaccaatcac caactgtgtg  13080
aagatgttgt gtacacacac tggtacagga caggcaatta ctgtaacacc agaagctaac  13140
atggaccaag agtcctttgg tggtgcttca tgttgtctgt attgtagatg ccacattgac  13200
catccaaatc ctaaaggatt ctgtgacttg aaaggtaagt acgtccaaat acctaccact  13260
tgtgctaatg acccagtggg ttttacactt agaaacacag tctgtaccgt ctgcggaatg  13320
tggaaaggtt atggctgtag ttgtgaccaa ctccgcgaac ccttgatgca gtctgcggat  13380
gcatcaacgt tttaaacgg gtttgcggtg taagtgcagc ccgtcttaca ccgtgcggca  13440
caggcactag tactgatgtc gtctacaggg cttttgatat ttacaacgaa aaagttgctg  13500
gttttgcaaa gttcctaaaa actaattgct gtcgcttcca ggagaaggat gaggaaggca  13560
atttattaga ctcttacttt gtagttaaga ggcatactat gtctaactac caacatgaag  13620
agactattta taacttggtt aaagattgtc cagcggttgc tgtccatgac tttttcaagt  13680
ttagagtaga tggtgacatg gtaccacata tatcacgtca gcgtctaact aaatacacaa  13740
tggctgattt agtctatgct ctacgtcatt ttgatgaggg taattgtgat acattaaaag  13800
aaatactcgt cacatacaat tgctgtgatg atgattattt caataagaag gattggtatg  13860
acttcgtaga gaatcctgac atcttacgcg tatatgctaa cttaggtgag cgtgtacgcc  13920
aatcattatt aaagactgta caattctgcg atgctatgcg tgatgcaggc attgtaggcg  13980
tactgacatt agataatcag gatcttaatg ggaactggta cgatttcggt gatttcgtac  14040
aagtagcacc aggctgcgga gttcctattg tggattcata ttactcattg ctgatgccca  14100
tcctcacttt gactagggca ttggctgctg agtcccatat ggatgctgat ctcgcaaaac  14160
cacttattaa gtgggatttg ctgaaatatg attttacgga agagagactt tgtctcttcg  14220
accgttattt taaatattgg gaccagacat accatcccaa ttgtattaac tgtttggatg  14280
ataggtgtat ccttcattgt gcaaacttta atgtgttatt ttctactgtg tttccaccta  14340
caagttttgg accactagta agaaaaatat ttgtagatgg tgttcctttt gttgtttcaa  14400
ctggatacca ttttcgtgag ttaggagtcg tacataatca ggatgtaaac ttacatagct  14460
cgcgtctcag tttcaaggaa cttttagtgt atgctgctga tccagctatg catgcagctt  14520
ctggcaattt attgctagat aaacgcacta catgcttttc agtagctgca ctaacaaaca  14580
atgttgcttt tcaaactgtc aaacccggta attttaataa agacttttat gactttgctg  14640
tgtctaaagg tttctttaag gaaggaagtt ctgttgaact aaaacacttc ttctttgctc  14700
aggatggcaa cgctgctatc agtgattatg actattatcg ttataatctg ccaacaatgt  14760
gtgatatcag acaactccta ttcgtagttg aagttgttga taaatacttt gattgttacg  14820
atggtggctg tattaatgcc aaccaagtaa tcgttaacaa tctggataaa tcagctggtt  14880
```

-continued

```
tcccatttaa taaatggggt aaggctagac tttattatga ctcaatgagt tatgaggatc  14940
aagatgcact tttcgcgtat actaagcgta atgtcatccc tactataact caaatgaatc  15000
ttaagtatgc cattagtgca aagaatagag ctcgcaccgt agctggtgtc tctatctgta  15060
gtactatgac aaatagacag tttcatcaga aattattgaa gtcaatagcc gccactagag  15120
gagctactgt ggtaattgga acaagcaagt tttacggtgg ctggcataat atgttaaaaa  15180
ctgtttacag tgatgtagaa actccacacc ttatgggttg ggattatcca aaatgtgaca  15240
gagccatgcc taacatgctt aggataatgg cctctcttgt tcttgctcgc aaacataaca  15300
cttgctgtaa cttatcacac cgtttctaca ggttagctaa cgagtgtgcg caagtattaa  15360
gtgagatggt catgtgtggc ggctcactat atgttaaacc aggtggaaca tcatccggtg  15420
atgctacaac tgcttatgct aatagtgtct ttaacatttg tcaagctgtt acagccaatg  15480
taaatgcact tctttcaact gatggtaata agatagctga caagtatgtc cgcaatctac  15540
aacacaggct ctatgagtgt ctctatagaa atagggatgt tgatcatgaa ttcgtggatg  15600
agttttacgc ttacctgcgt aaacatttct ccatgatgat tctttctgat gatgccgttg  15660
tgtgctataa cagtaactat gcggctcaag gtttagtagc tagcattaag aactttaagg  15720
cagttcttta ttatcaaaat aatgtgttca tgtctgaggc aaaatgttgg actgagactg  15780
accttactaa aggacctcac gaattttgct cacagcatac aatgctagtt aaacaaggag  15840
atgattacgt gtacctgcct tacccagatc catcaagaat attaggcgca ggctgttttg  15900
tcgatgatat tgtcaaaaca gatggtacac ttatgattga aaggttcgtg tcactggcta  15960
ttgatgctta cccacttaca aaacatccta atcaggagta tgctgatgtc tttcacttgt  16020
atttacaata cattagaaag ttacatgatg agcttactgg ccacatgttg gacatgtatt  16080
ccgtaatgct aactaatgat aacacctcac ggtactggga acctgagttt tatgaggcta  16140
tgtacacacc acatacagtc ttgcaggctg taggtgcttg tgtattgtgc aattcacaga  16200
cttcacttcg ttgcggtgcc tgtattagga gaccattcct atgttgcaag tgctgctatg  16260
accatgtcat ttcaacatca cacaaattag tgttgtctgt taatccctat gtttgcaatg  16320
ccccaggttg tgatgtcact gatgtgacac aactgtatct aggaggtatg agctattatt  16380
gcaagtcaca taagcctccc attagttttc cattatgtgc taatggtcag gtttttggtt  16440
tatacaaaaa cacatgtgta ggcagtgaca atgtcactga cttcaatgcg atagcaacat  16500
gtgattggac taatgctggc gattacatac ttgccaacac ttgtactgag agactcaagc  16560
ttttcgcagc agaaacgctc aaagccactg aggaaacatt taagctgtca tatggtattg  16620
ctactgtacg cgaagtactc tctgacagag aattgcatct ttcatgggag gttggaaaac  16680
ctagaccacc attgaacaga aactatgtct ttactggtta ccgtgtaact aaaaatagta  16740
aagtacagat tggagagtac acctttgaaa aaggtgacta tggtgatgct gttgtgtaca  16800
gaggtactac gacatacaag ttgaatgttg gtgattactt tgtgttgaca tctcacactg  16860
taatgccact tagtgcacct actctagtgc cacaagagca ctatgtgaga attactggct  16920
tgtacccaac actcaacatc tcagatgagt tttctagcaa tgttgcaaat tatcaaaagg  16980
tcggcatgca aaagtactct acactccaag gaccacctgg tactggtaag agtcattttg  17040
ccatcggact tgctctctat tacccatctg ctcgcatagt gtatacggca tgctctcatg  17100
cagctgttga tgccctatgt gaaaaggcat taaaatattt gcccatagat aaatgtagta  17160
gaatcatacc tgcgcgtgcg cgcgtagagt gttttgataa attcaaagtg aattcaacac  17220
tagaacagta tgttttctgc actgtaaatg cattgccaga aacaactgct gacattgtag  17280
```

-continued

```
tctttgatga aatctctatg gctactaatt atgacttgag tgttgtcaat gctagacttc  17340
gtgcaaaaca ctacgtctat attggcgatc ctgctcaatt accagccccc cgcacattgc  17400
tgactaaagg cacactagaa ccagaatatt ttaattcagt gtgcagactt atgaaaacaa  17460
taggtccaga catgttcctt ggaacttgtc gccgttgtcc tgctgaaatt gttgacactg  17520
tgagtgcttt agtttatgac aataagctaa aagcacacaa ggataagtca gctcaatgct  17580
tcaaaatgtt ctacaaaggt gttattacac atgatgtttc atctgcaatc aacagacctc  17640
aaataggcgt tgtaagagaa tttcttacac gcaatcctgc ttggagaaaa gctgttttta  17700
tctcacctta taattcacag aacgctgtag cttcaaaaat cttaggattg cctacgcaga  17760
ctgttgattc atcacagggt tctgaatatg actatgtcat attcacacaa actactgaaa  17820
cagcacactc ttgtaatgtc aaccgcttca atgtggctat cacaagggca aaaattggca  17880
ttttgtgcat aatgtctgat agagatcttt atgacaaact gcaatttaca agtctagaaa  17940
taccacgtcg caatgtggct acattacaag cagaaaatgt aactggactt tttaaggact  18000
gtagtaagat cattactggt cttcatccta cacaggcacc tacacacctc agcgttgata  18060
taaagttcaa gactgaagga ttatgtgttg acataccagg cataccaaag gacatgacct  18120
accgtagact catctctatg atgggtttca aaatgaatta ccaagtcaat ggttacccta  18180
atatgtttat cacccgcgaa gaagctattc gtcacgttcg tgcgtggatt ggctttgatg  18240
tagagggctg tcatgcaact agagatgctg tgggtactaa cctacctctc cagctaggat  18300
tttctacagg tgttaactta gtagctgtac cgactggtta tgttgacact gaaaataaca  18360
cagaattcac cagagttaat gcaaaacctc caccaggtga ccagtttaaa catcttatac  18420
cactcatgta taaaggcttg ccctggaatg tagtgcgtat taagatagta caaatgctca  18480
gtgatacact gaaaggattg tcagacagag tcgtgttcgt cctttgggcg catggctttg  18540
agcttacatc aatgaagtac tttgtcaaga ttggacctga aagaacgtgt tgtctgtgtg  18600
acaaacgtgc aacttgcttt tctacttcat cagatactta tgcctgctgg aatcattctg  18660
tgggttttga ctatgtctat aacccattta tgattgatgt tcagcagtgg ggctttacgg  18720
gtaaccttca gagtaaccat gaccaacatt gccaggtaca tggaaatgca catgtggcta  18780
gttgtgatgc tatcatgact agatgtttag cagtccatga gtgctttgtt aagcgcgttg  18840
attggtctgt tgaataccct attataggag atgaactgag ggttaattct gcttgcagaa  18900
aagtacaaca catggttgtg aagtctgcat tgcttgctga taagtttcca gttcttcatg  18960
acattggaaa tccaaaggct atcaagtgtg tgcctcaggc tgaagtagaa tggaagttct  19020
acgatgctca gccatgtagt gacaaagctt acaaaataga ggagctcttc tattcttatg  19080
ctacacatca cgataaattc actgatggtg tttgtttgtt ttggaattgt aacgttgatc  19140
gttacccagc caatgcaatt gtgtgtaggt ttgacacaag agtcttgtca aacttgaact  19200
taccaggctg tgatggtggt agtttgtatg tgaataagca tgcattccac actccagctt  19260
tcgataaaag tgcatttact aatttaaagc aattgccttt cttttactat tctgatagtc  19320
cttgtgagtc tcatggcaaa caagtagtgt cggatattga ttatgttcca ctcaaatctg  19380
ctacgtgtat tacacgatgc aatttaggtg gtgctgtttg cagacaccat gcaaatgagt  19440
accgacagta cttggatgca tataatatga tgatttctgc tggatttagc ctatggattt  19500
acaaacaatt tgatacttat aacctgtgga atacatttac caggttacag agtttagaaa  19560
atgtggctta taatgttgtt aataaaggac actttgatgg acacgccggc gaagcacctg  19620
```

-continued

```
tttccatcat taataatgct gtttacacaa aggtagatgg tattgatgtg gagatctttg  19680
aaaataagac aacacttcct gttaatgttg catttgagct ttgggctaag cgtaacatta  19740
aaccagtgcc agagattaag atactcaata atttgggtgt tgatatcgct gctaatactg  19800
taatctggga ctacaaaaga gaagccccag cacatgtatc tacaataggt gtctgcacaa  19860
tgactgacat tgccaagaaa cctactgaga gtgcttgttc ttcacttact gtcttgtttg  19920
atggtagagt ggaaggacag gtagaccttt ttagaaacgc ccgtaatggt gttttaataa  19980
cagaaggttc agtcaaaggt ctaacacctt caaagggacc agcacaagct agcgtcaatg  20040
gagtcacatt aattggagaa tcagtaaaaa cacagtttaa ctactttaag aaagtagacg  20100
gcattattca acagttgcct gaaacctact ttactcagag cagagactta gaggatttta  20160
agcccagatc acaaatggaa actgactttc tcgagctcgc tatggatgaa ttcatacagc  20220
gatataagct cgagggctat gccttcgaac acatcgttta tggagatttc agtcatggac  20280
aacttggcgg tcttcattta atgataggct tagccaagcg ctcacaagat tcaccactta  20340
aattagagga ttttatccct atggacagca cagtgaaaaa ttacttcata acagatgcgc  20400
aaacaggttc atcaaaatgt gtgtgttctg tgattgatct tttacttgat gactttgtcg  20460
agataataaa gtcacaagat ttgtcagtga tttcaaaagt ggtcaaggtt acaattgact  20520
atgctgaaat ttcattcatg ctttggtgta aggatggaca tgttgaaacc ttctacccaa  20580
aactacaagc aagtcaagcg tggcaaccag gtgttgcgat gcctaacttg tacaagatgc  20640
aaagaatgct tcttgaaaag tgtgaccttc agaattatgg tgaaaatgct gttataccaa  20700
aaggaataat gatgaatgtc gcaaagtata ctcaactgtg tcaatactta aatacactta  20760
ctttagctgt accctacaac atgagagtta ttcactttgg tgctggctct gataaaggag  20820
ttgcaccagg tacagctgtg ctcagacaat ggttgccaac tggcacacta cttgtcgatt  20880
cagatcttaa tgacttcgtc tccgacgcag attctacttt aattggagac tgtgcaacag  20940
tacatacggc taataaatgg gaccttatta ttagcgatat gtatgaccct aggaccaaac  21000
atgtgacaaa agagaatgac tctaaagaag ggtttttcac ttatctgtgt ggatttataa  21060
agcaaaaact agccctgggt ggttctatag ctgtaaagat aacagagcat tcttggaatg  21120
ctgaccttta caagcttatg ggccatttct catggtggac agcttttgtt acaaatgtaa  21180
atgcatcatc atcggaagca tttttaattg ggctaacta tcttggcaag ccgaaggaac  21240
aaattgatgg ctataccatg catgctaact acattttctg gaggaacaca aatcctatcc  21300
agttgtcttc ctattcactc tttgacatga gcaaatttcc tcttaaatta agaggaactg  21360
ctgtaatgtc tcttaaggag aatcaaatca atgatatgat ttattctctt ctggaaaaag  21420
gtaggcttat cattagagaa aacaacagag ttgtggtttc aagtgatatt cttgttaaca  21480
actaaacgaa catgtttatt ttcttattat ttcttactct cactagtggt agtgaccttg  21540
accggtgcac cacttttgat gatgttcaag ctcctaatta cactcaacat acttcatcta  21600
tgagggggt ttactatcct gatgaaattt ttagatcaga cactctttat ttaactcagg  21660
atttatttct tccattttat tctaatgtta cagggtttca tactattaat catacgtttg  21720
gcaaccctgt catacctttt aaggatggta tttattttgc tgccacagag aaatcaaatg  21780
ttgtccgtgg ttgggttttt ggttctacca tgaacaacaa gtcacagtcg gtgattatta  21840
ttaacaattc tactaatgtt gttatacgag catgtaactt tgaattgtgt gacaaccctt  21900
tctttgctgt ttctaaaccc atgggtacac agacacatac tatgatattc gataatgcat  21960
ttaattgcac tttcgagtac atatctgatg ccttttcgct tgatgtttca gaaaagtcag  22020
```

-continued

```
gtaattttaa acacttacga gagtttgtgt ttaaaaataa agatgggttt ctctatgttt  22080
ataagggcta tcaacctata gatgtagttc gtgatctacc ttctggtttt aacactttga  22140
aacctatttt taagttgcct cttggtatta acattacaaa ttttagagcc attcttacag  22200
ccttttcacc tgctcaagac atttggggca cgtcagctgc agcctatttt gttggctatt  22260
taaagccaac tacatttatg ctcaagtatg atgaaaatgg tacaatcaca gatgctgttg  22320
attgttctca aaatccactt gctgaactca aatgctctgt taagagcttt gagattgaca  22380
aaggaattta ccagacctct aatttcaggg ttgttccctc aggagatgtt gtgagattcc  22440
ctaatattac aaacttgtgt ccttttggag aggtttttaa tgctactaaa ttcccttctg  22500
tctatgcatg ggagagaaaa aaaatttcta attgtgttgc tgattactct gtgctctaca  22560
actcaacatt tttttcaacc tttaagtgct atggcgtttc tgccactaag ttgaatgatc  22620
tttgcttctc caatgtctat gcagattctt ttgtagtcaa gggagatgat gtaagacaaa  22680
tagcgccagg acaaactggt gttattgctg attataatta taaattgcca gatgatttca  22740
tgggttgtgt ccttgcttgg aatactagga acattgatgc tacttcaact ggtaattata  22800
attataaata taggtatctt agacatggca agcttaggcc ctttgagaga gacatatcta  22860
atgtgccttt ctcccctgat ggcaaacctt gcaccccacc tgctcttaat tgttattggc  22920
cattaaatga ttatggtttt tacaccacta ctggcattgg ctaccaacct tacagagttg  22980
tagtactttc ttttgaactt ttaaatgcac cggccacggt ttgtggacca aaattatcca  23040
ctgaccttat taagaaccag tgtgtcaatt ttaattttaa tggactcact ggtactggtg  23100
tgttaactcc ttcttcaaag agatttcaac catttcaaca atttggccgt gatgtttctg  23160
atttcactga ttccgttcga gatcctaaaa catctgaaat attagacatt tcaccttgct  23220
cttttggggg tgtaagtgta attacacctg gaacaaatgc ttcatctgaa gttgctgttc  23280
tatatcaaga tgttaactgc actgatgttt ctacagcaat tcatgcagat caactcacac  23340
cagcttggcg catatattct actggaaaca atgtattcca gactcaagca ggctgtctta  23400
taggagctga gcatgtcgac acttcttatg agtgcgacat tcctattgga gctggcattt  23460
gtgctagtta ccatacagtt tctttattac gtagtactag ccaaaaatct attgtggctt  23520
atactatgtc tttaggtgct gatagttcaa ttgcttactc taataacacc attgctatac  23580
ctactaactt ttcaattagc attactacag aagtaatgcc tgtttctatg gctaaaacct  23640
ccgtagattg taatatgtac atctgcggag attctactga atgtgctaat ttgcttctcc  23700
aatatggtag cttttgcaca caactaaatc gtgcactctc aggtattgct gctgaacagg  23760
atcgcaacac acgtgaagtg ttcgctcaag tcaaacaaat gtacaaaacc ccaactttga  23820
aatattttgg tggttttaat ttttcacaaa tattacctga ccctctaaag ccaactaaga  23880
ggtcttttat tgaggacttg ctctttaata aggtgacact cgctgatgct ggcttcatga  23940
agcaatatgg cgaatgccta ggtgatatta atgctagaga tctcatttgt gcgcagaagt  24000
tcaatggact tacagtgttg ccacctctgc tcactgatga tatgattgct gcctacactg  24060
ctgctctagt tagtggtact gccactgctg gatggacatt tggtgctggc gctgctcttc  24120
aaataccttt tgctatgcaa atggcatata ggttcaatgg cattggagtt acccaaaatg  24180
ttctctatga gaaccaaaaa caaatcgcca accaatttaa caaggcgatt agtcaaattc  24240
aagaatcact tacaacaaca tcaactgcat tgggcaagct gcaagacgtt gttaaccaga  24300
atgctcaagc attaaacaca cttgttaaac aacttagctc taattttggt gcaatttcaa  24360
```

-continued

```
gtgtgctaaa tgatatcctt tcgcgacttg ataaagtcga ggcggaggta caaattgaca  24420
ggttaattac aggcagactt caaagccttc aaacctatgt aacacaacaa ctaatcaggg  24480
ctgctgaaat cagggcttct gctaatcttg ctgctactaa aatgtctgag tgtgttcttg  24540
gacaatcaaa aagagttgac ttttgtggaa agggctacca ccttatgtcc ttcccacaag  24600
cagccccgca tggtgttgtc ttcctacatg tcacgtatgt gccatcccag gagaggaact  24660
tcaccacagc gccagcaatt tgtcatgaag gcaaagcata cttccctcgt gaaggtgttt  24720
ttgtgtttaa tggcacttct tggtttatta cacagaggaa cttcttttct ccacaaataa  24780
ttactacaga caatacattt gtctcaggaa attgtgatgt cgttattggc atcattaaca  24840
acacagttta tgatcctctg caacctgagc tcgactcatt caaagaagag ctggacaagt  24900
acttcaaaaa tcatacatca ccagatgttg atcttggcga catttcaggc attaacgctt  24960
ctgtcgtcaa cattcaaaaa gaaattgacc gcctcaatga ggtcgctaaa aatttaaatg  25020
aatcactcat tgaccttcaa gaattgggaa aatatgagca atatattaaa tggccttggt  25080
atgtttggct cggcttcatt gctggactaa ttgccatcgt catggttaca atcttgcttt  25140
gttgcatgac tagttgttgc agttgcctca agggtgcatg ctcttgtggt tcttgctgca  25200
agtttgatga ggatgactct gagccagttc tcaagggtgt caaattacat tacacataaa  25260
cgaacttatg gatttgttta tgagattttt tactcttgga tcaattactg cacagccagt  25320
aaaaattgac aatgcttctc ctgcaagtac tgttcatgct acagcaacga taccgctaca  25380
agcctcactc cctttcggat ggcttgttat tggcgttgca tttcttgctg tttttcagag  25440
cgctaccaaa ataattgcgc tcaataaaag atggcagcta gccctttata agggcttcca  25500
gttcatttgc aatttactgc tgctatttgt taccatctat tcacatcttt tgcttgtcgc  25560
tgcaggtatg gaggcgcaat ttttgtacct ctatgccttg atatattttc tacaatgcat  25620
caacgcatgt agaattatta tgagatgttg gctttgttgg aagtgcaaat ccaagaaccc  25680
attactttat gatgccaact actttgtttg ctggcacaca cataactatg actactgtat  25740
accatataac agtgtcacag atacaattgt cgttactgaa ggtgacggca tttcaacacc  25800
aaaactcaaa gaagactacc aaattggtgg ttattctgag gataggcact caggtgttaa  25860
agactatgtc gttgtacatg gctatttcac cgaagtttac taccagcttg agtctacaca  25920
aattactaca gacactggta ttgaaaatgc tacattcttc atctttaaca agcttgttaa  25980
agacccaccg aatgtgcaaa tacacacaat cgacggctct tcaggagttg ctaatccagc  26040
aatggatcca atttatgatg agccgacgac gactactagc gtgcctttgt aagcacaaga  26100
aagtgagtac gaacttatgt actcattcgt ttcggaagaa acaggtacgt taatagttaa  26160
tagcgtactt ctttttcttg ctttcgtggt attcttgcta gtcacactag ccatccttac  26220
tgcgcttcga ttgtgtgcgt actgctgcaa tattgttaac gtgagtttag taaaaccaac  26280
ggtttacgtc tactcgcgtg ttaaaaatct gaactcttct gaaggagttc ctgatcttct  26340
ggtctaaacg aactaactat tattattatt ctgtttggaa ctttaacatt gcttatcatg  26400
gcagacaacg gtactattac cgttgaggag cttaaacaac tcctggaaca atggaaccta  26460
gtaataggtt tcctattcct agcctggatt atgttactac aatttgccta ttctaatcgg  26520
aacaggtttt tgtacataat aaagcttgtt ttcctctggc tcttgtggcc agtaacactt  26580
gcttgttttg tgcttgctgc tgtctacaga attaattggg tgactggcgg gattgcgatt  26640
gcaatggctt gtattgtagg cttgatgtgg cttagctact tcgttgcttc cttcaggctg  26700
tttgctcgta cccgctcaat gtggtcattc aacccagaaa caaacattct tctcaatgtg  26760
```

-continued

```
cctctccggg ggacaattgt gaccagaccg ctcatggaaa gtgaacttgt cattggtgct  26820
gtgatcattc gtggtcactt gcgaatggcc ggacaccccc tagggcgctg tgacattaag  26880
gacctgccaa aagagatcac tgtggctaca tcacgaacgc tttcttatta caaattagga  26940
gcgtcgcagc gtgtaggcac tgattcaggt tttgctgcat acaaccgcta ccgtattgga  27000
aactataaat taaatacaga ccacgccggt agcaacgaca atattgcttt gctagtacag  27060
taagtgacaa cagatgtttc atcttgttga cttccaggtt acaatagcag agatattgat  27120
tatcattatg aggactttca ggattgctat ttggaatctt gacgttataa taagttcaat  27180
agtgagacaa ttatttaagc ctctaactaa gaagaattat tcggagttag atgatgaaga  27240
acctatggag ttagattatc cataaaacga acatgaaaat tattctcttc ctgacattga  27300
ttgtatttac atcttgcgag ctatatcact atcaggagtg tgttagaggt acgactgtac  27360
tactaaaaga accttgccca tcaggaacat acgagggcaa ttcaccattt caccctcttg  27420
ctgacaataa atttgcacta acttgcacta gcacacactt tgcttttgct tgtgctgacg  27480
gtactcgaca tacctatcag ctgcgtgcaa gatcagtttc accaaaactt ttcatcagac  27540
aagaggaggt tcaacaagag ctctactcgc cactttttct cattgttgct gctctagtat  27600
ttttaatact ttgcttcacc attaagagaa agacagaatg aatgagctca ctttaattga  27660
cttctatttg tgctttttag cctttctgct attccttgtt ttaataatgc ttattatatt  27720
ttggttttca ctcgaaatcc aggatctaga agaaccttgt accaaagtct aaacgaacat  27780
gaaacttctc attgttttga cttgtatttc tctatgcagt tgcatatgca ctgtagtaca  27840
gcgctgtgca tctaataaac ctcatgtgct tgaagatcct tgtaaggtac aacactaggg  27900
gtaatactta tagcactgct tggctttgtg ctctaggaaa ggttttacct tttcatagat  27960
ggcacactat ggttcaaaca tgcacaccta atgttactat caactgtcaa gatccagctg  28020
gtggtgcgct tatagctagg tgttggtacc ttcatgaagg tcaccaaact gctgcattta  28080
gagacgtact tgttgtttta aataaacgaa caaattaaaa tgtctgataa tggaccccaa  28140
tcaaaccaac gtagtgcccc ccgcattaca tttggtggac ccacagattc aactgacaat  28200
aaccagaatg gaggacgcaa tggggcaagg ccaaaacagc gccgacccca aggtttaccc  28260
aataatactg cgtcttggtt cacagctctc actcagcatg gcaaggagga acttagattc  28320
cctcgaggcc agggcgttcc aatcaacacc aatagtggtc cagatgacca aattggctac  28380
taccgaagag ctacccgacg agttcgtggt ggtgacggca aaatgaaaga gctcagcccc  28440
agatggtact tctattacct aggaactggc ccagaagctt cacttcccta cggcgctaac  28500
aaagaaggca tcgtatgggt tgcaactgag ggagccttga atacacccaa agaccacatt  28560
ggcacccgca atcctaataa caatgctgcc accgtgctac aacttcctca aggaacaaca  28620
ttgccaaaag gcttctacgc agagggaagc agaggcggca gtcaagcctc ttctcgctcc  28680
tcatcacgta gtcgcggtaa ttcaagaaat tcaactcctg gcagcagtag gggaaattct  28740
cctgctcgaa tggctagcgg aggtggtgaa actgccctcg cgctattgct gctagacaga  28800
ttgaaccagc ttgagagcaa agtttctggt aaaggccaac aacaacaagg ccaaactgtc  28860
actaagaaat ctgctgctga ggcatctaaa aagcctcgcc aaaaacgtac tgccacaaaa  28920
cagtacaacg tcactcaagc atttgggaga cgtggtccag aacaaaccca aggaaatttc  28980
ggggaccaag acctaatcag acaaggaact gattacaaac attggccgca aattgcacaa  29040
tttgctccaa gtgcctctgc attctttgga atgtcacgca ttggcatgga agtcacacct  29100
```

-continued

```
tcgggaacat ggctgactta tcatggagcc attaaattgg atgacaaaga tccacaattc  29160

aaagacaacg tcatactgct gaacaagcac attgacgcat acaaaacatt cccaccaaca  29220

gagcctaaaa aggacaaaaa gaaaaagact gatgaagctc agcctttgcc gcagagacaa  29280

aagaagcagc ccactgtgac tcttcttcct gcggctgaca tggatgattt ctccagacaa  29340

cttcaaaatt ccatgagtgg agcttctgct gattcaactc aggcataaac actcatgatg  29400

accacacaag gcagatgggc tatgtaaacg ttttcgcaat tccgtttacg atacatagtc  29460

tactcttgtg cagaatgaat tctcgtaact aaacagcaca agtaggttta gttaacttta  29520

atctcacata gcaatcttta atcaatgtgt aacattaggg aggacttgaa agagccacca  29580

cattttcatc gaggccacgc ggagtacgat cgagggtaca gtgaataatg ctagggagag  29640

ctgcctatat ggaagagccc taatgtgtaa aattaatttt agtagtgcta tccccatgtg  29700

attttaatag cttcttagga gaatgac                                     29727


<210> SEQ ID NO 2
<211> LENGTH: 7073
<212> TYPE: PRT
<213> ORGANISM: SARS coronavirus Urbani

<400> SEQUENCE: 2

Met Glu Ser Leu Val Leu Gly Val Asn Glu Lys Thr His Val Gln Leu
1               5                   10                  15

Ser Leu Pro Val Leu Gln Val Arg Asp Val Leu Val Arg Gly Phe Gly
            20                  25                  30

Asp Ser Val Glu Glu Ala Leu Ser Glu Ala Arg Glu His Leu Lys Asn
        35                  40                  45

Gly Thr Cys Gly Leu Val Glu Leu Glu Lys Gly Val Leu Pro Gln Leu
    50                  55                  60

Glu Gln Pro Tyr Val Phe Ile Lys Arg Ser Asp Ala Leu Ser Thr Asn
65                  70                  75                  80

His Gly His Lys Val Val Glu Leu Val Ala Glu Met Asp Gly Ile Gln
                85                  90                  95

Tyr Gly Arg Ser Gly Ile Thr Leu Gly Val Leu Val Pro His Val Gly
            100                 105                 110

Glu Thr Pro Ile Ala Tyr Arg Asn Val Leu Leu Arg Lys Asn Gly Asn
        115                 120                 125

Lys Gly Ala Gly Gly His Ser Tyr Gly Ile Asp Leu Lys Ser Tyr Asp
    130                 135                 140

Leu Gly Asp Glu Leu Gly Thr Asp Pro Ile Glu Asp Tyr Glu Gln Asn
145                 150                 155                 160

Trp Asn Thr Lys His Gly Ser Gly Ala Leu Arg Glu Leu Thr Arg Glu
                165                 170                 175

Leu Asn Gly Gly Ala Val Thr Arg Tyr Val Asp Asn Asn Phe Cys Gly
            180                 185                 190

Pro Asp Gly Tyr Pro Leu Asp Cys Ile Lys Asp Phe Leu Ala Arg Ala
        195                 200                 205

Gly Lys Ser Met Cys Thr Leu Ser Glu Gln Leu Asp Tyr Ile Glu Ser
    210                 215                 220

Lys Arg Gly Val Tyr Cys Cys Arg Asp His Glu His Glu Ile Ala Trp
225                 230                 235                 240

Phe Thr Glu Arg Ser Asp Lys Ser Tyr Glu His Gln Thr Pro Phe Glu
                245                 250                 255

Ile Lys Ser Ala Lys Lys Phe Asp Thr Phe Lys Gly Glu Cys Pro Lys
```

-continued

```
            260                 265                 270

Phe Val Phe Pro Leu Asn Ser Lys Val Lys Val Ile Gln Pro Arg Val
        275                 280                 285

Glu Lys Lys Lys Thr Glu Gly Phe Met Gly Arg Ile Arg Ser Val Tyr
    290                 295                 300

Pro Val Ala Ser Pro Gln Glu Cys Asn Asn Met His Leu Ser Thr Leu
305                 310                 315                 320

Met Lys Cys Asn His Cys Asp Glu Val Ser Trp Gln Thr Cys Asp Phe
                325                 330                 335

Leu Lys Ala Thr Cys Glu His Cys Gly Thr Glu Asn Leu Val Ile Glu
            340                 345                 350

Gly Pro Thr Thr Cys Gly Tyr Leu Pro Thr Asn Ala Val Val Lys Met
        355                 360                 365

Pro Cys Pro Ala Cys Gln Asp Pro Glu Ile Gly Pro Glu His Ser Val
    370                 375                 380

Ala Asp Tyr His Asn His Ser Asn Ile Glu Thr Arg Leu Arg Lys Gly
385                 390                 395                 400

Gly Arg Thr Arg Cys Phe Gly Gly Cys Val Phe Ala Tyr Val Gly Cys
                405                 410                 415

Tyr Asn Lys Arg Ala Tyr Trp Val Pro Arg Ala Ser Ala Asp Ile Gly
            420                 425                 430

Ser Gly His Thr Gly Ile Thr Gly Asp Asn Val Glu Thr Leu Asn Glu
        435                 440                 445

Asp Leu Leu Glu Ile Leu Ser Arg Glu Arg Val Asn Ile Asn Ile Val
    450                 455                 460

Gly Asp Phe His Leu Asn Glu Glu Val Ala Ile Ile Leu Ala Ser Phe
465                 470                 475                 480

Ser Ala Ser Thr Ser Ala Phe Ile Asp Thr Ile Lys Ser Leu Asp Tyr
                485                 490                 495

Lys Ser Phe Lys Thr Ile Val Glu Ser Cys Gly Asn Tyr Lys Val Thr
            500                 505                 510

Lys Gly Lys Pro Val Lys Gly Ala Trp Asn Ile Gly Gln Gln Arg Ser
        515                 520                 525

Val Leu Thr Pro Leu Cys Gly Phe Pro Ser Gln Ala Ala Gly Val Ile
    530                 535                 540

Arg Ser Ile Phe Ala Arg Thr Leu Asp Ala Ala Asn His Ser Ile Pro
545                 550                 555                 560

Asp Leu Gln Arg Ala Ala Val Thr Ile Leu Asp Gly Ile Ser Glu Gln
                565                 570                 575

Ser Leu Arg Leu Val Asp Ala Met Val Tyr Thr Ser Asp Leu Leu Thr
            580                 585                 590

Asn Ser Val Ile Ile Met Ala Tyr Val Thr Gly Gly Leu Val Gln Gln
        595                 600                 605

Thr Ser Gln Trp Leu Ser Asn Leu Leu Gly Thr Thr Val Glu Lys Leu
    610                 615                 620

Arg Pro Ile Phe Glu Trp Ile Glu Ala Lys Leu Ser Ala Gly Val Glu
625                 630                 635                 640

Phe Leu Lys Asp Ala Trp Glu Ile Leu Lys Phe Leu Ile Thr Gly Val
                645                 650                 655

Phe Asp Ile Val Lys Gly Gln Ile Gln Val Ala Ser Asp Asn Ile Lys
            660                 665                 670

Asp Cys Val Lys Cys Phe Ile Asp Val Val Asn Lys Ala Leu Glu Met
        675                 680                 685
```

-continued

```
Cys Ile Asp Gln Val Thr Ile Ala Gly Ala Lys Leu Arg Ser Leu Asn
    690                 695                 700

Leu Gly Glu Val Phe Ile Ala Gln Ser Lys Gly Leu Tyr Arg Gln Cys
705                 710                 715                 720

Ile Arg Gly Lys Glu Gln Leu Gln Leu Leu Met Pro Leu Lys Ala Pro
                725                 730                 735

Lys Glu Val Thr Phe Leu Glu Gly Asp Ser His Asp Thr Val Leu Thr
            740                 745                 750

Ser Glu Glu Val Val Leu Lys Asn Gly Glu Leu Glu Ala Leu Glu Thr
        755                 760                 765

Pro Val Asp Ser Phe Thr Asn Gly Ala Ile Val Gly Thr Pro Val Cys
    770                 775                 780

Val Asn Gly Leu Met Leu Leu Glu Ile Lys Asp Lys Glu Gln Tyr Cys
785                 790                 795                 800

Ala Leu Ser Pro Gly Leu Leu Ala Thr Asn Asn Val Phe Arg Leu Lys
                805                 810                 815

Gly Gly Ala Pro Ile Lys Gly Val Thr Phe Gly Glu Asp Thr Val Trp
            820                 825                 830

Glu Val Gln Gly Tyr Lys Asn Val Arg Ile Thr Phe Glu Leu Asp Glu
        835                 840                 845

Arg Val Asp Lys Val Leu Asn Glu Lys Cys Ser Val Tyr Thr Val Glu
    850                 855                 860

Ser Gly Thr Glu Val Thr Glu Phe Ala Cys Val Val Ala Glu Ala Val
865                 870                 875                 880

Val Lys Thr Leu Gln Pro Val Ser Asp Leu Leu Thr Asn Met Gly Ile
                885                 890                 895

Asp Leu Asp Glu Trp Ser Val Ala Thr Phe Tyr Leu Phe Asp Asp Ala
            900                 905                 910

Gly Glu Glu Asn Phe Ser Ser Arg Met Tyr Cys Ser Phe Tyr Pro Pro
        915                 920                 925

Asp Glu Glu Glu Glu Asp Asp Ala Glu Cys Glu Glu Glu Glu Ile Asp
    930                 935                 940

Glu Thr Cys Glu His Glu Tyr Gly Thr Glu Asp Asp Tyr Gln Gly Leu
945                 950                 955                 960

Pro Leu Glu Phe Gly Ala Ser Ala Glu Thr Val Arg Val Glu Glu Glu
                965                 970                 975

Glu Glu Glu Asp Trp Leu Asp Asp Thr Thr Glu Gln Ser Glu Ile Glu
            980                 985                 990

Pro Glu Pro Glu Pro Thr Pro Glu Glu Pro Val Asn Gln Phe Thr Gly
        995                 1000                1005

Tyr Leu Lys Leu Thr Asp Asn Val Ala Ile Lys Cys Val Asp Ile Val
    1010                1015                1020

Lys Glu Ala Gln Ser Ala Asn Pro Met Val Ile Val Asn Ala Ala Asn
1025                1030                1035                1040

Ile His Leu Lys His Gly Gly Gly Val Ala Gly Ala Leu Asn Lys Ala
                1045                1050                1055

Thr Asn Gly Ala Met Gln Lys Glu Ser Asp Asp Tyr Ile Lys Leu Asn
            1060                1065                1070

Gly Pro Leu Thr Val Gly Gly Ser Cys Leu Leu Ser Gly His Asn Leu
        1075                1080                1085

Ala Lys Lys Cys Leu His Val Val Gly Pro Asn Leu Asn Ala Gly Glu
    1090                1095                1100
```

-continued

```
Asp Ile Gln Leu Leu Lys Ala Ala Tyr Glu Asn Phe Asn Ser Gln Asp
1105                1110                1115                1120

Ile Leu Leu Ala Pro Leu Leu Ser Ala Gly Ile Phe Gly Ala Lys Pro
                1125                1130                1135

Leu Gln Ser Leu Gln Val Cys Val Gln Thr Val Arg Thr Gln Val Tyr
            1140                1145                1150

Ile Ala Val Asn Asp Lys Ala Leu Tyr Glu Gln Val Val Met Asp Tyr
        1155                1160                1165

Leu Asp Asn Leu Lys Pro Arg Val Glu Ala Pro Lys Gln Glu Glu Pro
    1170                1175                1180

Pro Asn Thr Glu Asp Ser Lys Thr Glu Glu Lys Ser Val Val Gln Lys
1185                1190                1195                1200

Pro Val Asp Val Lys Pro Lys Ile Lys Ala Cys Ile Asp Glu Val Thr
                1205                1210                1215

Thr Thr Leu Glu Glu Thr Lys Phe Leu Thr Asn Lys Leu Leu Leu Phe
            1220                1225                1230

Ala Asp Ile Asn Gly Lys Leu Tyr His Asp Ser Gln Asn Met Leu Arg
        1235                1240                1245

Gly Glu Asp Met Ser Phe Leu Glu Lys Asp Ala Pro Tyr Met Val Gly
    1250                1255                1260

Asp Val Ile Thr Ser Gly Asp Ile Thr Cys Val Val Ile Pro Ser Lys
1265                1270                1275                1280

Lys Ala Gly Gly Thr Thr Glu Met Leu Ser Arg Ala Leu Lys Lys Val
                1285                1290                1295

Pro Val Asp Glu Tyr Ile Thr Thr Tyr Pro Gly Gln Gly Cys Ala Gly
            1300                1305                1310

Tyr Thr Leu Glu Glu Ala Lys Thr Ala Leu Lys Lys Cys Lys Ser Ala
        1315                1320                1325

Phe Tyr Val Leu Pro Ser Glu Ala Pro Asn Ala Lys Glu Glu Ile Leu
    1330                1335                1340

Gly Thr Val Ser Trp Asn Leu Arg Glu Met Leu Ala His Ala Glu Glu
1345                1350                1355                1360

Thr Arg Lys Leu Met Pro Ile Cys Met Asp Val Arg Ala Ile Met Ala
                1365                1370                1375

Thr Ile Gln Arg Lys Tyr Lys Gly Ile Lys Ile Gln Glu Gly Ile Val
            1380                1385                1390

Asp Tyr Gly Val Arg Phe Phe Phe Tyr Thr Ser Lys Glu Pro Val Ala
        1395                1400                1405

Ser Ile Ile Thr Lys Leu Asn Ser Leu Asn Glu Pro Leu Val Thr Met
    1410                1415                1420

Pro Ile Gly Tyr Val Thr His Gly Phe Asn Leu Glu Glu Ala Ala Arg
1425                1430                1435                1440

Cys Met Arg Ser Leu Lys Ala Pro Ala Val Val Ser Val Ser Ser Pro
                1445                1450                1455

Asp Ala Val Thr Thr Tyr Asn Gly Tyr Leu Thr Ser Ser Ser Lys Thr
            1460                1465                1470

Ser Glu Glu His Phe Val Glu Thr Val Ser Leu Ala Gly Ser Tyr Arg
        1475                1480                1485

Asp Trp Ser Tyr Ser Gly Gln Arg Thr Glu Leu Gly Val Glu Phe Leu
    1490                1495                1500

Lys Arg Gly Asp Lys Ile Val Tyr His Thr Leu Glu Ser Pro Val Glu
1505                1510                1515                1520

Phe His Leu Asp Gly Glu Val Leu Ser Leu Asp Lys Leu Lys Ser Leu
```

-continued

```
                1525                1530                1535

Leu Ser Leu Arg Glu Val Lys Thr Ile Lys Val Phe Thr Thr Val Asp
            1540                1545                1550

Asn Thr Asn Leu His Thr Gln Leu Val Asp Met Ser Met Thr Tyr Gly
        1555                1560                1565

Gln Gln Phe Gly Pro Thr Tyr Leu Asp Gly Ala Asp Val Thr Lys Ile
    1570                1575                1580

Lys Pro His Val Asn His Glu Gly Lys Thr Phe Phe Val Leu Pro Ser
1585                1590                1595                1600

Asp Asp Thr Leu Arg Ser Glu Ala Phe Glu Tyr Tyr His Thr Leu Asp
                1605                1610                1615

Glu Ser Phe Leu Gly Arg Tyr Met Ser Ala Leu Asn His Thr Lys Lys
            1620                1625                1630

Trp Lys Phe Pro Gln Val Gly Gly Leu Thr Ser Ile Lys Trp Ala Asp
        1635                1640                1645

Asn Asn Cys Tyr Leu Ser Ser Val Leu Leu Ala Leu Gln Gln Leu Glu
    1650                1655                1660

Val Lys Phe Asn Ala Pro Ala Leu Gln Glu Ala Tyr Tyr Arg Ala Arg
1665                1670                1675                1680

Ala Gly Asp Ala Ala Asn Phe Cys Ala Leu Ile Leu Ala Tyr Ser Asn
                1685                1690                1695

Lys Thr Val Gly Glu Leu Gly Asp Val Arg Glu Thr Met Thr His Leu
            1700                1705                1710

Leu Gln His Ala Asn Leu Glu Ser Ala Lys Arg Val Leu Asn Val Val
        1715                1720                1725

Cys Lys His Cys Gly Gln Lys Thr Thr Thr Leu Thr Gly Val Glu Ala
    1730                1735                1740

Val Met Tyr Met Gly Thr Leu Ser Tyr Asp Asn Leu Lys Thr Gly Val
1745                1750                1755                1760

Ser Ile Pro Cys Val Cys Gly Arg Asp Ala Thr Gln Tyr Leu Val Gln
                1765                1770                1775

Gln Glu Ser Ser Phe Val Met Met Ser Ala Pro Pro Ala Glu Tyr Lys
            1780                1785                1790

Leu Gln Gln Gly Thr Phe Leu Cys Ala Asn Glu Tyr Thr Gly Asn Tyr
        1795                1800                1805

Gln Cys Gly His Tyr Thr His Ile Thr Ala Lys Glu Thr Leu Tyr Arg
    1810                1815                1820

Ile Asp Gly Ala His Leu Thr Lys Met Ser Glu Tyr Lys Gly Pro Val
1825                1830                1835                1840

Thr Asp Val Phe Tyr Lys Glu Thr Ser Tyr Thr Thr Thr Ile Lys Pro
                1845                1850                1855

Val Ser Tyr Lys Leu Asp Gly Val Thr Tyr Thr Glu Ile Glu Pro Lys
            1860                1865                1870

Leu Asp Gly Tyr Tyr Lys Lys Asp Asn Ala Tyr Tyr Thr Glu Gln Pro
        1875                1880                1885

Ile Asp Leu Val Pro Thr Gln Pro Leu Pro Asn Ala Ser Phe Asp Asn
    1890                1895                1900

Phe Lys Leu Thr Cys Ser Asn Thr Lys Phe Ala Asp Asp Leu Asn Gln
1905                1910                1915                1920

Met Thr Gly Phe Thr Lys Pro Ala Ser Arg Glu Leu Ser Val Thr Phe
                1925                1930                1935

Phe Pro Asp Leu Asn Gly Asp Val Val Ala Ile Asp Tyr Arg His Tyr
            1940                1945                1950
```

-continued

```
Ser Ala Ser Phe Lys Lys Gly Ala Lys Leu Leu His Lys Pro Ile Val
        1955                1960                1965

Trp His Ile Asn Gln Ala Thr Thr Lys Thr Thr Phe Lys Pro Asn Thr
    1970                1975                1980

Trp Cys Leu Arg Cys Leu Trp Ser Thr Lys Pro Val Asp Thr Ser Asn
1985                1990                1995                2000

Ser Phe Glu Val Leu Ala Val Glu Asp Thr Gln Gly Met Asp Asn Leu
                2005                2010                2015

Ala Cys Glu Ser Gln Gln Pro Thr Ser Glu Glu Val Val Glu Asn Pro
            2020                2025                2030

Thr Ile Gln Lys Glu Val Ile Glu Cys Asp Val Lys Thr Thr Glu Val
        2035                2040                2045

Val Gly Asn Val Ile Leu Lys Pro Ser Asp Glu Gly Val Lys Val Thr
    2050                2055                2060

Gln Glu Leu Gly His Glu Asp Leu Met Ala Ala Tyr Val Glu Asn Thr
2065                2070                2075                2080

Ser Ile Thr Ile Lys Lys Pro Asn Glu Leu Ser Leu Ala Leu Gly Leu
                2085                2090                2095

Lys Thr Ile Ala Thr His Gly Ile Ala Ala Ile Asn Ser Val Pro Trp
            2100                2105                2110

Ser Lys Ile Leu Ala Tyr Val Lys Pro Phe Leu Gly Gln Ala Ala Ile
        2115                2120                2125

Thr Thr Ser Asn Cys Ala Lys Arg Leu Ala Gln Arg Val Phe Asn Asn
    2130                2135                2140

Tyr Met Pro Tyr Val Phe Thr Leu Leu Phe Gln Leu Cys Thr Phe Thr
2145                2150                2155                2160

Lys Ser Thr Asn Ser Arg Ile Arg Ala Ser Leu Pro Thr Thr Ile Ala
                2165                2170                2175

Lys Asn Ser Val Lys Ser Val Ala Lys Leu Cys Leu Asp Ala Gly Ile
            2180                2185                2190

Asn Tyr Val Lys Ser Pro Lys Phe Ser Lys Leu Phe Thr Ile Ala Met
        2195                2200                2205

Trp Leu Leu Leu Leu Ser Ile Cys Leu Gly Ser Leu Ile Cys Val Thr
    2210                2215                2220

Ala Ala Phe Gly Val Leu Leu Ser Asn Phe Gly Ala Pro Ser Tyr Cys
2225                2230                2235                2240

Asn Gly Val Arg Glu Leu Tyr Leu Asn Ser Ser Asn Val Thr Thr Met
                2245                2250                2255

Asp Phe Cys Glu Gly Ser Phe Pro Cys Ser Ile Cys Leu Ser Gly Leu
            2260                2265                2270

Asp Ser Leu Asp Ser Tyr Pro Ala Leu Glu Thr Ile Gln Val Thr Ile
        2275                2280                2285

Ser Ser Tyr Lys Leu Asp Leu Thr Ile Leu Gly Leu Ala Ala Glu Trp
    2290                2295                2300

Val Leu Ala Tyr Met Leu Phe Thr Lys Phe Phe Tyr Leu Leu Gly Leu
2305                2310                2315                2320

Ser Ala Ile Met Gln Val Phe Phe Gly Tyr Phe Ala Ser His Phe Ile
                2325                2330                2335

Ser Asn Ser Trp Leu Met Trp Phe Ile Ile Ser Ile Val Gln Met Ala
            2340                2345                2350

Pro Val Ser Ala Met Val Arg Met Tyr Ile Phe Phe Ala Ser Phe Tyr
        2355                2360                2365
```

-continued

```
Tyr Ile Trp Lys Ser Tyr Val His Ile Met Asp Gly Cys Thr Ser Ser
    2370                2375                2380

Thr Cys Met Met Cys Tyr Lys Arg Asn Arg Ala Thr Arg Val Glu Cys
2385                2390                2395                2400

Thr Thr Ile Val Asn Gly Met Lys Arg Ser Phe Tyr Val Tyr Ala Asn
                2405                2410                2415

Gly Gly Arg Gly Phe Cys Lys Thr His Asn Trp Asn Cys Leu Asn Cys
            2420                2425                2430

Asp Thr Phe Cys Thr Gly Ser Thr Phe Ile Ser Asp Glu Val Ala Arg
        2435                2440                2445

Asp Leu Ser Leu Gln Phe Lys Arg Pro Ile Asn Pro Thr Asp Gln Ser
    2450                2455                2460

Ser Tyr Ile Val Asp Ser Val Ala Val Lys Asn Gly Ala Leu His Leu
2465                2470                2475                2480

Tyr Phe Asp Lys Ala Gly Gln Lys Thr Tyr Glu Arg His Pro Leu Ser
                2485                2490                2495

His Phe Val Asn Leu Asp Asn Leu Arg Ala Asn Asn Thr Lys Gly Ser
            2500                2505                2510

Leu Pro Ile Asn Val Ile Val Phe Asp Gly Lys Ser Lys Cys Asp Glu
        2515                2520                2525

Ser Ala Ser Lys Ser Ala Ser Val Tyr Tyr Ser Gln Leu Met Cys Gln
    2530                2535                2540

Pro Ile Leu Leu Leu Asp Gln Val Leu Val Ser Asp Val Gly Asp Ser
2545                2550                2555                2560

Thr Glu Val Ser Val Lys Met Phe Asp Ala Tyr Val Asp Thr Phe Ser
                2565                2570                2575

Ala Thr Phe Ser Val Pro Met Glu Lys Leu Lys Ala Leu Val Ala Thr
            2580                2585                2590

Ala His Ser Glu Leu Ala Lys Gly Val Ala Leu Asp Gly Val Leu Ser
        2595                2600                2605

Thr Phe Val Ser Ala Ala Arg Gln Gly Val Val Asp Thr Asp Val Asp
    2610                2615                2620

Thr Lys Asp Val Ile Glu Cys Leu Lys Leu Ser His His Ser Asp Leu
2625                2630                2635                2640

Glu Val Thr Gly Asp Ser Cys Asn Asn Phe Met Leu Thr Tyr Asn Lys
                2645                2650                2655

Val Glu Asn Met Thr Pro Arg Asp Leu Gly Ala Cys Ile Asp Cys Asn
            2660                2665                2670

Ala Arg His Ile Asn Ala Gln Val Ala Lys Ser His Asn Val Ser Leu
        2675                2680                2685

Ile Trp Asn Val Lys Asp Tyr Met Ser Leu Ser Glu Gln Leu Arg Lys
    2690                2695                2700

Gln Ile Arg Ser Ala Ala Lys Lys Asn Asn Ile Pro Phe Arg Leu Thr
2705                2710                2715                2720

Cys Ala Thr Thr Arg Gln Val Val Asn Val Ile Thr Thr Lys Ile Ser
                2725                2730                2735

Leu Lys Gly Gly Lys Ile Val Ser Thr Cys Phe Lys Leu Met Leu Lys
            2740                2745                2750

Ala Thr Leu Leu Cys Val Leu Ala Ala Leu Val Cys Tyr Ile Val Met
        2755                2760                2765

Pro Val His Thr Leu Ser Ile His Asp Gly Tyr Thr Asn Glu Ile Ile
    2770                2775                2780

Gly Tyr Lys Ala Ile Gln Asp Gly Val Thr Arg Asp Ile Ile Ser Thr
```

-continued

```
2785                2790                2795                2800

Asp Asp Cys Phe Ala Asn Lys His Ala Gly Phe Asp Ala Trp Phe Ser
                2805                2810                2815

Gln Arg Gly Gly Ser Tyr Lys Asn Asp Lys Ser Cys Pro Val Val Ala
            2820                2825                2830

Ala Ile Ile Thr Arg Glu Ile Gly Phe Ile Val Pro Gly Leu Pro Gly
        2835                2840                2845

Thr Val Leu Arg Ala Ile Asn Gly Asp Phe Leu His Phe Leu Pro Arg
    2850                2855                2860

Val Phe Ser Ala Val Gly Asn Ile Cys Tyr Thr Pro Ser Lys Leu Ile
2865                2870                2875                2880

Glu Tyr Ser Asp Phe Ala Thr Ser Ala Cys Val Leu Ala Ala Glu Cys
                2885                2890                2895

Thr Ile Phe Lys Asp Ala Met Gly Lys Pro Val Pro Tyr Cys Tyr Asp
            2900                2905                2910

Thr Asn Leu Leu Glu Gly Ser Ile Ser Tyr Ser Glu Leu Arg Pro Asp
        2915                2920                2925

Thr Arg Tyr Val Leu Met Asp Gly Ser Ile Ile Gln Phe Pro Asn Thr
    2930                2935                2940

Tyr Leu Glu Gly Ser Val Arg Val Val Thr Thr Phe Asp Ala Glu Tyr
2945                2950                2955                2960

Cys Arg His Gly Thr Cys Glu Arg Ser Glu Val Gly Ile Cys Leu Ser
                2965                2970                2975

Thr Ser Gly Arg Trp Val Leu Asn Asn Glu His Tyr Arg Ala Leu Ser
            2980                2985                2990

Gly Val Phe Cys Gly Val Asp Ala Met Asn Leu Ile Ala Asn Ile Phe
        2995                3000                3005

Thr Pro Leu Val Gln Pro Val Gly Ala Leu Asp Val Ser Ala Ser Val
    3010                3015                3020

Val Ala Gly Gly Ile Ile Ala Ile Leu Val Thr Cys Ala Ala Tyr Tyr
3025                3030                3035                3040

Phe Met Lys Phe Arg Arg Val Phe Gly Glu Tyr Asn His Val Val Ala
                3045                3050                3055

Ala Asn Ala Leu Leu Phe Leu Met Ser Phe Thr Ile Leu Cys Leu Val
            3060                3065                3070

Pro Ala Tyr Ser Phe Leu Pro Gly Val Tyr Ser Val Phe Tyr Leu Tyr
        3075                3080                3085

Leu Thr Phe Tyr Phe Thr Asn Asp Val Ser Phe Leu Ala His Leu Gln
    3090                3095                3100

Trp Phe Ala Met Phe Ser Pro Ile Val Pro Phe Trp Ile Thr Ala Ile
3105                3110                3115                3120

Tyr Val Phe Cys Ile Ser Leu Lys His Cys His Trp Phe Phe Asn Asn
                3125                3130                3135

Tyr Leu Arg Lys Arg Val Met Phe Asn Gly Val Thr Phe Ser Thr Phe
            3140                3145                3150

Glu Glu Ala Ala Leu Cys Thr Phe Leu Leu Asn Lys Glu Met Tyr Leu
        3155                3160                3165

Lys Leu Arg Ser Glu Thr Leu Leu Pro Leu Thr Gln Tyr Asn Arg Tyr
    3170                3175                3180

Leu Ala Leu Tyr Asn Lys Tyr Lys Tyr Phe Ser Gly Ala Leu Asp Thr
3185                3190                3195                3200

Thr Ser Tyr Arg Glu Ala Ala Cys Cys His Leu Ala Lys Ala Leu Asn
                3205                3210                3215
```

-continued

```
Asp Phe Ser Asn Ser Gly Ala Asp Val Leu Tyr Gln Pro Pro Gln Thr
            3220                3225                3230

Ser Ile Thr Ser Ala Val Leu Gln Ser Gly Phe Arg Lys Met Ala Phe
        3235                3240                3245

Pro Ser Gly Lys Val Glu Gly Cys Met Val Gln Val Thr Cys Gly Thr
    3250                3255                3260

Thr Thr Leu Asn Gly Leu Trp Leu Asp Asp Thr Val Tyr Cys Pro Arg
3265                3270                3275                3280

His Val Ile Cys Thr Ala Glu Asp Met Leu Asn Pro Asn Tyr Glu Asp
                3285                3290                3295

Leu Leu Ile Arg Lys Ser Asn His Ser Phe Leu Val Gln Ala Gly Asn
            3300                3305                3310

Val Gln Leu Arg Val Ile Gly His Ser Met Gln Asn Cys Leu Leu Arg
        3315                3320                3325

Leu Lys Val Asp Thr Ser Asn Pro Lys Thr Pro Lys Tyr Lys Phe Val
    3330                3335                3340

Arg Ile Gln Pro Gly Gln Thr Phe Ser Val Leu Ala Cys Tyr Asn Gly
3345                3350                3355                3360

Ser Pro Ser Gly Val Tyr Gln Cys Ala Met Arg Pro Asn His Thr Ile
                3365                3370                3375

Lys Gly Ser Phe Leu Asn Gly Ser Cys Gly Ser Val Gly Phe Asn Ile
            3380                3385                3390

Asp Tyr Asp Cys Val Ser Phe Cys Tyr Met His His Met Glu Leu Pro
        3395                3400                3405

Thr Gly Val His Ala Gly Thr Asp Leu Glu Gly Lys Phe Tyr Gly Pro
    3410                3415                3420

Phe Val Asp Arg Gln Thr Ala Gln Ala Ala Gly Thr Asp Thr Thr Ile
3425                3430                3435                3440

Thr Leu Asn Val Leu Ala Trp Leu Tyr Ala Ala Val Ile Asn Gly Asp
                3445                3450                3455

Arg Trp Phe Leu Asn Arg Phe Thr Thr Thr Leu Asn Asp Phe Asn Leu
            3460                3465                3470

Val Ala Met Lys Tyr Asn Tyr Glu Pro Leu Thr Gln Asp His Val Asp
        3475                3480                3485

Ile Leu Gly Pro Leu Ser Ala Gln Thr Gly Ile Ala Val Leu Asp Met
    3490                3495                3500

Cys Ala Ala Leu Lys Glu Leu Leu Gln Asn Gly Met Asn Gly Arg Thr
3505                3510                3515                3520

Ile Leu Gly Ser Thr Ile Leu Glu Asp Glu Phe Thr Pro Phe Asp Val
                3525                3530                3535

Val Arg Gln Cys Ser Gly Val Thr Phe Gln Gly Lys Phe Lys Lys Ile
            3540                3545                3550

Val Lys Gly Thr His His Trp Met Leu Leu Thr Phe Leu Thr Ser Leu
        3555                3560                3565

Leu Ile Leu Val Gln Ser Thr Gln Trp Ser Leu Phe Phe Phe Val Tyr
    3570                3575                3580

Glu Asn Ala Phe Leu Pro Phe Thr Leu Gly Ile Met Ala Ile Ala Ala
3585                3590                3595                3600

Cys Ala Met Leu Leu Val Lys His Lys His Ala Phe Leu Cys Leu Phe
                3605                3610                3615

Leu Leu Pro Ser Leu Ala Thr Val Ala Tyr Phe Asn Met Val Tyr Met
            3620                3625                3630
```

-continued

```
Pro Ala Ser Trp Val Met Arg Ile Met Thr Trp Leu Glu Leu Ala Asp
        3635                3640                3645

Thr Ser Leu Ser Gly Tyr Arg Leu Lys Asp Cys Val Met Tyr Ala Ser
    3650                3655                3660

Ala Leu Val Leu Leu Ile Leu Met Thr Ala Arg Thr Val Tyr Asp Asp
3665                3670                3675                3680

Ala Ala Arg Arg Val Trp Thr Leu Met Asn Val Ile Thr Leu Val Tyr
                3685                3690                3695

Lys Val Tyr Tyr Gly Asn Ala Leu Asp Gln Ala Ile Ser Met Trp Ala
            3700                3705                3710

Leu Val Ile Ser Val Thr Ser Asn Tyr Ser Gly Val Val Thr Thr Ile
        3715                3720                3725

Met Phe Leu Ala Arg Ala Ile Val Phe Val Cys Val Glu Tyr Tyr Pro
    3730                3735                3740

Leu Leu Phe Ile Thr Gly Asn Thr Leu Gln Cys Ile Met Leu Val Tyr
3745                3750                3755                3760

Cys Phe Leu Gly Tyr Cys Cys Cys Cys Tyr Phe Gly Leu Phe Cys Leu
                3765                3770                3775

Leu Asn Arg Tyr Phe Arg Leu Thr Leu Gly Val Tyr Asp Tyr Leu Val
            3780                3785                3790

Ser Thr Gln Glu Phe Arg Tyr Met Asn Ser Gln Gly Leu Leu Pro Pro
        3795                3800                3805

Lys Ser Ser Ile Asp Ala Phe Lys Leu Asn Ile Lys Leu Leu Gly Ile
    3810                3815                3820

Gly Gly Lys Pro Cys Ile Lys Val Ala Thr Val Gln Ser Lys Met Ser
3825                3830                3835                3840

Asp Val Lys Cys Thr Ser Val Val Leu Leu Ser Val Leu Gln Gln Leu
                3845                3850                3855

Arg Val Glu Ser Ser Ser Lys Leu Trp Ala Gln Cys Val Gln Leu His
            3860                3865                3870

Asn Asp Ile Leu Leu Ala Lys Asp Thr Thr Glu Ala Phe Glu Lys Met
        3875                3880                3885

Val Ser Leu Leu Ser Val Leu Leu Ser Met Gln Gly Ala Val Asp Ile
    3890                3895                3900

Asn Arg Leu Cys Glu Glu Met Leu Asp Asn Arg Ala Thr Leu Gln Ala
3905                3910                3915                3920

Ile Ala Ser Glu Phe Ser Ser Leu Pro Ser Tyr Ala Ala Tyr Ala Thr
                3925                3930                3935

Ala Gln Glu Ala Tyr Glu Gln Ala Val Ala Asn Gly Asp Ser Glu Val
            3940                3945                3950

Val Leu Lys Lys Leu Lys Lys Ser Leu Asn Val Ala Lys Ser Glu Phe
        3955                3960                3965

Asp Arg Asp Ala Ala Met Gln Arg Lys Leu Glu Lys Met Ala Asp Gln
    3970                3975                3980

Ala Met Thr Gln Met Tyr Lys Gln Ala Arg Ser Glu Asp Lys Arg Ala
3985                3990                3995                4000

Lys Val Thr Ser Ala Met Gln Thr Met Leu Phe Thr Met Leu Arg Lys
                4005                4010                4015

Leu Asp Asn Asp Ala Leu Asn Asn Ile Ile Asn Asn Ala Arg Asp Gly
            4020                4025                4030

Cys Val Pro Leu Asn Ile Ile Pro Leu Thr Thr Ala Ala Lys Leu Met
        4035                4040                4045

Val Val Val Pro Asp Tyr Gly Thr Tyr Lys Asn Thr Cys Asp Gly Asn
```

-continued

```
    4050                4055                4060

Thr Phe Thr Tyr Ala Ser Ala Leu Trp Glu Ile Gln Gln Val Val Asp
4065                4070                4075                4080

Ala Asp Ser Lys Ile Val Gln Leu Ser Glu Ile Asn Met Asp Asn Ser
                4085                4090                4095

Pro Asn Leu Ala Trp Pro Leu Ile Val Thr Ala Leu Arg Ala Asn Ser
            4100                4105                4110

Ala Val Lys Leu Gln Asn Asn Glu Leu Ser Pro Val Ala Leu Arg Gln
        4115                4120                4125

Met Ser Cys Ala Ala Gly Thr Thr Gln Thr Ala Cys Thr Asp Asp Asn
    4130                4135                4140

Ala Leu Ala Tyr Tyr Asn Asn Ser Lys Gly Gly Arg Phe Val Leu Ala
4145                4150                4155                4160

Leu Leu Ser Asp His Gln Asp Leu Lys Trp Ala Arg Phe Pro Lys Ser
                4165                4170                4175

Asp Gly Thr Gly Thr Ile Tyr Thr Glu Leu Glu Pro Pro Cys Arg Phe
            4180                4185                4190

Val Thr Asp Thr Pro Lys Gly Pro Lys Val Lys Tyr Leu Tyr Phe Ile
        4195                4200                4205

Lys Gly Leu Asn Asn Leu Asn Arg Gly Met Val Leu Gly Ser Leu Ala
    4210                4215                4220

Ala Thr Val Arg Leu Gln Ala Gly Asn Ala Thr Glu Val Pro Ala Asn
4225                4230                4235                4240

Ser Thr Val Leu Ser Phe Cys Ala Phe Ala Val Asp Pro Ala Lys Ala
                4245                4250                4255

Tyr Lys Asp Tyr Leu Ala Ser Gly Gly Gln Pro Ile Thr Asn Cys Val
            4260                4265                4270

Lys Met Leu Cys Thr His Thr Gly Thr Gly Gln Ala Ile Thr Val Thr
        4275                4280                4285

Pro Glu Ala Asn Met Asp Gln Glu Ser Phe Gly Gly Ala Ser Cys Cys
    4290                4295                4300

Leu Tyr Cys Arg Cys His Ile Asp His Pro Asn Pro Lys Gly Phe Cys
4305                4310                4315                4320

Asp Leu Lys Gly Lys Tyr Val Gln Ile Pro Thr Thr Cys Ala Asn Asp
                4325                4330                4335

Pro Val Gly Phe Thr Leu Arg Asn Thr Val Cys Thr Val Cys Gly Met
            4340                4345                4350

Trp Lys Gly Tyr Gly Cys Ser Cys Asp Gln Leu Arg Glu Pro Leu Met
        4355                4360                4365

Gln Ser Ala Asp Ala Ser Thr Phe Leu Asn Arg Val Cys Gly Val Ser
    4370                4375                4380

Ala Ala Arg Leu Thr Pro Cys Gly Thr Gly Thr Ser Thr Asp Val Val
4385                4390                4395                4400

Tyr Arg Ala Phe Asp Ile Tyr Asn Glu Lys Val Ala Gly Phe Ala Lys
                4405                4410                4415

Phe Leu Lys Thr Asn Cys Cys Arg Phe Gln Glu Lys Asp Glu Glu Gly
            4420                4425                4430

Asn Leu Leu Asp Ser Tyr Phe Val Val Lys Arg His Thr Met Ser Asn
        4435                4440                4445

Tyr Gln His Glu Glu Thr Ile Tyr Asn Leu Val Lys Asp Cys Pro Ala
    4450                4455                4460

Val Ala Val His Asp Phe Phe Lys Phe Arg Val Asp Gly Asp Met Val
4465                4470                4475                4480
```

-continued

```
Pro His Ile Ser Arg Gln Arg Leu Thr Lys Tyr Thr Met Ala Asp Leu
                4485                4490                4495

Val Tyr Ala Leu Arg His Phe Asp Glu Gly Asn Cys Asp Thr Leu Lys
            4500                4505                4510

Glu Ile Leu Val Thr Tyr Asn Cys Cys Asp Asp Asp Tyr Phe Asn Lys
        4515                4520                4525

Lys Asp Trp Tyr Asp Phe Val Glu Asn Pro Asp Ile Leu Arg Val Tyr
    4530                4535                4540

Ala Asn Leu Gly Glu Arg Val Arg Gln Ser Leu Leu Lys Thr Val Gln
4545                4550                4555                4560

Phe Cys Asp Ala Met Arg Asp Ala Gly Ile Val Gly Val Leu Thr Leu
                4565                4570                4575

Asp Asn Gln Asp Leu Asn Gly Asn Trp Tyr Asp Phe Gly Asp Phe Val
            4580                4585                4590

Gln Val Ala Pro Gly Cys Gly Val Pro Ile Val Asp Ser Tyr Tyr Ser
        4595                4600                4605

Leu Leu Met Pro Ile Leu Thr Leu Thr Arg Ala Leu Ala Ala Glu Ser
    4610                4615                4620

His Met Asp Ala Asp Leu Ala Lys Pro Leu Ile Lys Trp Asp Leu Leu
4625                4630                4635                4640

Lys Tyr Asp Phe Thr Glu Glu Arg Leu Cys Leu Phe Asp Arg Tyr Phe
                4645                4650                4655

Lys Tyr Trp Asp Gln Thr Tyr His Pro Asn Cys Ile Asn Cys Leu Asp
            4660                4665                4670

Asp Arg Cys Ile Leu His Cys Ala Asn Phe Asn Val Leu Phe Ser Thr
        4675                4680                4685

Val Phe Pro Pro Thr Ser Phe Gly Pro Leu Val Arg Lys Ile Phe Val
    4690                4695                4700

Asp Gly Val Pro Phe Val Val Ser Thr Gly Tyr His Phe Arg Glu Leu
4705                4710                4715                4720

Gly Val Val His Asn Gln Asp Val Asn Leu His Ser Ser Arg Leu Ser
                4725                4730                4735

Phe Lys Glu Leu Leu Val Tyr Ala Ala Asp Pro Ala Met His Ala Ala
            4740                4745                4750

Ser Gly Asn Leu Leu Leu Asp Lys Arg Thr Thr Cys Phe Ser Val Ala
        4755                4760                4765

Ala Leu Thr Asn Asn Val Ala Phe Gln Thr Val Lys Pro Gly Asn Phe
    4770                4775                4780

Asn Lys Asp Phe Tyr Asp Phe Ala Val Ser Lys Gly Phe Phe Lys Glu
4785                4790                4795                4800

Gly Ser Ser Val Glu Leu Lys His Phe Phe Phe Ala Gln Asp Gly Asn
                4805                4810                4815

Ala Ala Ile Ser Asp Tyr Asp Tyr Tyr Arg Tyr Asn Leu Pro Thr Met
            4820                4825                4830

Cys Asp Ile Arg Gln Leu Leu Phe Val Val Glu Val Val Asp Lys Tyr
        4835                4840                4845

Phe Asp Cys Tyr Asp Gly Gly Cys Ile Asn Ala Asn Gln Val Ile Val
    4850                4855                4860

Asn Asn Leu Asp Lys Ser Ala Gly Phe Pro Phe Asn Lys Trp Gly Lys
4865                4870                4875                4880

Ala Arg Leu Tyr Tyr Asp Ser Met Ser Tyr Glu Asp Gln Asp Ala Leu
                4885                4890                4895
```

-continued

```
Phe Ala Tyr Thr Lys Arg Asn Val Ile Pro Thr Ile Thr Gln Met Asn
            4900                4905                4910

Leu Lys Tyr Ala Ile Ser Ala Lys Asn Arg Ala Arg Thr Val Ala Gly
        4915                4920                4925

Val Ser Ile Cys Ser Thr Met Thr Asn Arg Gln Phe His Gln Lys Leu
    4930                4935                4940

Leu Lys Ser Ile Ala Ala Thr Arg Gly Ala Thr Val Val Ile Gly Thr
4945                4950                4955                4960

Ser Lys Phe Tyr Gly Gly Trp His Asn Met Leu Lys Thr Val Tyr Ser
                4965                4970                4975

Asp Val Glu Thr Pro His Leu Met Gly Trp Asp Tyr Pro Lys Cys Asp
            4980                4985                4990

Arg Ala Met Pro Asn Met Leu Arg Ile Met Ala Ser Leu Val Leu Ala
        4995                5000                5005

Arg Lys His Asn Thr Cys Cys Asn Leu Ser His Arg Phe Tyr Arg Leu
    5010                5015                5020

Ala Asn Glu Cys Ala Gln Val Leu Ser Glu Met Val Met Cys Gly Gly
5025                5030                5035                5040

Ser Leu Tyr Val Lys Pro Gly Gly Thr Ser Ser Gly Asp Ala Thr Thr
                5045                5050                5055

Ala Tyr Ala Asn Ser Val Phe Asn Ile Cys Gln Ala Val Thr Ala Asn
            5060                5065                5070

Val Asn Ala Leu Leu Ser Thr Asp Gly Asn Lys Ile Ala Asp Lys Tyr
        5075                5080                5085

Val Arg Asn Leu Gln His Arg Leu Tyr Glu Cys Leu Tyr Arg Asn Arg
    5090                5095                5100

Asp Val Asp His Glu Phe Val Asp Glu Phe Tyr Ala Tyr Leu Arg Lys
5105                5110                5115                5120

His Phe Ser Met Met Ile Leu Ser Asp Asp Ala Val Val Cys Tyr Asn
                5125                5130                5135

Ser Asn Tyr Ala Ala Gln Gly Leu Val Ala Ser Ile Lys Asn Phe Lys
            5140                5145                5150

Ala Val Leu Tyr Tyr Gln Asn Asn Val Phe Met Ser Glu Ala Lys Cys
        5155                5160                5165

Trp Thr Glu Thr Asp Leu Thr Lys Gly Pro His Glu Phe Cys Ser Gln
    5170                5175                5180

His Thr Met Leu Val Lys Gln Gly Asp Asp Tyr Val Tyr Leu Pro Tyr
5185                5190                5195                5200

Pro Asp Pro Ser Arg Ile Leu Gly Ala Gly Cys Phe Val Asp Asp Ile
                5205                5210                5215

Val Lys Thr Asp Gly Thr Leu Met Ile Glu Arg Phe Val Ser Leu Ala
            5220                5225                5230

Ile Asp Ala Tyr Pro Leu Thr Lys His Pro Asn Gln Glu Tyr Ala Asp
        5235                5240                5245

Val Phe His Leu Tyr Leu Gln Tyr Ile Arg Lys Leu His Asp Glu Leu
    5250                5255                5260

Thr Gly His Met Leu Asp Met Tyr Ser Val Met Leu Thr Asn Asp Asn
5265                5270                5275                5280

Thr Ser Arg Tyr Trp Glu Pro Glu Phe Tyr Glu Ala Met Tyr Thr Pro
                5285                5290                5295

His Thr Val Leu Gln Ala Val Gly Ala Cys Val Leu Cys Asn Ser Gln
            5300                5305                5310

Thr Ser Leu Arg Cys Gly Ala Cys Ile Arg Arg Pro Phe Leu Cys Cys
```

-continued

```
        5315                5320                5325

Lys Cys Cys Tyr Asp His Val Ile Ser Thr Ser His Lys Leu Val Leu
    5330                5335                5340

Ser Val Asn Pro Tyr Val Cys Asn Ala Pro Gly Cys Asp Val Thr Asp
5345                5350                5355                5360

Val Thr Gln Leu Tyr Leu Gly Gly Met Ser Tyr Tyr Cys Lys Ser His
                5365                5370                5375

Lys Pro Pro Ile Ser Phe Pro Leu Cys Ala Asn Gly Gln Val Phe Gly
            5380                5385                5390

Leu Tyr Lys Asn Thr Cys Val Gly Ser Asp Asn Val Thr Asp Phe Asn
        5395                5400                5405

Ala Ile Ala Thr Cys Asp Trp Thr Asn Ala Gly Asp Tyr Ile Leu Ala
    5410                5415                5420

Asn Thr Cys Thr Glu Arg Leu Lys Leu Phe Ala Ala Glu Thr Leu Lys
5425                5430                5435                5440

Ala Thr Glu Glu Thr Phe Lys Leu Ser Tyr Gly Ile Ala Thr Val Arg
                5445                5450                5455

Glu Val Leu Ser Asp Arg Glu Leu His Leu Ser Trp Glu Val Gly Lys
            5460                5465                5470

Pro Arg Pro Pro Leu Asn Arg Asn Tyr Val Phe Thr Gly Tyr Arg Val
        5475                5480                5485

Thr Lys Asn Ser Lys Val Gln Ile Gly Glu Tyr Thr Phe Glu Lys Gly
    5490                5495                5500

Asp Tyr Gly Asp Ala Val Val Tyr Arg Gly Thr Thr Thr Tyr Lys Leu
5505                5510                5515                5520

Asn Val Gly Asp Tyr Phe Val Leu Thr Ser His Thr Val Met Pro Leu
                5525                5530                5535

Ser Ala Pro Thr Leu Val Pro Gln Glu His Tyr Val Arg Ile Thr Gly
            5540                5545                5550

Leu Tyr Pro Thr Leu Asn Ile Ser Asp Glu Phe Ser Ser Asn Val Ala
        5555                5560                5565

Asn Tyr Gln Lys Val Gly Met Gln Lys Tyr Ser Thr Leu Gln Gly Pro
    5570                5575                5580

Pro Gly Thr Gly Lys Ser His Phe Ala Ile Gly Leu Ala Leu Tyr Tyr
5585                5590                5595                5600

Pro Ser Ala Arg Ile Val Tyr Thr Ala Cys Ser His Ala Ala Val Asp
                5605                5610                5615

Ala Leu Cys Glu Lys Ala Leu Lys Tyr Leu Pro Ile Asp Lys Cys Ser
            5620                5625                5630

Arg Ile Ile Pro Ala Arg Ala Arg Val Glu Cys Phe Asp Lys Phe Lys
        5635                5640                5645

Val Asn Ser Thr Leu Glu Gln Tyr Val Phe Cys Thr Val Asn Ala Leu
    5650                5655                5660

Pro Glu Thr Thr Ala Asp Ile Val Val Phe Asp Glu Ile Ser Met Ala
5665                5670                5675                5680

Thr Asn Tyr Asp Leu Ser Val Val Asn Ala Arg Leu Arg Ala Lys His
                5685                5690                5695

Tyr Val Tyr Ile Gly Asp Pro Ala Gln Leu Pro Ala Pro Arg Thr Leu
            5700                5705                5710

Leu Thr Lys Gly Thr Leu Glu Pro Glu Tyr Phe Asn Ser Val Cys Arg
        5715                5720                5725

Leu Met Lys Thr Ile Gly Pro Asp Met Phe Leu Gly Thr Cys Arg Arg
    5730                5735                5740
```

-continued

```
Cys Pro Ala Glu Ile Val Asp Thr Val Ser Ala Leu Val Tyr Asp Asn
5745                5750                5755                5760

Lys Leu Lys Ala His Lys Asp Lys Ser Ala Gln Cys Phe Lys Met Phe
                5765                5770                5775

Tyr Lys Gly Val Ile Thr His Asp Val Ser Ser Ala Ile Asn Arg Pro
            5780                5785                5790

Gln Ile Gly Val Val Arg Glu Phe Leu Thr Arg Asn Pro Ala Trp Arg
        5795                5800                5805

Lys Ala Val Phe Ile Ser Pro Tyr Asn Ser Gln Asn Ala Val Ala Ser
    5810                5815                5820

Lys Ile Leu Gly Leu Pro Thr Gln Thr Val Asp Ser Ser Gln Gly Ser
5825                5830                5835                5840

Glu Tyr Asp Tyr Val Ile Phe Thr Gln Thr Thr Glu Thr Ala His Ser
                5845                5850                5855

Cys Asn Val Asn Arg Phe Asn Val Ala Ile Thr Arg Ala Lys Ile Gly
            5860                5865                5870

Ile Leu Cys Ile Met Ser Asp Arg Asp Leu Tyr Asp Lys Leu Gln Phe
        5875                5880                5885

Thr Ser Leu Glu Ile Pro Arg Arg Asn Val Ala Thr Leu Gln Ala Glu
    5890                5895                5900

Asn Val Thr Gly Leu Phe Lys Asp Cys Ser Lys Ile Ile Thr Gly Leu
5905                5910                5915                5920

His Pro Thr Gln Ala Pro Thr His Leu Ser Val Asp Ile Lys Phe Lys
                5925                5930                5935

Thr Glu Gly Leu Cys Val Asp Ile Pro Gly Ile Pro Lys Asp Met Thr
            5940                5945                5950

Tyr Arg Arg Leu Ile Ser Met Met Gly Phe Lys Met Asn Tyr Gln Val
        5955                5960                5965

Asn Gly Tyr Pro Asn Met Phe Ile Thr Arg Glu Glu Ala Ile Arg His
    5970                5975                5980

Val Arg Ala Trp Ile Gly Phe Asp Val Glu Gly Cys His Ala Thr Arg
5985                5990                5995                6000

Asp Ala Val Gly Thr Asn Leu Pro Leu Gln Leu Gly Phe Ser Thr Gly
                6005                6010                6015

Val Asn Leu Val Ala Val Pro Thr Gly Tyr Val Asp Thr Glu Asn Asn
            6020                6025                6030

Thr Glu Phe Thr Arg Val Asn Ala Lys Pro Pro Pro Gly Asp Gln Phe
        6035                6040                6045

Lys His Leu Ile Pro Leu Met Tyr Lys Gly Leu Pro Trp Asn Val Val
    6050                6055                6060

Arg Ile Lys Ile Val Gln Met Leu Ser Asp Thr Leu Lys Gly Leu Ser
6065                6070                6075                6080

Asp Arg Val Val Phe Val Leu Trp Ala His Gly Phe Glu Leu Thr Ser
                6085                6090                6095

Met Lys Tyr Phe Val Lys Ile Gly Pro Glu Arg Thr Cys Cys Leu Cys
            6100                6105                6110

Asp Lys Arg Ala Thr Cys Phe Ser Thr Ser Ser Asp Thr Tyr Ala Cys
        6115                6120                6125

Trp Asn His Ser Val Gly Phe Asp Tyr Val Tyr Asn Pro Phe Met Ile
    6130                6135                6140

Asp Val Gln Gln Trp Gly Phe Thr Gly Asn Leu Gln Ser Asn His Asp
6145                6150                6155                6160
```

-continued

```
Gln His Cys Gln Val His Gly Asn Ala His Val Ala Ser Cys Asp Ala
                6165                6170                6175

Ile Met Thr Arg Cys Leu Ala Val His Glu Cys Phe Val Lys Arg Val
            6180                6185                6190

Asp Trp Ser Val Glu Tyr Pro Ile Ile Gly Asp Glu Leu Arg Val Asn
        6195                6200                6205

Ser Ala Cys Arg Lys Val Gln His Met Val Val Lys Ser Ala Leu Leu
    6210                6215                6220

Ala Asp Lys Phe Pro Val Leu His Asp Ile Gly Asn Pro Lys Ala Ile
6225                6230                6235                6240

Lys Cys Val Pro Gln Ala Glu Val Glu Trp Lys Phe Tyr Asp Ala Gln
                6245                6250                6255

Pro Cys Ser Asp Lys Ala Tyr Lys Ile Glu Glu Leu Phe Tyr Ser Tyr
            6260                6265                6270

Ala Thr His His Asp Lys Phe Thr Asp Gly Val Cys Leu Phe Trp Asn
        6275                6280                6285

Cys Asn Val Asp Arg Tyr Pro Ala Asn Ala Ile Val Cys Arg Phe Asp
    6290                6295                6300

Thr Arg Val Leu Ser Asn Leu Asn Leu Pro Gly Cys Asp Gly Gly Ser
6305                6310                6315                6320

Leu Tyr Val Asn Lys His Ala Phe His Thr Pro Ala Phe Asp Lys Ser
                6325                6330                6335

Ala Phe Thr Asn Leu Lys Gln Leu Pro Phe Phe Tyr Tyr Ser Asp Ser
            6340                6345                6350

Pro Cys Glu Ser His Gly Lys Gln Val Val Ser Asp Ile Asp Tyr Val
        6355                6360                6365

Pro Leu Lys Ser Ala Thr Cys Ile Thr Arg Cys Asn Leu Gly Gly Ala
    6370                6375                6380

Val Cys Arg His His Ala Asn Glu Tyr Arg Gln Tyr Leu Asp Ala Tyr
6385                6390                6395                6400

Asn Met Met Ile Ser Ala Gly Phe Ser Leu Trp Ile Tyr Lys Gln Phe
                6405                6410                6415

Asp Thr Tyr Asn Leu Trp Asn Thr Phe Thr Arg Leu Gln Ser Leu Glu
            6420                6425                6430

Asn Val Ala Tyr Asn Val Val Asn Lys Gly His Phe Asp Gly His Ala
        6435                6440                6445

Gly Glu Ala Pro Val Ser Ile Ile Asn Asn Ala Val Tyr Thr Lys Val
    6450                6455                6460

Asp Gly Ile Asp Val Glu Ile Phe Glu Asn Lys Thr Thr Leu Pro Val
6465                6470                6475                6480

Asn Val Ala Phe Glu Leu Trp Ala Lys Arg Asn Ile Lys Pro Val Pro
                6485                6490                6495

Glu Ile Lys Ile Leu Asn Asn Leu Gly Val Asp Ile Ala Ala Asn Thr
            6500                6505                6510

Val Ile Trp Asp Tyr Lys Arg Glu Ala Pro Ala His Val Ser Thr Ile
        6515                6520                6525

Gly Val Cys Thr Met Thr Asp Ile Ala Lys Lys Pro Thr Glu Ser Ala
    6530                6535                6540

Cys Ser Ser Leu Thr Val Leu Phe Asp Gly Arg Val Glu Gly Gln Val
6545                6550                6555                6560

Asp Leu Phe Arg Asn Ala Arg Asn Gly Val Leu Ile Thr Glu Gly Ser
                6565                6570                6575

Val Lys Gly Leu Thr Pro Ser Lys Gly Pro Ala Gln Ala Ser Val Asn
```

-continued

```
            6580                6585                6590

Gly Val Thr Leu Ile Gly Glu Ser Val Lys Thr Gln Phe Asn Tyr Phe
        6595                6600                6605

Lys Lys Val Asp Gly Ile Ile Gln Gln Leu Pro Glu Thr Tyr Phe Thr
    6610                6615                6620

Gln Ser Arg Asp Leu Glu Asp Phe Lys Pro Arg Ser Gln Met Glu Thr
6625                6630                6635                6640

Asp Phe Leu Glu Leu Ala Met Asp Glu Phe Ile Gln Arg Tyr Lys Leu
                6645                6650                6655

Glu Gly Tyr Ala Phe Glu His Ile Val Tyr Gly Asp Phe Ser His Gly
            6660                6665                6670

Gln Leu Gly Gly Leu His Leu Met Ile Gly Leu Ala Lys Arg Ser Gln
        6675                6680                6685

Asp Ser Pro Leu Lys Leu Glu Asp Phe Ile Pro Met Asp Ser Thr Val
    6690                6695                6700

Lys Asn Tyr Phe Ile Thr Asp Ala Gln Thr Gly Ser Ser Lys Cys Val
6705                6710                6715                6720

Cys Ser Val Ile Asp Leu Leu Leu Asp Asp Phe Val Glu Ile Ile Lys
                6725                6730                6735

Ser Gln Asp Leu Ser Val Ile Ser Lys Val Val Lys Val Thr Ile Asp
            6740                6745                6750

Tyr Ala Glu Ile Ser Phe Met Leu Trp Cys Lys Asp Gly His Val Glu
        6755                6760                6765

Thr Phe Tyr Pro Lys Leu Gln Ala Ser Gln Ala Trp Gln Pro Gly Val
    6770                6775                6780

Ala Met Pro Asn Leu Tyr Lys Met Gln Arg Met Leu Leu Glu Lys Cys
6785                6790                6795                6800

Asp Leu Gln Asn Tyr Gly Glu Asn Ala Val Ile Pro Lys Gly Ile Met
                6805                6810                6815

Met Asn Val Ala Lys Tyr Thr Gln Leu Cys Gln Tyr Leu Asn Thr Leu
            6820                6825                6830

Thr Leu Ala Val Pro Tyr Asn Met Arg Val Ile His Phe Gly Ala Gly
        6835                6840                6845

Ser Asp Lys Gly Val Ala Pro Gly Thr Ala Val Leu Arg Gln Trp Leu
    6850                6855                6860

Pro Thr Gly Thr Leu Leu Val Asp Ser Asp Leu Asn Asp Phe Val Ser
6865                6870                6875                6880

Asp Ala Asp Ser Thr Leu Ile Gly Asp Cys Ala Thr Val His Thr Ala
                6885                6890                6895

Asn Lys Trp Asp Leu Ile Ile Ser Asp Met Tyr Asp Pro Arg Thr Lys
            6900                6905                6910

His Val Thr Lys Glu Asn Asp Ser Lys Glu Gly Phe Phe Thr Tyr Leu
        6915                6920                6925

Cys Gly Phe Ile Lys Gln Lys Leu Ala Leu Gly Gly Ser Ile Ala Val
    6930                6935                6940

Lys Ile Thr Glu His Ser Trp Asn Ala Asp Leu Tyr Lys Leu Met Gly
6945                6950                6955                6960

His Phe Ser Trp Trp Thr Ala Phe Val Thr Asn Val Asn Ala Ser Ser
                6965                6970                6975

Ser Glu Ala Phe Leu Ile Gly Ala Asn Tyr Leu Gly Lys Pro Lys Glu
            6980                6985                6990

Gln Ile Asp Gly Tyr Thr Met His Ala Asn Tyr Ile Phe Trp Arg Asn
        6995                7000                7005
```

-continued

```
Thr Asn Pro Ile Gln Leu Ser Ser Tyr Ser Leu Phe Asp Met Ser Lys
    7010                7015                7020

Phe Pro Leu Lys Leu Arg Gly Thr Ala Val Met Ser Leu Lys Glu Asn
7025                7030                7035                7040

Gln Ile Asn Asp Met Ile Tyr Ser Leu Leu Glu Lys Gly Arg Leu Ile
                7045                7050                7055

Ile Arg Glu Asn Asn Arg Val Val Val Ser Ser Asp Ile Leu Val Asn
            7060                7065                7070

Asn


<210> SEQ ID NO 3
<211> LENGTH: 3768
<212> TYPE: DNA
<213> ORGANISM: SARS coronavirus Urbani

<400> SEQUENCE: 3

atgtttattt tcttattatt tcttactctc actagtggta gtgaccttga ccggtgcacc     60

acttttgatg atgttcaagc tcctaattac actcaacata cttcatctat gaggggggtt    120

tactatcctg atgaaatttt tagatcagac actctttatt taactcagga tttatttctt    180

ccattttatt ctaatgttac agggtttcat actattaatc atacgtttgg caaccctgtc    240

atacctttta aggatggtat ttattttgct gccacagaga aatcaaatgt tgtccgtggt    300

tgggtttttg gttctaccat gaacaacaag tcacagtcgg tgattattat taacaattct    360

actaatgttg ttatacgagc atgtaacttt gaattgtgtg acaacccttt ctttgctgtt    420

tctaaaccca tgggtacaca gacacatact atgatattcg ataatgcatt taattgcact    480

ttcgagtaca tatctgatgc cttttcgctt gatgtttcag aaaagtcagg taattttaaa    540

cacttacgag agtttgtgtt taaaaataaa gatgggtttc tctatgttta taagggctat    600

caacctatag atgtagttcg tgatctacct tctggtttta acactttgaa acctattttt    660

aagttgcctc ttggtattaa cattacaaat tttagagcca ttcttacagc cttttcacct    720

gctcaagaca tttggggcac gtcagctgca gcctattttg ttggctattt aaagccaact    780

acatttatgc tcaagtatga tgaaaatggt acaatcacag atgctgttga ttgttctcaa    840

aatccacttg ctgaactcaa atgctctgtt aagagctttg agattgacaa aggaatttac    900

cagacctcta atttcagggt tgttccctca ggagatgttg tgagattccc taatattaca    960

aacttgtgtc cttttggaga ggtttttaat gctactaaat tcccttctgt ctatgcatgg   1020

gagagaaaaa aaatttctaa ttgtgttgct gattactctg tgctctacaa ctcaacattt   1080

ttttcaacct ttaagtgcta tggcgtttct gccactaagt tgaatgatct ttgcttctcc   1140

aatgtctatg cagattcttt tgtagtcaag ggagatgatg taagacaaat agcgccagga   1200

caaactggtg ttattgctga ttataattat aaattgccag atgatttcat gggttgtgtc   1260

cttgcttgga atactaggaa cattgatgct acttcaactg gtaattataa ttataaatat   1320

aggtatctta gacatggcaa gcttaggccc tttgagagag acatatctaa tgtgcctttc   1380

tcccctgatg gcaaaccttg caccccacct gctcttaatt gttattggcc attaaatgat   1440

tatggttttt acaccactac tggcattggc taccaacctt acagagttgt agtactttct   1500

tttgaacttt taaatgcacc ggccacggtt tgtggaccaa aattatccac tgaccttatt   1560

aagaaccagt gtgtcaattt taattttaat ggactcactg gtactggtgt gttaactcct   1620

tcttcaaaga gatttcaacc atttcaacaa tttggccgtg atgtttctga tttcactgat   1680
```

-continued

```
tccgttcgag atcctaaaac atctgaaata ttagacattt caccttgctc ttttgggggt   1740
gtaagtgtaa ttacacctgg aacaaatgct tcatctgaag ttgctgttct atatcaagat   1800
gttaactgca ctgatgtttc tacagcaatt catgcagatc aactcacacc agcttggcgc   1860
atatattcta ctggaaacaa tgtattccag actcaagcag gctgtcttat aggagctgag   1920
catgtcgaca cttcttatga gtgcgacatt cctattggag ctggcatttg tgctagttac   1980
catacagttt ctttattacg tagtactagc caaaaatcta ttgtggctta tactatgtct   2040
ttaggtgctg atagttcaat tgcttactct aataacacca ttgctatacc tactaacttt   2100
tcaattagca ttactacaga agtaatgcct gtttctatgg ctaaaacctc cgtagattgt   2160
aatatgtaca tctgcggaga ttctactgaa tgtgctaatt tgcttctcca atatggtagc   2220
ttttgcacac aactaaatcg tgcactctca ggtattgctg ctgaacagga tcgcaacaca   2280
cgtgaagtgt tcgctcaagt caaacaaatg tacaaaaccc caactttgaa atattttggt   2340
ggttttaatt tttcacaaat attacctgac cctctaaagc caactaagag gtcttttatt   2400
gaggacttgc tctttaataa ggtgacactc gctgatgctg gcttcatgaa gcaatatggc   2460
gaatgcctag gtgatattaa tgctagagat ctcatttgtg cgcagaagtt caatggactt   2520
acagtgttgc cacctctgct cactgatgat atgattgctg cctacactgc tgctctagtt   2580
agtggtactg ccactgctgg atggacattt ggtgctggcg ctgctcttca aatacctttt   2640
gctatgcaaa tggcatatag gttcaatggc attggagtta cccaaaatgt tctctatgag   2700
aaccaaaaac aaatcgccaa ccaatttaac aaggcgatta gtcaaattca agaatcactt   2760
acaacaacat caactgcatt gggcaagctg caagacgttg ttaaccagaa tgctcaagca   2820
ttaaacacac ttgttaaaca acttagctct aattttggtg caatttcaag tgtgctaaat   2880
gatatccttt cgcgacttga taaagtcgag gcggaggtac aaattgacag gttaattaca   2940
ggcagacttc aaagccttca aacctatgta acacaacaac taatcagggc tgctgaaatc   3000
agggcttctg ctaatcttgc tgctactaaa atgtctgagt gtgttcttgg acaatcaaaa   3060
agagttgact tttgtggaaa gggctaccac cttatgtcct tcccacaagc agccccgcat   3120
ggtgttgtct tcctacatgt cacgtatgtg ccatcccagg agaggaactt caccacagcg   3180
ccagcaattt gtcatgaagg caaagcatac ttccctcgtg aaggtgtttt tgtgtttaat   3240
ggcacttctt ggtttattac acagaggaac ttcttttctc cacaaataat tactacagac   3300
aatacatttg tctcaggaaa ttgtgatgtc gttattggca tcattaacaa cacagtttat   3360
gatcctctgc aacctgagct cgactcattc aaagaagagc tggacaagta cttcaaaaat   3420
catacatcac cagatgttga tcttggcgac atttcaggca ttaacgcttc tgtcgtcaac   3480
attcaaaaag aaattgaccg cctcaatgag gtcgctaaaa atttaaatga atcactcatt   3540
gaccttcaag aattgggaaa atatgagcaa tatattaaat ggccttggta tgtttggctc   3600
ggcttcattg ctggactaat tgccatcgtc atggttacaa tcttgctttg ttgcatgact   3660
agttgttgca gttgcctcaa gggtgcatgc tcttgtggtt cttgctgcaa gtttgatgag   3720
gatgactctg agccagttct caagggtgtc aaattacatt acacataa                 3768
```

<210> SEQ ID NO 4
<211> LENGTH: 1255
<212> TYPE: PRT
<213> ORGANISM: SARS coronavirus Urbani

<400> SEQUENCE: 4

Met Phe Ile Phe Leu Leu Phe Leu Thr Leu Thr Ser Gly Ser Asp Leu

-continued

```
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430
```

-continued

```
Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ala Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845
```

-continued

```
Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile Arg Ala Ser Ala Asn Leu Ala Ala
        995                 1000                1005

Thr Lys Met Ser Glu Cys Val Leu Gly Gln Ser Lys Arg Val Asp Phe
    1010                1015                1020

Cys Gly Lys Gly Tyr His Leu Met Ser Phe Pro Gln Ala Ala Pro His
1025                1030                1035                1040

Gly Val Val Phe Leu His Val Thr Tyr Val Pro Ser Gln Glu Arg Asn
                1045                1050                1055

Phe Thr Thr Ala Pro Ala Ile Cys His Glu Gly Lys Ala Tyr Phe Pro
            1060                1065                1070

Arg Glu Gly Val Phe Val Phe Asn Gly Thr Ser Trp Phe Ile Thr Gln
        1075                1080                1085

Arg Asn Phe Phe Ser Pro Gln Ile Ile Thr Thr Asp Asn Thr Phe Val
    1090                1095                1100

Ser Gly Asn Cys Asp Val Val Ile Gly Ile Ile Asn Asn Thr Val Tyr
1105                1110                1115                1120

Asp Pro Leu Gln Pro Glu Leu Asp Ser Phe Lys Glu Glu Leu Asp Lys
                1125                1130                1135

Tyr Phe Lys Asn His Thr Ser Pro Asp Val Asp Leu Gly Asp Ile Ser
            1140                1145                1150

Gly Ile Asn Ala Ser Val Val Asn Ile Gln Lys Glu Ile Asp Arg Leu
        1155                1160                1165

Asn Glu Val Ala Lys Asn Leu Asn Glu Ser Leu Ile Asp Leu Gln Glu
    1170                1175                1180

Leu Gly Lys Tyr Glu Gln Tyr Ile Lys Trp Pro Trp Tyr Val Trp Leu
1185                1190                1195                1200

Gly Phe Ile Ala Gly Leu Ile Ala Ile Val Met Val Thr Ile Leu Leu
                1205                1210                1215

Cys Cys Met Thr Ser Cys Cys Ser Cys Leu Lys Gly Ala Cys Ser Cys
            1220                1225                1230

Gly Ser Cys Cys Lys Phe Asp Glu Asp Asp Ser Glu Pro Val Leu Lys
        1235                1240                1245

Gly Val Lys Leu His Tyr Thr
    1250                1255
```

-continued

```
<210> SEQ ID NO 5
<211> LENGTH: 444
<212> TYPE: DNA
<213> ORGANISM: SARS coronavirus Urbani
<220> FEATURE:
<221> NAME/KEY: CDS
<222> LOCATION: (1)...(444)

<400> SEQUENCE: 5

gtc ata cct ttt aag gat ggt att tat ttt gct gcc aca gag aaa tca       48
Val Ile Pro Phe Lys Asp Gly Ile Tyr Phe Ala Ala Thr Glu Lys Ser
 1               5                  10                  15

aat gtt gtc cgt ggt tgg gtt ttt ggt tct acc atg aac aac aag tca       96
Asn Val Val Arg Gly Trp Val Phe Gly Ser Thr Met Asn Asn Lys Ser
            20                  25                  30

cag tcg gtg att att att aac aat tct act aat gtt gtt ata cga gca      144
Gln Ser Val Ile Ile Ile Asn Asn Ser Thr Asn Val Val Ile Arg Ala
        35                  40                  45

tgt aac ttt gaa ttg tgt gac aac cct ttc ttt gct gtt tct aaa ccc      192
Cys Asn Phe Glu Leu Cys Asp Asn Pro Phe Phe Ala Val Ser Lys Pro
    50                  55                  60

atg ggt aca cag aca cat act atg ata ttc gat aat gca ttt aat tgc      240
Met Gly Thr Gln Thr His Thr Met Ile Phe Asp Asn Ala Phe Asn Cys
 65                  70                  75                  80

act ttc gag tac ata tct gat gcc ttt tcg ctt gat gtt tca gaa aag      288
Thr Phe Glu Tyr Ile Ser Asp Ala Phe Ser Leu Asp Val Ser Glu Lys
                85                  90                  95

tca ggt aat ttt aaa cac tta cga gag ttt gtg ttt aaa aat aaa gat      336
Ser Gly Asn Phe Lys His Leu Arg Glu Phe Val Phe Lys Asn Lys Asp
            100                 105                 110

ggg ttt ctc tat gtt tat aag ggc tat caa cct ata gat gta gtt cgt      384
Gly Phe Leu Tyr Val Tyr Lys Gly Tyr Gln Pro Ile Asp Val Val Arg
        115                 120                 125

gat cta cct tct ggt ttt aac act ttg aaa cct att ttt aag ttg cct      432
Asp Leu Pro Ser Gly Phe Asn Thr Leu Lys Pro Ile Phe Lys Leu Pro
    130                 135                 140

ctt ggt att aac                                                      444
Leu Gly Ile Asn
145


<210> SEQ ID NO 6
<211> LENGTH: 148
<212> TYPE: PRT
<213> ORGANISM: SARS coronavirus Urbani

<400> SEQUENCE: 6

Val Ile Pro Phe Lys Asp Gly Ile Tyr Phe Ala Ala Thr Glu Lys Ser
 1               5                  10                  15

Asn Val Val Arg Gly Trp Val Phe Gly Ser Thr Met Asn Asn Lys Ser
            20                  25                  30

Gln Ser Val Ile Ile Ile Asn Asn Ser Thr Asn Val Val Ile Arg Ala
        35                  40                  45

Cys Asn Phe Glu Leu Cys Asp Asn Pro Phe Phe Ala Val Ser Lys Pro
    50                  55                  60

Met Gly Thr Gln Thr His Thr Met Ile Phe Asp Asn Ala Phe Asn Cys
65                  70                  75                  80

Thr Phe Glu Tyr Ile Ser Asp Ala Phe Ser Leu Asp Val Ser Glu Lys
                85                  90                  95

Ser Gly Asn Phe Lys His Leu Arg Glu Phe Val Phe Lys Asn Lys Asp
            100                 105                 110
```

-continued

```
Gly Phe Leu Tyr Val Tyr Lys Gly Tyr Gln Pro Ile Asp Val Val Arg
        115                 120                 125

Asp Leu Pro Ser Gly Phe Asn Thr Leu Lys Pro Ile Phe Lys Leu Pro
    130                 135                 140

Leu Gly Ile Asn
145


<210> SEQ ID NO 7
<211> LENGTH: 1356
<212> TYPE: DNA
<213> ORGANISM: SARS coronavirus Urbani

<400> SEQUENCE: 7

gctgaactca aatgctctgt taagagcttt gagattgaca aaggaattta ccagacctct      60

aatttcaggg ttgttccctc aggagatgtt gtgagattcc ctaatattac aaacttgtgt     120

ccttttggag aggtttttaa tgctactaaa ttcccttctg tctatgcatg ggagagaaaa     180

aaaatttcta attgtgttgc tgattactct gtgctctaca actcaacatt tttttcaacc     240

tttaagtgct atggcgtttc tgccactaag ttgaatgatc tttgcttctc caatgtctat     300

gcagattctt ttgtagtcaa gggagatgat gtaagacaaa tagcgccagg acaaactggt     360

gttattgctg attataatta taaattgcca gatgatttca tgggttgtgt ccttgcttgg     420

aatactagga acattgatgc tacttcaact ggtaattata attataaata taggtatctt     480

agacatggca agcttaggcc ctttgagaga gacatatcta atgtgccttt ctcccctgat     540

ggcaaacctt gcaccccacc tgctcttaat tgttattggc cattaaatga ttatggtttt     600

tacaccacta ctggcattgg ctaccaacct tacagagttg tagtactttc ttttgaactt     660

ttaaatgcac cggccacggt ttgtggacca aaattatcca ctgaccttat taagaaccag     720

tgtgtcaatt ttaattttaa tggactcact ggtactggtg tgttaactcc ttcttcaaag     780

agatttcaac catttcaaca atttggccgt gatgtttctg atttcactga ttccgttcga     840

gatcctaaaa catctgaaat attagacatt tcaccttgct cttttggggg tgtaagtgta     900

attacacctg gaacaaatgc ttcatctgaa gttgctgttc tatatcaaga tgttaactgc     960

actgatgttt ctacagcaat tcatgcagat caactcacac cagcttggcg catatattct    1020

actggaaaca atgtattcca gactcaagca ggctgtctta taggagctga gcatgtcgac    1080

acttcttatg agtgcgacat tcctattgga gctggcattt gtgctagtta ccatacagtt    1140

tctttattac gtagtactag ccaaaaatct attgtggctt atactatgtc tttaggtgct    1200

gatagttcaa ttgcttactc taataacacc attgctatac ctactaactt ttcaattagc    1260

attactacag aagtaatgcc tgtttctatg gctaaaacct ccgtagattg taatatgtac    1320

atctgcggag attctactga atgtgctaat ttgctt                               1356


<210> SEQ ID NO 8
<211> LENGTH: 452
<212> TYPE: PRT
<213> ORGANISM: SARS coronavirus Urbani

<400> SEQUENCE: 8

Ala Glu Leu Lys Cys Ser Val Lys Ser Phe Glu Ile Asp Lys Gly Ile
 1               5                  10                  15

Tyr Gln Thr Ser Asn Phe Arg Val Val Pro Ser Gly Asp Val Val Arg
            20                  25                  30

Phe Pro Asn Ile Thr Asn Leu Cys Pro Phe Gly Glu Val Phe Asn Ala
        35                  40                  45
```

-continued

```
Thr Lys Phe Pro Ser Val Tyr Ala Trp Glu Arg Lys Lys Ile Ser Asn
    50                  55                  60

Cys Val Ala Asp Tyr Ser Val Leu Tyr Asn Ser Thr Phe Phe Ser Thr
65                  70                  75                  80

Phe Lys Cys Tyr Gly Val Ser Ala Thr Lys Leu Asn Asp Leu Cys Phe
                85                  90                  95

Ser Asn Val Tyr Ala Asp Ser Phe Val Val Lys Gly Asp Asp Val Arg
            100                 105                 110

Gln Ile Ala Pro Gly Gln Thr Gly Val Ile Ala Asp Tyr Asn Tyr Lys
        115                 120                 125

Leu Pro Asp Asp Phe Met Gly Cys Val Leu Ala Trp Asn Thr Arg Asn
    130                 135                 140

Ile Asp Ala Thr Ser Thr Gly Asn Tyr Asn Tyr Lys Tyr Arg Tyr Leu
145                 150                 155                 160

Arg His Gly Lys Leu Arg Pro Phe Glu Arg Asp Ile Ser Asn Val Pro
                165                 170                 175

Phe Ser Pro Asp Gly Lys Pro Cys Thr Pro Pro Ala Leu Asn Cys Tyr
            180                 185                 190

Trp Pro Leu Asn Asp Tyr Gly Phe Tyr Thr Thr Thr Gly Ile Gly Tyr
        195                 200                 205

Gln Pro Tyr Arg Val Val Val Leu Ser Phe Glu Leu Leu Asn Ala Pro
    210                 215                 220

Ala Thr Val Cys Gly Pro Lys Leu Ser Thr Asp Leu Ile Lys Asn Gln
225                 230                 235                 240

Cys Val Asn Phe Asn Phe Asn Gly Leu Thr Gly Thr Gly Val Leu Thr
                245                 250                 255

Pro Ser Ser Lys Arg Phe Gln Pro Phe Gln Gln Phe Gly Arg Asp Val
            260                 265                 270

Ser Asp Phe Thr Asp Ser Val Arg Asp Pro Lys Thr Ser Glu Ile Leu
        275                 280                 285

Asp Ile Ser Pro Cys Ala Phe Gly Gly Val Ser Val Ile Thr Pro Gly
    290                 295                 300

Thr Asn Ala Ser Ser Glu Val Ala Val Leu Tyr Gln Asp Val Asn Cys
305                 310                 315                 320

Thr Asp Val Ser Thr Ala Ile His Ala Asp Gln Leu Thr Pro Ala Trp
                325                 330                 335

Arg Ile Tyr Ser Thr Gly Asn Asn Val Phe Gln Thr Gln Ala Gly Cys
            340                 345                 350

Leu Ile Gly Ala Glu His Val Asp Thr Ser Tyr Glu Cys Asp Ile Pro
        355                 360                 365

Ile Gly Ala Gly Ile Cys Ala Ser Tyr His Thr Val Ser Leu Leu Arg
    370                 375                 380

Ser Thr Ser Gln Lys Ser Ile Val Ala Tyr Thr Met Ser Leu Gly Ala
385                 390                 395                 400

Asp Ser Ser Ile Ala Tyr Ser Asn Asn Thr Ile Ala Ile Pro Thr Asn
                405                 410                 415

Phe Ser Ile Ser Ile Thr Thr Glu Val Met Pro Val Ser Met Ala Lys
            420                 425                 430

Thr Ser Val Asp Cys Asn Met Tyr Ile Cys Gly Asp Ser Thr Glu Cys
        435                 440                 445

Ala Asn Leu Leu
    450
```

-continued

```
<210> SEQ ID NO 9
<211> LENGTH: 891
<212> TYPE: DNA
<213> ORGANISM: Artificial Sequence
<220> FEATURE:
<223> OTHER INFORMATION: Synthetically generated oligonucleotide

<400> SEQUENCE: 9

cat acg ttt ggc aac cct gtc ata cct ttt aag gat ggt att tat ttt       48

gct gcc aca gag aaa tca aat gtt gtc cgt ggt tgg gtt ttt ggt tct       96

acc atg aac aac aag tca cag tcg gtg att att att aac aat tct act      144

aat gtt gtt ata cga gca tgt aac ttt gaa ttg tgt gac aac cct ttc      192

ttt gct gtt tct aaa ccc atg ggt aca cag aca cat act atg ata ttc      240

gat aat gca ttt aat tgc act ttc gag tac ata tct gat gcc ttt tcg      288

ctt gat gtt tca gaa aag tca ggt aat ttt aaa cac tta cga gag ttt      336

gtg ttt aaa aat aaa gat ggg ttt ctc tat gtt tat aag ggc tat caa      384

cct ata gat gta gtt cgt gat cta cct tct ggt ttt aac act ttg aaa      432

cct att ttt aag ttg cct ctt ggt att aac att aca aat ttt aga gcc      480

gaa ttc ggg ggc ggg ggt gga ggt ggt ggc tca ttc aaa gaa gag ctg      528

gac aag tac ttc aaa aat cat aca tca cca gat gtt gat ctt ggc gac      576

att tca ggc att aac gct tct gtc gtc aac att caa aaa gaa att gac      624

cgc ctc aat gag gtc gct aaa aat tta aat gaa tca ctc att gac ctt      672

caa gaa ttg gga aaa tat gag caa tat att aaa tgg cct tgg tat gtt      720

tgg ctc ggc ttc att gct gga cta att gcc atc gtc atg gtt aca atc      768

ttg ctt tgt tgc atg act agt tgt tgc agt tgc ctc aag ggt gca tgc      816

tct tgt ggt tct tgc tgc aag ttt gat gag gat gac tct gag cca gtt      864

ctc aag ggt gtc aaa tta cat tac aca                                  891


<210> SEQ ID NO 10
<211> LENGTH: 284
<212> TYPE: PRT
<213> ORGANISM: Artificial Sequence
<220> FEATURE:
<223> OTHER INFORMATION: Synthetically generated peptide

<400> SEQUENCE: 10

Val Ile Pro Phe Lys Asp Gly Ile Tyr Phe Ala Ala Thr Glu Lys Ser
 1               5                  10                  15

Asn Val Val Arg Gly Trp Val Phe Gly Ser Thr Met Asn Asn Lys Ser
            20                  25                  30

Gln Ser Val Ile Ile Ile Asn Asn Ser Thr Asn Val Val Ile Arg Ala
        35                  40                  45

Cys Asn Phe Glu Leu Cys Asp Asn Pro Phe Phe Ala Val Ser Lys Pro
    50                  55                  60

Met Gly Thr Gln Thr His Thr Met Ile Phe Asp Asn Ala Phe Asn Cys
65                  70                  75                  80

Thr Phe Glu Tyr Ile Ser Asp Ala Phe Ser Leu Asp Val Ser Glu Lys
                85                  90                  95

Ser Gly Asn Phe Lys His Leu Arg Glu Phe Val Phe Lys Asn Lys Asp
            100                 105                 110
```

-continued

```
Gly Phe Leu Tyr Val Tyr Lys Gly Tyr Gln Pro Ile Asp Val Val Arg
        115                 120                 125

Asp Leu Pro Ser Gly Phe Asn Thr Leu Lys Pro Ile Phe Lys Leu Pro
    130                 135                 140

Leu Gly Ile Asn Gly Gly Gly Gly Gly Gly Gly Gly Asp Ser Phe Lys
145                 150                 155                 160

Glu Glu Leu Asp Lys Tyr Phe Lys Asn His Thr Ser Pro Asp Val Asp
                165                 170                 175

Leu Gly Asp Ile Ser Gly Ile Asn Ala Ser Val Val Asn Ile Gln Lys
            180                 185                 190

Glu Ile Asp Arg Leu Asn Glu Val Ala Lys Asn Leu Asn Glu Ser Leu
        195                 200                 205

Ile Asp Leu Gln Glu Leu Gly Lys Tyr Glu Gln Tyr Ile Lys Trp Pro
    210                 215                 220

Trp Tyr Val Trp Leu Gly Phe Ile Ala Gly Leu Ile Ala Ile Val Met
225                 230                 235                 240

Val Thr Ile Leu Leu Cys Cys Met Thr Ser Cys Cys Ser Cys Leu Lys
                245                 250                 255

Gly Ala Cys Ser Cys Gly Ser Cys Cys Lys Phe Asp Glu Asp Asp Ser
            260                 265                 270

Glu Pro Val Leu Lys Gly Val Lys Leu His Tyr Thr
        275                 280
```

<210> SEQ ID NO 11
<211> LENGTH: 1752
<212> TYPE: DNA
<213> ORGANISM: Artificial Sequence
<220> FEATURE:
<223> OTHER INFORMATION: Synthetically generated oligonucleotide

<400> SEQUENCE: 11

```
gagattgaca aaggaattta ccagacctct aatttcaggg ttgttccctc aggagatgtt     60

gtgagattcc ctaatattac aaacttgtgt ccttttggag aggtttttaa tgctactaaa    120

ttcccttctg tctatgcatg ggagagaaaa aaaatttcta attgtgttgc tgattactct    180

gtgctctaca actcaacatt tttttcaacc tttaagtgct atggcgtttc tgccactaag    240

ttgaatgatc tttgcttctc caatgtctat gcagattctt ttgtagtcaa gggagatgat    300

gtaagacaaa tagcgccagg acaaactggt gttattgctg attataatta taaattgcca    360

gatgatttca tgggttgtgt ccttgcttgg aatactagga acattgatgc tacttcaact    420

ggtaattata attataaata taggtatctt agacatggca agcttaggcc ctttgagaga    480

gacatatcta atgtgccttt ctcccctgat ggcaaacctt gcaccccacc tgctcttaat    540

tgttattggc cattaaatga ttatggtttt tacaccacta ctggcattgg ctaccaacct    600

tacagagttg tagtactttc ttttgaactt ttaaatgcac cggccacggt ttgtggacca    660

aaattatcca ctgaccttat taagaaccag tgtgtcaatt ttaattttaa tggactcact    720

ggtactggtg tgttaactcc ttcttcaaag agatttcaac catttcaaca atttggccgt    780

gatgtttctg atttcactga ttccgttcga gatcctaaaa catctgaaat attagacatt    840

tcaccttgct cttttggggg tgtaagtgta attacacctg gaacaaatgc ttcatctgaa    900

gttgctgttc tatatcaaga tgttaactgc actgatgttt ctacagcaat tcatgcagat    960

caactcacac cagcttggcg catatattct actggaaaca atgtattcca gactcaagca   1020

ggctgtctta taggagctga gcatgtcgac acttcttatg agtgcgacat tcctattgga   1080
```

-continued

```
gctggcattt gtgctagtta ccatacagtt tctttattac gtagtactag ccaaaaatct   1140

attgtggctt atactatgtc tttaggtgct gatagttcaa ttgcttactc taataacacc   1200

attgctatac ctactaactt ttcaattagc attactacag aagtaatgcc tgtttctatg   1260

gctaaaacct ccgtagattg taatatgtac atctgcggag attctactga atgtgctaat   1320

ttgcttctcc aatatgggcg gccgcctggg ggcgggggtg gaggtggtgg ctcattcaaa   1380

gaagagctgg acaagtactt caaaaatcat acatcaccag atgttgatct tggcgacatt   1440

tcaggcatta acgcttctgt cgtcaacatt caaaaagaaa ttgaccgcct caatgaggtc   1500

gctaaaaatt taaatgaatc actcattgac cttcaagaat tgggaaaata tgagcaatat   1560

attaaatggc cttggtatgt ttggctcggc ttcattgctg gactaattgc catcgtcatg   1620

gttacaatct tgctttgttg catgactagt tgttgcagtt gcctcaaggg tgcatgctct   1680

tgtggttctt gctgcaagtt tgatgaggat gactctgagc cagttctcaa gggtgtcaaa   1740

ttacattaca ca                                                       1752


<210> SEQ ID NO 12
<211> LENGTH: 588
<212> TYPE: PRT
<213> ORGANISM: Artificial Sequence
<220> FEATURE:
<223> OTHER INFORMATION: Synthetically generated peptide

<400> SEQUENCE: 12

Ala Glu Leu Lys Cys Ser Val Lys Ser Phe Glu Ile Asp Lys Gly Ile
 1               5                  10                  15

Tyr Gln Thr Ser Asn Phe Arg Val Val Pro Ser Gly Asp Val Val Arg
            20                  25                  30

Phe Pro Asn Ile Thr Asn Leu Cys Pro Phe Gly Glu Val Phe Asn Ala
        35                  40                  45

Thr Lys Phe Pro Ser Val Tyr Ala Trp Glu Arg Lys Lys Ile Ser Asn
    50                  55                  60

Cys Val Ala Asp Tyr Ser Val Leu Tyr Asn Ser Thr Phe Phe Ser Thr
65                  70                  75                  80

Phe Lys Cys Tyr Gly Val Ser Ala Thr Lys Leu Asn Asp Leu Cys Phe
                85                  90                  95

Ser Asn Val Tyr Ala Asp Ser Phe Val Val Lys Gly Asp Asp Val Arg
            100                 105                 110

Gln Ile Ala Pro Gly Gln Thr Gly Val Ile Ala Asp Tyr Asn Tyr Lys
        115                 120                 125

Leu Pro Asp Asp Phe Met Gly Cys Val Leu Ala Trp Asn Thr Arg Asn
    130                 135                 140

Ile Asp Ala Thr Ser Thr Gly Asn Tyr Asn Tyr Lys Tyr Arg Tyr Leu
145                 150                 155                 160

Arg His Gly Lys Leu Arg Pro Phe Glu Arg Asp Ile Ser Asn Val Pro
                165                 170                 175

Phe Ser Pro Asp Gly Lys Pro Cys Thr Pro Pro Ala Leu Asn Cys Tyr
            180                 185                 190

Trp Pro Leu Asn Asp Tyr Gly Phe Tyr Thr Thr Thr Gly Ile Gly Tyr
        195                 200                 205

Gln Pro Tyr Arg Val Val Val Leu Ser Phe Glu Leu Leu Asn Ala Pro
    210                 215                 220

Ala Thr Val Cys Gly Pro Lys Leu Ser Thr Asp Leu Ile Lys Asn Gln
225                 230                 235                 240
```

-continued

```
Cys Val Asn Phe Asn Phe Asn Gly Leu Thr Gly Thr Gly Val Leu Thr
                245                 250                 255

Pro Ser Ser Lys Arg Phe Gln Pro Phe Gln Gln Phe Gly Arg Asp Val
            260                 265                 270

Ser Asp Phe Thr Asp Ser Val Arg Asp Pro Lys Thr Ser Glu Ile Leu
        275                 280                 285

Asp Ile Ser Pro Cys Ala Phe Gly Gly Val Ser Val Ile Thr Pro Gly
    290                 295                 300

Thr Asn Ala Ser Ser Glu Val Ala Val Leu Tyr Gln Asp Val Asn Cys
305                 310                 315                 320

Thr Asp Val Ser Thr Ala Ile His Ala Asp Gln Leu Thr Pro Ala Trp
                325                 330                 335

Arg Ile Tyr Ser Thr Gly Asn Asn Val Phe Gln Thr Gln Ala Gly Cys
            340                 345                 350

Leu Ile Gly Ala Glu His Val Asp Thr Ser Tyr Glu Cys Asp Ile Pro
        355                 360                 365

Ile Gly Ala Gly Ile Cys Ala Ser Tyr His Thr Val Ser Leu Leu Arg
    370                 375                 380

Ser Thr Ser Gln Lys Ser Ile Val Ala Tyr Thr Met Ser Leu Gly Ala
385                 390                 395                 400

Asp Ser Ser Ile Ala Tyr Ser Asn Asn Thr Ile Ala Ile Pro Thr Asn
                405                 410                 415

Phe Ser Ile Ser Ile Thr Thr Glu Val Met Pro Val Ser Met Ala Lys
            420                 425                 430

Thr Ser Val Asp Cys Asn Met Tyr Ile Cys Gly Asp Ser Thr Glu Cys
        435                 440                 445

Ala Asn Leu Leu Gly Gly Gly Gly Gly Gly Gly Gly Asp Ser Phe Lys
    450                 455                 460

Glu Glu Leu Asp Lys Tyr Phe Lys Asn His Thr Ser Pro Asp Val Asp
465                 470                 475                 480

Leu Gly Asp Ile Ser Gly Ile Asn Ala Ser Val Val Asn Ile Gln Lys
                485                 490                 495

Glu Ile Asp Arg Leu Asn Glu Val Ala Lys Asn Leu Asn Glu Ser Leu
            500                 505                 510

Ile Asp Leu Gln Glu Leu Gly Lys Tyr Glu Gln Tyr Ile Lys Trp Pro
        515                 520                 525

Trp Tyr Val Trp Leu Gly Phe Ile Ala Gly Leu Ile Ala Ile Val Met
    530                 535                 540

Val Thr Ile Leu Leu Cys Cys Met Thr Ser Cys Cys Ser Cys Leu Lys
545                 550                 555                 560

Gly Ala Cys Ser Cys Gly Ser Cys Cys Lys Phe Asp Glu Asp Asp Ser
                565                 570                 575

Glu Pro Val Leu Lys Gly Val Lys Leu His Tyr Thr
            580                 585
```

```
<210> SEQ ID NO 13
<211> LENGTH: 1847
<212> TYPE: DNA
<213> ORGANISM: Artificial Sequence
<220> FEATURE:
<223> OTHER INFORMATION: Synthetically generated oligonucleotide

<400> SEQUENCE: 13

catacgtttg gcaaccctgt catacctttt aaggatggta tttattttgc tgccacagag      60

aaatcaaatg ttgtccgtgg ttgggttttt ggttctacca tgaacaacaa gtcacagtcg     120
```

-continued

```
gtgattatta ttaacaattc tactaatgtt gttatacgag catgtaactt tgaattgtgt    180
gacaaccctt tctttgctgt ttctaaaccc atgggtacac agacacatac tatgatattc    240
gataatgcat ttaattgcac tttcgagtac atatctgatg ccttttcgct tgatgtttca    300
gaaaagtcag gtaattttaa acacttacga gagtttgtgt ttaaaaataa agatgggttt    360
ctctatgttt ataagggcta tcaacctata gatgtagttc gtgatctacc ttctggtttt    420
aacactttga aacctatttt taagttgcct cttggtatta acattacaaa ttttagagcc    480
gaattcgggg gcgggggtgg aggtggtggc gagattgaca aaggaattta ccagacctct    540
aatttcaggg ttgttccctc aggagatgtt gtgagattcc ctaatattac aaacttgtgt    600
ccttttggag aggtttttaa tgctactaaa ttcccttctg tctatgcatg ggagagaaaa    660
aaaatttcta attgtgttgc tgattactct gtgctctaca actcaacatt tttttcaacc    720
tttaagtgct atggcgtttc tgccactaag ttgaatgatc tttgcttctc caatgtctat    780
gcagattctt ttgtagtcaa gggagatgat gtaagacaaa tagcgccagg acaaactggt    840
gttattgctg attataatta taaattgcca gatgatttca tgggttgtgt ccttgcttgg    900
aatactagga acattgatgc tacttcaact ggtaattata attataaata taggtatctt    960
agacatggca agcttaggcc ctttgagaga gacatatcta atgtgccttt ctcccctgat   1020
ggcaaacctt gcaccccacc tgctcttaat tgttattggc cattaaatga ttatggtttt   1080
tacaccacta ctggcattgg ctaccaacct tacagagttg tagtactttc ttttgaactt   1140
ttaaatgcac cggccacggt ttgtggacca aaattatcca ctgaccttat taagaaccag   1200
tgtgtcaatt ttaattttaa tggactcact ggtactggtg tgttaactcc ttcttcaaag   1260
agatttcaac catttcaaca atttggccgt gatgtttctg atttcactga ttccgttcga   1320
gatcctaaaa catctgaaat attagacatt tcaccttgct cttttggggg tgtaagtgta   1380
attacacctg gaacaaatgc ttcatctgaa gttgctgttc tatatcaaga tgttaactgc   1440
actgatgttt ctacagcaat tcatgcagat caactcacac cagcttggcg catatattct   1500
actggaaaca atgtattcca gactcaagca ggctgtctta taggagctga gcatgtcgac   1560
acttcttatg agtgcgacat tcctattgga gctggcattt gtgctagtta ccatacagtt   1620
tctttattac gtagtactag ccaaaaatct attgtggctt atactatgtc tttaggtgct   1680
gatagttcaa ttgcttactc taataacacc attgctatac ctactaactt ttcaattagc   1740
attactacag aagtaatgcc tgtttctatg gctaaaacct ccgtagattg taatatgtac   1800
atctgcggag attctactga atgtgctaat ttgcttctcc aatatgg                 1847
```

<210> SEQ ID NO 14
<211> LENGTH: 608
<212> TYPE: PRT
<213> ORGANISM: Artificial Sequence
<220> FEATURE:
<223> OTHER INFORMATION: Synthetically generated peptide

<400> SEQUENCE: 14

```
Val Ile Pro Phe Lys Asp Gly Ile Tyr Phe Ala Ala Thr Glu Lys Ser
 1               5                  10                  15

Asn Val Val Arg Gly Trp Val Phe Gly Ser Thr Met Asn Asn Lys Ser
            20                  25                  30

Gln Ser Val Ile Ile Ile Asn Asn Ser Thr Asn Val Val Ile Arg Ala
        35                  40                  45

Cys Asn Phe Glu Leu Cys Asp Asn Pro Phe Phe Ala Val Ser Lys Pro
```

-continued

```
    50                  55                  60

Met Gly Thr Gln Thr His Thr Met Ile Phe Asp Asn Ala Phe Asn Cys
65                  70                  75                  80

Thr Phe Glu Tyr Ile Ser Asp Ala Phe Ser Leu Asp Val Ser Glu Lys
                85                  90                  95

Ser Gly Asn Phe Lys His Leu Arg Glu Phe Val Phe Lys Asn Lys Asp
            100                 105                 110

Gly Phe Leu Tyr Val Tyr Lys Gly Tyr Gln Pro Ile Asp Val Val Arg
        115                 120                 125

Asp Leu Pro Ser Gly Phe Asn Thr Leu Lys Pro Ile Phe Lys Leu Pro
    130                 135                 140

Leu Gly Ile Asn Gly Gly Gly Gly Gly Gly Gly Gly Ala Glu Leu Lys
145                 150                 155                 160

Cys Ser Val Lys Ser Phe Glu Ile Asp Lys Gly Ile Tyr Gln Thr Ser
                165                 170                 175

Asn Phe Arg Val Val Pro Ser Gly Asp Val Val Arg Phe Pro Asn Ile
            180                 185                 190

Thr Asn Leu Cys Pro Phe Gly Glu Val Phe Asn Ala Thr Lys Phe Pro
        195                 200                 205

Ser Val Tyr Ala Trp Glu Arg Lys Lys Ile Ser Asn Cys Val Ala Asp
    210                 215                 220

Tyr Ser Val Leu Tyr Asn Ser Thr Phe Phe Ser Thr Phe Lys Cys Tyr
225                 230                 235                 240

Gly Val Ser Ala Thr Lys Leu Asn Asp Leu Cys Phe Ser Asn Val Tyr
                245                 250                 255

Ala Asp Ser Phe Val Val Lys Gly Asp Asp Val Arg Gln Ile Ala Pro
            260                 265                 270

Gly Gln Thr Gly Val Ile Ala Asp Tyr Asn Tyr Lys Leu Pro Asp Asp
        275                 280                 285

Phe Met Gly Cys Val Leu Ala Trp Asn Thr Arg Asn Ile Asp Ala Thr
    290                 295                 300

Ser Thr Gly Asn Tyr Asn Tyr Lys Tyr Arg Tyr Leu Arg His Gly Lys
305                 310                 315                 320

Leu Arg Pro Phe Glu Arg Asp Ile Ser Asn Val Pro Phe Ser Pro Asp
                325                 330                 335

Gly Lys Pro Cys Thr Pro Pro Ala Leu Asn Cys Tyr Trp Pro Leu Asn
            340                 345                 350

Asp Tyr Gly Phe Tyr Thr Thr Thr Gly Ile Gly Tyr Gln Pro Tyr Arg
        355                 360                 365

Val Val Val Leu Ser Phe Glu Leu Leu Asn Ala Pro Ala Thr Val Cys
    370                 375                 380

Gly Pro Lys Leu Ser Thr Asp Leu Ile Lys Asn Gln Cys Val Asn Phe
385                 390                 395                 400

Asn Phe Asn Gly Leu Thr Gly Thr Gly Val Leu Thr Pro Ser Ser Lys
                405                 410                 415

Arg Phe Gln Pro Phe Gln Gln Phe Gly Arg Asp Val Ser Asp Phe Thr
            420                 425                 430

Asp Ser Val Arg Asp Pro Lys Thr Ser Glu Ile Leu Asp Ile Ser Pro
        435                 440                 445

Cys Ala Phe Gly Gly Val Ser Val Ile Thr Pro Gly Thr Asn Ala Ser
    450                 455                 460

Ser Glu Val Ala Val Leu Tyr Gln Asp Val Asn Cys Thr Asp Val Ser
465                 470                 475                 480
```

-continued

```
Thr Ala Ile His Ala Asp Gln Leu Thr Pro Ala Trp Arg Ile Tyr Ser
                485                 490                 495

Thr Gly Asn Asn Val Phe Gln Thr Gln Ala Gly Cys Leu Ile Gly Ala
            500                 505                 510

Glu His Val Asp Thr Ser Tyr Glu Cys Asp Ile Pro Ile Gly Ala Gly
        515                 520                 525

Ile Cys Ala Ser Tyr His Thr Val Ser Leu Leu Arg Ser Thr Ser Gln
    530                 535                 540

Lys Ser Ile Val Ala Tyr Thr Met Ser Leu Gly Ala Asp Ser Ser Ile
545                 550                 555                 560

Ala Tyr Ser Asn Asn Thr Ile Ala Ile Pro Thr Asn Phe Ser Ile Ser
                565                 570                 575

Ile Thr Thr Glu Val Met Pro Val Ser Met Ala Lys Thr Ser Val Asp
            580                 585                 590

Cys Asn Met Tyr Ile Cys Gly Asp Ser Thr Glu Cys Ala Asn Leu Leu
        595                 600                 605
```

```
<210> SEQ ID NO 15
<211> LENGTH: 2262
<212> TYPE: DNA
<213> ORGANISM: Artificial Sequence
<220> FEATURE:
<223> OTHER INFORMATION: Synthetically generated oligonucletide

<400> SEQUENCE: 15

catacgtttg gcaaccctgt catacctttt aaggatggta tttattttgc tgccacagag      60

aaatcaaatg ttgtccgtgg ttgggttttt ggttctacca tgaacaacaa gtcacagtcg     120

gtgattatta ttaacaattc tactaatgtt gttatacgag catgtaactt tgaattgtgt     180

gacaaccctt tctttgctgt ttctaaaccc atgggtacac agacacatac tatgatattc     240

gataatgcat ttaattgcac tttcgagtac atatctgatg ccttttcgct tgatgtttca     300

gaaaagtcag gtaattttaa acacttacga gagtttgtgt ttaaaaataa agatgggttt     360

ctctatgttt ataagggcta tcaacctata gatgtagttc gtgatctacc ttctggtttt     420

aacactttga aacctatttt taagttgcct cttggtatta acattacaaa ttttagagcc     480

gaattcgggg gcgggggtgg aggtggtggc gagattgaca aaggaattta ccagacctct     540

aatttcaggg ttgttccctc aggagatgtt gtgagattcc ctaatattac aaacttgtgt     600

ccttttggag aggtttttaa tgctactaaa ttcccttctg tctatgcatg ggagagaaaa     660

aaaatttcta attgtgttgc tgattactct gtgctctaca actcaacatt tttttcaacc     720

tttaagtgct atggcgtttc tgccactaag ttgaatgatc tttgcttctc caatgtctat     780

gcagattctt ttgtagtcaa gggagatgat gtaagacaaa tagcgccagg acaaactggt     840

gttattgctg attataatta taaattgcca gatgatttca tgggttgtgt ccttgcttgg     900

aatactagga acattgatgc tacttcaact ggtaattata attataaata taggtatctt     960

agacatggca agcttaggcc ctttgagaga gacatatcta atgtgccttt ctcccctgat    1020

ggcaaacctt gcaccccacc tgctcttaat tgttattggc cattaaatga ttatggtttt    1080

tacaccacta ctggcattgg ctaccaacct tacagagttg tagtactttc ttttgaactt    1140

ttaaatgcac cggccacggt ttgtggacca aaattatcca ctgaccttat taagaaccag    1200

tgtgtcaatt ttaattttaa tggactcact ggtactggtg tgttaactcc ttcttcaaag    1260

agatttcaac catttcaaca atttggccgt gatgtttctg atttcactga ttccgttcga    1320
```

-continued

```
gatcctaaaa catctgaaat attagacatt tcaccttgct cttttggggg tgtaagtgta   1380

attacacctg gaacaaatgc ttcatctgaa gttgctgttc tatatcaaga tgttaactgc   1440

actgatgttt ctacagcaat tcatgcagat caactcacac cagcttggcg catatattct   1500

actggaaaca atgtattcca gactcaagca ggctgtctta taggagctga gcatgtcgac   1560

acttcttatg agtgcgacat tcctattgga gctggcattt gtgctagtta ccatacagtt   1620

tctttattac gtagtactag ccaaaaatct attgtggctt atactatgtc tttaggtgct   1680

gatagttcaa ttgcttactc taataacacc attgctatac ctactaactt ttcaattagc   1740

attactacag aagtaatgcc tgtttctatg gctaaaacct ccgtagattg taatatgtac   1800

atctgcggag attctactga atgtgctaat ttgcttctcc aatatgggcg gccgcctggg   1860

ggcgggggtg gaggtggtgg ctcattcaaa gaagagctgg acaagtactt caaaaatcat   1920

acatcaccag atgttgatct tggcgacatt tcaggcatta acgcttctgt cgtcaacatt   1980

caaaaagaaa ttgaccgcct caatgaggtc gctaaaaatt taaatgaatc actcattgac   2040

cttcaagaat tgggaaaata tgagcaatat attaaatggc cttggtatgt ttggctcggc   2100

ttcattgctg gactaattgc catcgtcatg gttacaatct tgctttgttg catgactagt   2160

tgttgcagtt gcctcaaggg tgcatgctct tgtggttctt gctgcaagtt tgatgaggat   2220

gactctgagc cagttctcaa gggtgtcaaa ttacattaca ca                      2262


<210> SEQ ID NO 16
<211> LENGTH: 744
<212> TYPE: PRT
<213> ORGANISM: Artificial Sequence
<220> FEATURE:
<223> OTHER INFORMATION: Synthetically generated peptide

<400> SEQUENCE: 16

Val Ile Pro Phe Lys Asp Gly Ile Tyr Phe Ala Ala Thr Glu Lys Ser
 1               5                  10                  15

Asn Val Val Arg Gly Trp Val Phe Gly Ser Thr Met Asn Asn Lys Ser
            20                  25                  30

Gln Ser Val Ile Ile Ile Asn Asn Ser Thr Asn Val Val Ile Arg Ala
        35                  40                  45

Cys Asn Phe Glu Leu Cys Asp Asn Pro Phe Phe Ala Val Ser Lys Pro
    50                  55                  60

Met Gly Thr Gln Thr His Thr Met Ile Phe Asp Asn Ala Phe Asn Cys
65                  70                  75                  80

Thr Phe Glu Tyr Ile Ser Asp Ala Phe Ser Leu Asp Val Ser Glu Lys
                85                  90                  95

Ser Gly Asn Phe Lys His Leu Arg Glu Phe Val Phe Lys Asn Lys Asp
            100                 105                 110

Gly Phe Leu Tyr Val Tyr Lys Gly Tyr Gln Pro Ile Asp Val Val Arg
        115                 120                 125

Asp Leu Pro Ser Gly Phe Asn Thr Leu Lys Pro Ile Phe Lys Leu Pro
    130                 135                 140

Leu Gly Ile Asn Gly Gly Gly Gly Gly Gly Gly Gly Ala Glu Leu Lys
145                 150                 155                 160

Cys Ser Val Lys Ser Phe Glu Ile Asp Lys Gly Ile Tyr Gln Thr Ser
                165                 170                 175

Asn Phe Arg Val Val Pro Ser Gly Asp Val Val Arg Phe Pro Asn Ile
            180                 185                 190

Thr Asn Leu Cys Pro Phe Gly Glu Val Phe Asn Ala Thr Lys Phe Pro
```

-continued

```
        195                 200                 205

Ser Val Tyr Ala Trp Glu Arg Lys Lys Ile Ser Asn Cys Val Ala Asp
    210                 215                 220

Tyr Ser Val Leu Tyr Asn Ser Thr Phe Phe Ser Thr Phe Lys Cys Tyr
225                 230                 235                 240

Gly Val Ser Ala Thr Lys Leu Asn Asp Leu Cys Phe Ser Asn Val Tyr
                245                 250                 255

Ala Asp Ser Phe Val Val Lys Gly Asp Asp Val Arg Gln Ile Ala Pro
            260                 265                 270

Gly Gln Thr Gly Val Ile Ala Asp Tyr Asn Tyr Lys Leu Pro Asp Asp
        275                 280                 285

Phe Met Gly Cys Val Leu Ala Trp Asn Thr Arg Asn Ile Asp Ala Thr
    290                 295                 300

Ser Thr Gly Asn Tyr Asn Tyr Lys Tyr Arg Tyr Leu Arg His Gly Lys
305                 310                 315                 320

Leu Arg Pro Phe Glu Arg Asp Ile Ser Asn Val Pro Phe Ser Pro Asp
                325                 330                 335

Gly Lys Pro Cys Thr Pro Pro Ala Leu Asn Cys Tyr Trp Pro Leu Asn
            340                 345                 350

Asp Tyr Gly Phe Tyr Thr Thr Thr Gly Ile Gly Tyr Gln Pro Tyr Arg
        355                 360                 365

Val Val Val Leu Ser Phe Glu Leu Leu Asn Ala Pro Ala Thr Val Cys
    370                 375                 380

Gly Pro Lys Leu Ser Thr Asp Leu Ile Lys Asn Gln Cys Val Asn Phe
385                 390                 395                 400

Asn Phe Asn Gly Leu Thr Gly Thr Gly Val Leu Thr Pro Ser Ser Lys
                405                 410                 415

Arg Phe Gln Pro Phe Gln Gln Phe Gly Arg Asp Val Ser Asp Phe Thr
            420                 425                 430

Asp Ser Val Arg Asp Pro Lys Thr Ser Glu Ile Leu Asp Ile Ser Pro
        435                 440                 445

Cys Ala Phe Gly Gly Val Ser Val Ile Thr Pro Gly Thr Asn Ala Ser
    450                 455                 460

Ser Glu Val Ala Val Leu Tyr Gln Asp Val Asn Cys Thr Asp Val Ser
465                 470                 475                 480

Thr Ala Ile His Ala Asp Gln Leu Thr Pro Ala Trp Arg Ile Tyr Ser
                485                 490                 495

Thr Gly Asn Asn Val Phe Gln Thr Gln Ala Gly Cys Leu Ile Gly Ala
            500                 505                 510

Glu His Val Asp Thr Ser Tyr Glu Cys Asp Ile Pro Ile Gly Ala Gly
        515                 520                 525

Ile Cys Ala Ser Tyr His Thr Val Ser Leu Leu Arg Ser Thr Ser Gln
    530                 535                 540

Lys Ser Ile Val Ala Tyr Thr Met Ser Leu Gly Ala Asp Ser Ser Ile
545                 550                 555                 560

Ala Tyr Ser Asn Asn Thr Ile Ala Ile Pro Thr Asn Phe Ser Ile Ser
                565                 570                 575

Ile Thr Thr Glu Val Met Pro Val Ser Met Ala Lys Thr Ser Val Asp
            580                 585                 590

Cys Asn Met Tyr Ile Cys Gly Asp Ser Thr Glu Cys Ala Asn Leu Leu
        595                 600                 605

Gly Gly Gly Gly Gly Gly Gly Gly Asp Ser Phe Lys Glu Glu Leu Asp
    610                 615                 620
```

-continued

Lys Tyr Phe Lys Asn His Thr Ser Pro Asp Val Asp Leu Gly Asp Ile
625 630 635 640

Ser Gly Ile Asn Ala Ser Val Val Asn Ile Gln Lys Glu Ile Asp Arg
645 650 655

Leu Asn Glu Val Ala Lys Asn Leu Asn Glu Ser Leu Ile Asp Leu Gln
660 665 670

Glu Leu Gly Lys Tyr Glu Gln Tyr Ile Lys Trp Pro Trp Tyr Val Trp
675 680 685

Leu Gly Phe Ile Ala Gly Leu Ile Ala Ile Val Met Val Thr Ile Leu
690 695 700

Leu Cys Cys Met Thr Ser Cys Cys Ser Cys Leu Lys Gly Ala Cys Ser
705 710 715 720

Cys Gly Ser Cys Cys Lys Phe Asp Glu Asp Asp Ser Glu Pro Val Leu
725 730 735

Lys Gly Val Lys Leu His Tyr Thr
740

<210> SEQ ID NO 17
<211> LENGTH: 999
<212> TYPE: DNA
<213> ORGANISM: SARS coronavirus Urbani

<400> SEQUENCE: 17
atgtttattt tcttattatt tcttactctc actagtggta gtgaccttga ccggtgcacc 60
acttttgatg atgttcaagc tcctaattac actcaacata cttcatctat gaggggggtt 120
tactatcctg atgaaatttt tagatcagac actctttatt taactcagga tttatttctt 180
ccattttatt ctaatgttac agggtttcat actattaatc atacgtttgg caaccctgtc 240 ataccttta aggatggtat ttattttgct gccacagaga aatcaaatgt tgtccgtggt 300
tgggtttttg gttctaccat gaacaacaag tcacagtcgg tgattattat taacaattct 360
actaatgttg ttatacgagc atgtaacttt gaattgtgtg acaacccttt ctttgctgtt 420
tctaaaccca tgggtacaca gacacatact atgatattcg ataatgcatt taattgcact 480
ttcgagtaca tatctgatgc cttttcgctt gatgtttcag aaaagtcagg taattttaaa 540
cacttacgag agtttgtgtt taaaaataaa gatgggtttc tctatgttta taagggctat 600
caacctatag atgtagttcg tgatctacct tctggtttta acactttgaa acctattttt 660
aagttgcctc ttggtattaa cattacaaat tttagagcca ttcttacagc cttttcacct 720
gctcaagaca tttggggcac gtcagctgca gcctattttg ttggctattt aaagccaact 780
acatttatgc tcaagtatga tgaaaatggt acaatcacag atgctgttga ttgttctcaa 840
aatccacttg ctgaactcaa atgctctgtt aagagctttg agattgacaa aggaatttac 900
cagacctcta atttcagggt tgttccctca ggagatgttg tgagattccc taatattaca 960
aacttgtgtc cttttggaga ggtttttaat gctactaaa 999

<210> SEQ ID NO 18
<211> LENGTH: 333
<212> TYPE: PRT
<213> ORGANISM: SARS coronavirus Urbani

<400> SEQUENCE: 18

Met Phe Ile Phe Leu Leu Phe Leu Thr Leu Thr Ser Gly Ser Asp Leu
1 5 10 15

Asp Arg Cys Thr Thr Phe Asp Asp Val Gln Ala Pro Asn Tyr Thr Gln

-continued

```
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys
                325                 330


<210> SEQ ID NO 19
<211> LENGTH: 999
<212> TYPE: DNA
<213> ORGANISM: SARS coronavirus Urbani

<400> SEQUENCE: 19

ttcccttctg tctatgcatg ggagagaaaa aaaatttcta attgtgttgc tgattactct      60

gtgctctaca actcaacatt tttttcaacc tttaagtgct atggcgtttc tgccactaag     120

ttgaatgatc tttgcttctc caatgtctat gcagattctt ttgtagtcaa gggagatgat     180

gtaagacaaa tagcgccagg acaaactggt gttattgctg attataatta taaattgcca     240

gatgatttca tgggttgtgt ccttgcttgg aatactagga acattgatgc tacttcaact     300

ggtaattata attataaata taggtatctt agacatggca agcttaggcc ctttgagaga     360
```

-continued

```
gacatatcta atgtgccttt ctcccctgat ggcaaacctt gcaccccacc tgctcttaat    420

tgttattggc cattaaatga ttatggtttt tacaccacta ctggcattgg ctaccaacct    480

tacagagttg tagtactttc ttttgaactt ttaaatgcac cggccacggt ttgtggacca    540

aaattatcca ctgaccttat taagaaccag tgtgtcaatt ttaattttaa tggactcact    600

ggtactggtg tgttaactcc ttcttcaaag agatttcaac catttcaaca atttggccgt    660

gatgtttctg atttcactga ttccgttcga gatcctaaaa catctgaaat attagacatt    720

tcaccttgct cttttggggg tgtaagtgta attacacctg gaacaaatgc ttcatctgaa    780

gttgctgttc tatatcaaga tgttaactgc actgatgttt ctacagcaat tcatgcagat    840

caactcacac cagcttggcg catatattct actggaaaca atgtattcca gactcaagca    900

ggctgtctta taggagctga gcatgtcgac acttcttatg agtgcgacat tcctattgga    960

gctggcattt gtgctagtta ccatacagtt tctttatta                           999


<210> SEQ ID NO 20
<211> LENGTH: 333
<212> TYPE: PRT
<213> ORGANISM: SARS coronavirus Urbani

<400> SEQUENCE: 20

Phe Pro Ser Val Tyr Ala Trp Glu Arg Lys Lys Ile Ser Asn Cys Val
 1               5                  10                  15

Ala Asp Tyr Ser Val Leu Tyr Asn Ser Thr Phe Phe Ser Thr Phe Lys
            20                  25                  30

Cys Tyr Gly Val Ser Ala Thr Lys Leu Asn Asp Leu Cys Phe Ser Asn
        35                  40                  45

Val Tyr Ala Asp Ser Phe Val Val Lys Gly Asp Asp Val Arg Gln Ile
    50                  55                  60

Ala Pro Gly Gln Thr Gly Val Ile Ala Asp Tyr Asn Tyr Lys Leu Pro
65                  70                  75                  80

Asp Asp Phe Met Gly Cys Val Leu Ala Trp Asn Thr Arg Asn Ile Asp
                85                  90                  95

Ala Thr Ser Thr Gly Asn Tyr Asn Tyr Lys Tyr Arg Tyr Leu Arg His
            100                 105                 110

Gly Lys Leu Arg Pro Phe Glu Arg Asp Ile Ser Asn Val Pro Phe Ser
        115                 120                 125

Pro Asp Gly Lys Pro Cys Thr Pro Pro Ala Leu Asn Cys Tyr Trp Pro
    130                 135                 140

Leu Asn Asp Tyr Gly Phe Tyr Thr Thr Thr Gly Ile Gly Tyr Gln Pro
145                 150                 155                 160

Tyr Arg Val Val Val Leu Ser Phe Glu Leu Leu Asn Ala Pro Ala Thr
                165                 170                 175

Val Cys Gly Pro Lys Leu Ser Thr Asp Leu Ile Lys Asn Gln Cys Val
            180                 185                 190

Asn Phe Asn Phe Asn Gly Leu Thr Gly Thr Gly Val Leu Thr Pro Ser
        195                 200                 205

Ser Lys Arg Phe Gln Pro Phe Gln Gln Phe Gly Arg Asp Val Ser Asp
    210                 215                 220

Phe Thr Asp Ser Val Arg Asp Pro Lys Thr Ser Glu Ile Leu Asp Ile
225                 230                 235                 240

Ser Pro Cys Ala Phe Gly Gly Val Ser Val Ile Thr Pro Gly Thr Asn
                245                 250                 255

Ala Ser Ser Glu Val Ala Val Leu Tyr Gln Asp Val Asn Cys Thr Asp
```

-continued

```
            260                 265                 270

Val Ser Thr Ala Ile His Ala Asp Gln Leu Thr Pro Ala Trp Arg Ile
        275                 280                 285

Tyr Ser Thr Gly Asn Asn Val Phe Gln Thr Gln Ala Gly Cys Leu Ile
    290                 295                 300

Gly Ala Glu His Val Asp Thr Ser Tyr Glu Cys Asp Ile Pro Ile Gly
305                 310                 315                 320

Ala Gly Ile Cys Ala Ser Tyr His Thr Val Ser Leu Leu
                325                 330


<210> SEQ ID NO 21
<211> LENGTH: 1002
<212> TYPE: DNA
<213> ORGANISM: SARS coronavirus Urbani

<400> SEQUENCE: 21

cgtagtacta gccaaaaatc tattgtggct tatactatgt ctttaggtgc tgatagttca      60

attgcttact ctaataacac cattgctata cctactaact tttcaattag cattactaca     120

gaagtaatgc ctgtttctat ggctaaaacc tccgtagatt gtaatatgta catctgcgga     180

gattctactg aatgtgctaa tttgcttctc caatatggta gcttttgcac acaactaaat     240

cgtgcactct caggtattgc tgctgaacag gatcgcaaca cacgtgaagt gttcgctcaa     300

gtcaaacaaa tgtacaaaac cccaactttg aaatattttg gtggttttaa tttttcacaa     360

atattacctg accctctaaa gccaactaag aggtctttta ttgaggactt gctctttaat     420

aaggtgacac tcgctgatgc tggcttcatg aagcaatatg gcgaatgcct aggtgatatt     480

aatgctagag atctcatttg tgcgcagaag ttcaatggac ttacagtgtt gccacctctg     540

ctcactgatg atatgattgc tgcctacact gctgctctag ttagtggtac tgccactgct     600

ggatggacat ttggtgctgg cgctgctctt caaatacctt ttgctatgca aatggcatat     660

aggttcaatg gcattggagt tacccaaaat gttctctatg agaaccaaaa acaaatcgcc     720

aaccaattta acaaggcgat tagtcaaatt caagaatcac ttacaacaac atcaactgca     780

ttgggcaagc tgcaagacgt tgttaaccag aatgctcaag cattaaacac acttgttaaa     840

caacttagct ctaattttgg tgcaatttca agtgtgctaa atgatatcct ttcgcgactt     900

gataaagtcg aggcggaggt acaaattgac aggttaatta caggcagact tcaaagcctt     960

caaacctatg taacacaaca actaatcagg gctgctgaaa tc                       1002


<210> SEQ ID NO 22
<211> LENGTH: 334
<212> TYPE: PRT
<213> ORGANISM: SARS coronavirus Urbani

<400> SEQUENCE: 22

Arg Ser Thr Ser Gln Lys Ser Ile Val Ala Tyr Thr Met Ser Leu Gly
 1               5                  10                  15

Ala Asp Ser Ser Ile Ala Tyr Ser Asn Asn Thr Ile Ala Ile Pro Thr
            20                  25                  30

Asn Phe Ser Ile Ser Ile Thr Thr Glu Val Met Pro Val Ser Met Ala
        35                  40                  45

Lys Thr Ser Val Asp Cys Asn Met Tyr Ile Cys Gly Asp Ser Thr Glu
    50                  55                  60

Cys Ala Asn Leu Leu Leu Gln Tyr Gly Ser Phe Cys Thr Gln Leu Asn
65                  70                  75                  80
```

-continued

```
Arg Ala Leu Ser Gly Ile Ala Ala Glu Gln Asp Arg Asn Thr Arg Glu
                85                  90                  95

Val Phe Ala Gln Val Lys Gln Met Tyr Lys Thr Pro Thr Leu Lys Tyr
            100                 105                 110

Phe Gly Gly Phe Asn Phe Ser Gln Ile Leu Pro Asp Pro Leu Lys Pro
        115                 120                 125

Thr Lys Arg Ser Phe Ile Glu Asp Leu Leu Phe Asn Lys Val Thr Leu
    130                 135                 140

Ala Asp Ala Gly Phe Met Lys Gln Tyr Gly Glu Cys Leu Gly Asp Ile
145                 150                 155                 160

Asn Ala Arg Asp Leu Ile Cys Ala Gln Lys Phe Asn Gly Leu Thr Val
                165                 170                 175

Leu Pro Pro Leu Leu Thr Asp Asp Met Ile Ala Ala Tyr Thr Ala Ala
            180                 185                 190

Leu Val Ser Gly Thr Ala Thr Ala Gly Trp Thr Phe Gly Ala Gly Ala
        195                 200                 205

Ala Leu Gln Ile Pro Phe Ala Met Gln Met Ala Tyr Arg Phe Asn Gly
    210                 215                 220

Ile Gly Val Thr Gln Asn Val Leu Tyr Glu Asn Gln Lys Gln Ile Ala
225                 230                 235                 240

Asn Gln Phe Asn Lys Ala Ile Ser Gln Ile Gln Glu Ser Leu Thr Thr
                245                 250                 255

Thr Ser Thr Ala Leu Gly Lys Leu Gln Asp Val Val Asn Gln Asn Ala
            260                 265                 270

Gln Ala Leu Asn Thr Leu Val Lys Gln Leu Ser Ser Asn Phe Gly Ala
        275                 280                 285

Ile Ser Ser Val Leu Asn Asp Ile Leu Ser Arg Leu Asp Lys Val Glu
    290                 295                 300

Ala Glu Val Gln Ile Asp Arg Leu Ile Thr Gly Arg Leu Gln Ser Leu
305                 310                 315                 320

Gln Thr Tyr Val Thr Gln Gln Leu Ile Arg Ala Ala Glu Ile
                325                 330
```

<210> SEQ ID NO 23
<211> LENGTH: 102
<212> TYPE: DNA
<213> ORGANISM: SARS coronavirus Urbani

<400> SEQUENCE: 23

```
ggtaattata attataaata taggtatctt agacatggca agcttaggcc ctttgagaga      60

gacatatcta atgtgccttt ctcccctgat ggcaaacctt gc                        102
```

<210> SEQ ID NO 24
<211> LENGTH: 34
<212> TYPE: PRT
<213> ORGANISM: SARS coronavirus Urbani

<400> SEQUENCE: 24

```
Gly Asn Tyr Asn Tyr Lys Tyr Arg Tyr Leu Arg His Gly Lys Leu Arg
 1               5                  10                  15

Pro Phe Glu Arg Asp Ile Ser Asn Val Pro Phe Ser Pro Asp Gly Lys
            20                  25                  30

Pro Cys
```

<210> SEQ ID NO 25
<211> LENGTH: 150

-continued

<212> TYPE: DNA
<213> ORGANISM: SARS coronavirus Urbani

<400> SEQUENCE: 25

```
gatcctaaaa catctgaaat attagacatt tcaccttgct cttttggggg tgtaagtgta     60

attacacctg gaacaaatgc ttcatctgaa gttgctgttc tatatcaaga tgttaactgc    120

actgatgttt ctacagcaat tcatgcagat                                     150
```

<210> SEQ ID NO 26
<211> LENGTH: 50
<212> TYPE: PRT
<213> ORGANISM: SARS coronavirus Urbani

<400> SEQUENCE: 26

```
Asp Pro Lys Thr Ser Glu Ile Leu Asp Ile Ser Pro Cys Ala Phe Gly
 1               5                  10                  15

Gly Val Ser Val Ile Thr Pro Gly Thr Asn Ala Ser Ser Glu Val Ala
            20                  25                  30

Val Leu Tyr Gln Asp Val Asn Cys Thr Asp Val Ser Thr Ala Ile His
        35                  40                  45

Ala Asp
    50
```

<210> SEQ ID NO 27
<211> LENGTH: 384
<212> TYPE: DNA
<213> ORGANISM: SARS coronavirus Urbani

<400> SEQUENCE: 27

```
gactcattca aagaagagct ggacaagtac ttcaaaaatc atacatcacc agatgttgat     60

cttggcgaca tttcaggcat taacgcttct gtcgtcaaca ttcaaaaaga aattgaccgc    120

ctcaatgagg tcgctaaaaa tttaaatgaa tcactcattg accttcaaga attgggaaaa    180

tatgagcaat atattaaatg gccttggtat gtttggctcg gcttcattgc tggactaatt    240

gccatcgtca tggttacaat cttgctttgt tgcatgacta gttgttgcag ttgcctcaag    300

ggtgcatgct cttgtggttc ttgctgcaag tttgatgagg atgactctga gccagttctc    360

aagggtgtca aattacatta caca                                           384
```

<210> SEQ ID NO 28
<211> LENGTH: 128
<212> TYPE: PRT
<213> ORGANISM: SARS coronavirus Urbani

<400> SEQUENCE: 28

```
Asp Ser Phe Lys Glu Glu Leu Asp Lys Tyr Phe Lys Asn His Thr Ser
 1               5                  10                  15

Pro Asp Val Asp Leu Gly Asp Ile Ser Gly Ile Asn Ala Ser Val Val
            20                  25                  30

Asn Ile Gln Lys Glu Ile Asp Arg Leu Asn Glu Val Ala Lys Asn Leu
        35                  40                  45

Asn Glu Ser Leu Ile Asp Leu Gln Glu Leu Gly Lys Tyr Glu Gln Tyr
    50                  55                  60

Ile Lys Trp Pro Trp Tyr Val Trp Leu Gly Phe Ile Ala Gly Leu Ile
65                  70                  75                  80

Ala Ile Val Met Val Thr Ile Leu Leu Cys Cys Met Thr Ser Cys Cys
                85                  90                  95
```

-continued

```
Ser Cys Leu Lys Gly Ala Cys Ser Cys Gly Ser Cys Cys Lys Phe Asp
            100                 105                 110

Glu Asp Asp Ser Glu Pro Val Leu Lys Gly Val Lys Leu His Tyr Thr
        115                 120                 125


<210> SEQ ID NO 29
<211> LENGTH: 30
<212> TYPE: PRT
<213> ORGANISM: Artificial Sequence
<220> FEATURE:
<223> OTHER INFORMATION: Synthetically generated SARS COV peptide

<400> SEQUENCE: 29

Lys Ser Gly Asn Phe Lys His Leu Arg Glu Phe Val Phe Lys Asn Lys
 1               5                  10                  15

Asp Gly Phe Leu Tyr Val Tyr Lys Gly Gln Pro Ile Asp Val
            20                  25                  30


<210> SEQ ID NO 30
<211> LENGTH: 32
<212> TYPE: PRT
<213> ORGANISM: Artificial Sequence
<220> FEATURE:
<223> OTHER INFORMATION: Synthetically generated SARS COV peptide

<400> SEQUENCE: 30

Asp Ser Phe Lys Glu Glu Leu Asp Arg Tyr Phe Lys Asn His Thr Ser
 1               5                  10                  15

Pro Asp Val Asp Leu Gly Asp Ile Ser Gly Ile Asn Ala Ser Val Val
            20                  25                  30


<210> SEQ ID NO 31
<211> LENGTH: 35
<212> TYPE: PRT
<213> ORGANISM: Artificial Sequence
<220> FEATURE:
<223> OTHER INFORMATION: Synthetically generated SARS COV peptide

<400> SEQUENCE: 31

Ala Leu Arg Leu Cys Ala Tyr Cys Cys Asn Ile Val Asn Val Ser Leu
 1               5                  10                  15

Val Lys Pro Thr Val Tyr Val Tyr Ser Arg Val Lys Asn Leu Asn Ser
            20                  25                  30

Ser Glu Gly
        35


<210> SEQ ID NO 32
<211> LENGTH: 33
<212> TYPE: PRT
<213> ORGANISM: Artificial Sequence
<220> FEATURE:
<223> OTHER INFORMATION: Synthetically generated SARS COV peptide

<400> SEQUENCE: 32

Met Ala Asp Asn Gly Thr Ile Thr Val Glu Glu Leu Lys Gln Leu Leu
 1               5                  10                  15

Glu Gln Trp Asn Leu Val Ile Cys Phe Leu Phe Leu Ala Trp Ile Met
            20                  25                  30

Leu


<210> SEQ ID NO 33
<211> LENGTH: 26
<212> TYPE: DNA
```

-continued

```
<213> ORGANISM: Artificial Sequence
<220> FEATURE:
<223> OTHER INFORMATION: Primer

<400> SEQUENCE: 33

ggatccgcca ccatgcatac gtttgg                                          26


<210> SEQ ID NO 34
<211> LENGTH: 18
<212> TYPE: DNA
<213> ORGANISM: Artificial Sequence
<220> FEATURE:
<223> OTHER INFORMATION: Primer

<400> SEQUENCE: 34

cttaagccga gattttaa                                                   18


<210> SEQ ID NO 35
<211> LENGTH: 25
<212> TYPE: DNA
<213> ORGANISM: Artificial Sequence
<220> FEATURE:
<223> OTHER INFORMATION: Synthetically generated SARS COV peptide

<400> SEQUENCE: 35

ggatccgcca ccatggagat tgaca                                           25


<210> SEQ ID NO 36
<211> LENGTH: 15
<212> TYPE: DNA
<213> ORGANISM: Artificial Sequence
<220> FEATURE:
<223> OTHER INFORMATION: Primer

<400> SEQUENCE: 36

cgccggcggg tataa                                                      15


<210> SEQ ID NO 37
<211> LENGTH: 37
<212> TYPE: DNA
<213> ORGANISM: Artificial Sequence
<220> FEATURE:
<223> OTHER INFORMATION: Primer

<400> SEQUENCE: 37

aggggatcca tgtttatttt cttattattt cttactc                              37


<210> SEQ ID NO 38
<211> LENGTH: 34
<212> TYPE: DNA
<213> ORGANISM: Artificial Sequence
<220> FEATURE:
<223> OTHER INFORMATION: Primer

<400> SEQUENCE: 38

cctggatcct ttagtagcat taaaaacctc tcca                                 34


<210> SEQ ID NO 39
<211> LENGTH: 34
<212> TYPE: DNA
<213> ORGANISM: Artificial Sequence
<220> FEATURE:
<223> OTHER INFORMATION: Primer

<400> SEQUENCE: 39

aggggatcct tcccttctgt ctatgcatgg gaga                                 34
```

-continued

<210> SEQ ID NO 40
<211> LENGTH: 34
<212> TYPE: DNA
<213> ORGANISM: Artificial Sequence
<220> FEATURE:
<223> OTHER INFORMATION: Synthetically generated SARS COV peptide

<400> SEQUENCE: 40
cctggatcct aataaagaaa ctgtatggta acta 34

<210> SEQ ID NO 41
<211> LENGTH: 34
<212> TYPE: DNA
<213> ORGANISM: Artificial Sequence
<220> FEATURE:
<223> OTHER INFORMATION: Primer

<400> SEQUENCE: 41
aggggatccc gtagtactag ccaaaaatct attg 34

<210> SEQ ID NO 42
<211> LENGTH: 34
<212> TYPE: DNA
<213> ORGANISM: Artificial Sequence
<220> FEATURE:
<223> OTHER INFORMATION: Primer

<400> SEQUENCE: 42
cctggatcct tcagcagccc tgattagttg ttgt 34

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
catacgtttg gcaaccctgt c 21

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
aacattacaa attttagagc c 21

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
gagattgaca aaggaattta c 21

<210> SEQ ID NO 46
<211> LENGTH: 22
<212> TYPE: DNA
<213> ORGANISM: Artificial Sequence
<220> FEATURE:

-continued

<223> OTHER INFORMATION: Primer

<400> SEQUENCE: 46
ctaatttgct tctccaatat gg 22

<210> SEQ ID NO 47
<211> LENGTH: 21
<212> TYPE: DNA
<213> ORGANISM: Artificial Sequence
<220> FEATURE:
<223> OTHER INFORMATION: Primer

<400> SEQUENCE: 47
atggctaaaa cctccgtaga t 21

<210> SEQ ID NO 48
<211> LENGTH: 21
<212> TYPE: DNA
<213> ORGANISM: Artificial Sequence
<220> FEATURE:
<223> OTHER INFORMATION: Primer

<400> SEQUENCE: 48
aattgtgatg tcgttattgg c 21

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
acttcaaaaa tcatacatca 20

<210> SEQ ID NO 50
<211> LENGTH: 24
<212> TYPE: DNA
<213> ORGANISM: Artificial Sequence
<220> FEATURE:
<223> OTHER INFORMATION: Primer

<400> SEQUENCE: 50
ggtgtcaaat tacattacac ataa 24

<210> SEQ ID NO 51
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 51

Val Ile Pro Phe Lys Asp Gly Ile Tyr Phe Ala Ala Thr Glu Lys
1 5 10 15

<210> SEQ ID NO 52
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 52

Asp Gly Ile Tyr Phe Ala Ala Thr Glu Lys Ser Asn Val Val Arg
1 5 10 15

-continued

<210> SEQ ID NO 53
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 53

Ala Ala Thr Glu Lys Ser Asn Val Val Arg Gly Trp Val Phe Gly
1 5 10 15

<210> SEQ ID NO 54
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 54

Ser Asn Val Val Arg Gly Trp Val Phe Gly Ser Thr Met Asn Asn
1 5 10 15

<210> SEQ ID NO 55
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 55

Gly Trp Val Phe Gly Ser Thr Met Asn Asn Lys Ser Gln Ser Val
1 5 10 15

<210> SEQ ID NO 56
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 56

Ser Thr Met Asn Asn Lys Ser Gln Ser Val Ile Ile Ile Asn Asn
1 5 10 15

<210> SEQ ID NO 57
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 57

Lys Ser Gln Ser Val Ile Ile Ile Asn Asn Ser Thr Asn Val Val
1 5 10 15

<210> SEQ ID NO 58
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 58

Ile Ile Ile Asn Asn Ser Thr Asn Val Val Ile Arg Ala Cys Asn
1 5 10 15

-continued

```
<210> SEQ ID NO 59
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 59

Ser Thr Asn Val Val Ile Arg Ala Cys Asn Phe Glu Leu Cys Asp
 1               5                  10                  15


<210> SEQ ID NO 60
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 60

Ile Arg Ala Cys Asn Phe Glu Leu Cys Asp Asn Pro Phe Phe Ala
 1               5                  10                  15


<210> SEQ ID NO 61
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 61

Phe Glu Leu Cys Asp Asn Pro Phe Phe Ala Val Ser Lys Pro Met
 1               5                  10                  15


<210> SEQ ID NO 62
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 62

Asn Pro Phe Phe Ala Val Ser Lys Pro Met Gly Thr Gln Thr His
 1               5                  10                  15


<210> SEQ ID NO 63
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 63

Val Ser Lys Pro Met Gly Thr Gln Thr His Thr Met Ile Phe Asp
 1               5                  10                  15


<210> SEQ ID NO 64
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 64

Gly Thr Gln Thr His Thr Met Ile Phe Asp Asn Ala Phe Asn Cys
 1               5                  10                  15
```

-continued

<210> SEQ ID NO 65
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 65

Thr Met Ile Phe Asp Asn Ala Phe Asn Cys Thr Phe Glu Tyr Ile
1 5 10 15

<210> SEQ ID NO 66
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 66

Asn Ala Phe Asn Cys Thr Phe Glu Tyr Ile Ser Asp Ala Phe Ser
1 5 10 15

<210> SEQ ID NO 67
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 67

Thr Phe Glu Tyr Ile Ser Asp Ala Phe Ser Leu Asp Val Ser Glu
1 5 10 15

<210> SEQ ID NO 68
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 68

Ser Asp Ala Phe Ser Leu Asp Val Ser Glu Lys Ser Gly Asn Phe
1 5 10 15

<210> SEQ ID NO 69
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 69

Leu Asp Val Ser Glu Lys Ser Gly Asn Phe Lys His Leu Arg Glu
1 5 10 15

<210> SEQ ID NO 70
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 70

Lys Ser Gly Asn Phe Lys His Leu Arg Glu Phe Val Phe Lys Asn
1 5 10 15

<210> SEQ ID NO 71

-continued

<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 71

Lys His Leu Arg Glu Phe Val Phe Lys Asn Lys Asp Gly Phe Leu
1 5 10 15

<210> SEQ ID NO 72
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 72

Phe Val Phe Lys Asn Lys Asp Gly Phe Leu Tyr Val Tyr Lys Gly
1 5 10 15

<210> SEQ ID NO 73
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 73

Lys Asp Gly Phe Leu Tyr Val Tyr Lys Gly Tyr Gln Pro Ile Asp
1 5 10 15

<210> SEQ ID NO 74
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 74

Tyr Val Tyr Lys Gly Tyr Gln Pro Ile Asp Val Val Arg Asp Leu
1 5 10 15

<210> SEQ ID NO 75
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 75

Tyr Gln Pro Ile Asp Val Val Arg Asp Leu Pro Ser Gly Phe Asn
1 5 10 15

<210> SEQ ID NO 76
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 76

Val Val Arg Asp Leu Pro Ser Gly Phe Asn Thr Leu Lys Pro Ile
1 5 10 15

<210> SEQ ID NO 77
<211> LENGTH: 15

-continued

<212> TYPE: PRT
<213> ORGANISM: Artificial Sequence
<220> FEATURE:
<223> OTHER INFORMATION: Synthetically generated SARS CoV S peptide

<400> SEQUENCE: 77

Pro Ser Gly Phe Asn Thr Leu Lys Pro Ile Phe Lys Leu Pro Leu
1 5 10 15

<210> SEQ ID NO 78
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 78

Ala Glu Leu Lys Cys Ser Val Lys Ser Phe Glu Ile Asp Lys Gly
1 5 10 15

<210> SEQ ID NO 79
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 79

Ser Val Lys Ser Phe Glu Ile Asp Lys Gly Ile Tyr Gln Thr Ser
1 5 10 15

<210> SEQ ID NO 80
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 80

Glu Ile Asp Lys Gly Ile Tyr Gln Thr Ser Asn Phe Arg Val Val
1 5 10 15

<210> SEQ ID NO 81
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 81

Ile Tyr Gln Thr Ser Asn Phe Arg Val Val Pro Ser Gly Asp Val
1 5 10 15

<210> SEQ ID NO 82
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 82

Asn Phe Arg Val Val Pro Ser Gly Asp Val Val Arg Phe Pro Asn
1 5 10 15

<210> SEQ ID NO 83
<211> LENGTH: 15
<212> TYPE: PRT

-continued

<213> ORGANISM: Artificial Sequence
<220> FEATURE:
<223> OTHER INFORMATION: Synthetically generated SARS CoV S peptide

<400> SEQUENCE: 83

Pro Ser Gly Asp Val Val Arg Phe Pro Asn Ile Thr Asn Leu Cys
1 5 10 15

<210> SEQ ID NO 84
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 84

Val Arg Phe Pro Asn Ile Thr Asn Leu Cys Pro Phe Gly Glu Val
1 5 10 15

<210> SEQ ID NO 85
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 85

Ile Thr Asn Leu Cys Pro Phe Gly Glu Val Phe Asn Ala Thr Lys
1 5 10 15

<210> SEQ ID NO 86
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 86

Pro Phe Gly Glu Val Phe Asn Ala Thr Lys Phe Pro Ser Val Tyr
1 5 10 15

<210> SEQ ID NO 87
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 87

Phe Asn Ala Thr Lys Phe Pro Ser Val Tyr Ala Trp Glu Arg Lys
1 5 10 15

<210> SEQ ID NO 88
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 88

Phe Pro Ser Val Tyr Ala Trp Glu Arg Lys Lys Ile Ser Asn Cys
1 5 10 15

<210> SEQ ID NO 89
<211> LENGTH: 15
<212> TYPE: PRT
<213> ORGANISM: Artificial Sequence -continued
<220> FEATURE:
<223> OTHER INFORMATION: Synthetically generated SARS CoV S peptide

<400> SEQUENCE: 89

Ala Trp Glu Arg Lys Lys Ile Ser Asn Cys Val Ala Asp Tyr Ser
1 5 10 15

<210> SEQ ID NO 90
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 90

Lys Ile Ser Asn Cys Val Ala Asp Tyr Ser Val Leu Tyr Asn Ser
1 5 10 15

<210> SEQ ID NO 91
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 91

Val Ala Asp Tyr Ser Val Leu Tyr Asn Ser Thr Phe Phe Ser Thr
1 5 10 15

<210> SEQ ID NO 92
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 92

Val Leu Tyr Asn Ser Thr Phe Phe Ser Thr Phe Lys Cys Tyr Gly
1 5 10 15

<210> SEQ ID NO 93
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 93

Thr Phe Phe Ser Thr Phe Lys Cys Tyr Gly Val Ser Ala Thr Lys
1 5 10 15

<210> SEQ ID NO 94
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 94

Phe Lys Cys Tyr Gly Val Ser Ala Thr Lys Leu Asn Asp Leu Cys
1 5 10 15

<210> SEQ ID NO 95
<211> LENGTH: 15
<212> TYPE: PRT
<213> ORGANISM: Artificial Sequence
<220> FEATURE:

-continued

<223> OTHER INFORMATION: Synthetically generated SARS CoV S peptide

<400> SEQUENCE: 95

Val Ser Ala Thr Lys Leu Asn Asp Leu Cys Phe Ser Asn Val Tyr
1 5 10 15

<210> SEQ ID NO 96
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 96

Leu Asn Asp Leu Cys Phe Ser Asn Val Tyr Ala Asp Ser Phe Val
1 5 10 15

<210> SEQ ID NO 97
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 97

Phe Ser Asn Val Tyr Ala Asp Ser Phe Val Val Lys Gly Asp Asp
1 5 10 15

<210> SEQ ID NO 98
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 98

Ala Asp Ser Phe Val Val Lys Gly Asp Asp Val Arg Gln Ile Ala
1 5 10 15

<210> SEQ ID NO 99
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 99

Val Lys Gly Asp Asp Val Arg Gln Ile Ala Pro Gly Gln Thr Gly
1 5 10 15

<210> SEQ ID NO 100
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 100

Val Arg Gln Ile Ala Pro Gly Gln Thr Gly Val Ile Ala Asp Tyr
1 5 10 15

<210> SEQ ID NO 101
<211> LENGTH: 15
<212> TYPE: PRT
<213> ORGANISM: Artificial Sequence
<220> FEATURE:
<223> OTHER INFORMATION: Synthetically generated SARS CoV S peptide -continued

<400> SEQUENCE: 101

Pro Gly Gln Thr Gly Val Ile Ala Asp Tyr Asn Tyr Lys Leu Pro
1 5 10 15

<210> SEQ ID NO 102
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 102

Val Ile Ala Asp Tyr Asn Tyr Lys Leu Pro Asp Asp Phe Met Gly
1 5 10 15

<210> SEQ ID NO 103
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 103

Asn Tyr Lys Leu Pro Asp Asp Phe Met Gly Cys Val Leu Ala Trp
1 5 10 15

<210> SEQ ID NO 104
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 104

Asp Asp Phe Met Gly Cys Val Leu Ala Trp Asn Thr Arg Asn Ile
1 5 10 15

<210> SEQ ID NO 105
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 105

Cys Val Leu Ala Trp Asn Thr Arg Asn Ile Asp Ala Thr Ser Thr
1 5 10 15

<210> SEQ ID NO 106
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 106

Asn Thr Arg Asn Ile Asp Ala Thr Ser Thr Gly Asn Tyr Asn Tyr
1 5 10 15

<210> SEQ ID NO 107
<211> LENGTH: 15
<212> TYPE: PRT
<213> ORGANISM: Artificial Sequence
<220> FEATURE:
<223> OTHER INFORMATION: Synthetically generated SARS CoV S peptide -continued

<400> SEQUENCE: 107

Asp Ala Thr Ser Thr Gly Asn Tyr Asn Tyr Lys Tyr Arg Tyr Leu
1 5 10 15

<210> SEQ ID NO 108
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 108

Gly Asn Tyr Asn Tyr Lys Tyr Arg Tyr Leu Arg His Gly Lys Leu
1 5 10 15

<210> SEQ ID NO 109
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 109

Lys Tyr Arg Tyr Leu Arg His Gly Lys Leu Arg Pro Phe Glu Arg
1 5 10 15

<210> SEQ ID NO 110
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 110

Arg His Gly Lys Leu Arg Pro Phe Glu Arg Asp Ile Ser Asn Val
1 5 10 15

<210> SEQ ID NO 111
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 111

Arg Pro Phe Glu Arg Asp Ile Ser Asn Val Pro Phe Ser Pro Asp
1 5 10 15

<210> SEQ ID NO 112
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 112

Asp Ile Ser Asn Val Pro Phe Ser Pro Asp Gly Lys Pro Cys Thr
1 5 10 15

<210> SEQ ID NO 113
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 113

-continued

Pro Phe Ser Pro Asp Gly Lys Pro Cys Thr Pro Pro Ala Leu Asn
1 5 10 15

<210> SEQ ID NO 114
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 114

Gly Lys Pro Cys Thr Pro Pro Ala Leu Asn Cys Tyr Trp Pro Leu
1 5 10 15

<210> SEQ ID NO 115
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 115

Pro Pro Ala Leu Asn Cys Tyr Trp Pro Leu Asn Asp Tyr Gly Phe
1 5 10 15

<210> SEQ ID NO 116
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 116

Cys Tyr Trp Pro Leu Asn Asp Tyr Gly Phe Tyr Thr Thr Thr Gly
1 5 10 15

<210> SEQ ID NO 117
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 117

Asn Asp Tyr Gly Phe Tyr Thr Thr Thr Gly Ile Gly Tyr Gln Pro
1 5 10 15

<210> SEQ ID NO 118
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 118

Tyr Thr Thr Thr Gly Ile Gly Tyr Gln Pro Tyr Arg Val Val Val
1 5 10 15

<210> SEQ ID NO 119
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 119

-continued

Ile Gly Tyr Gln Pro Tyr Arg Val Val Val Leu Ser Phe Glu Leu
1 5 10 15

<210> SEQ ID NO 120
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 120

Tyr Arg Val Val Val Leu Ser Phe Glu Leu Leu Asn Ala Pro Ala
1 5 10 15

<210> SEQ ID NO 121
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 121

Leu Ser Phe Glu Leu Leu Asn Ala Pro Ala Thr Val Cys Gly Pro
1 5 10 15

<210> SEQ ID NO 122
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 122

Leu Asn Ala Pro Ala Thr Val Cys Gly Pro Lys Leu Ser Thr Asp
1 5 10 15

<210> SEQ ID NO 123
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 123

Thr Val Cys Gly Pro Lys Leu Ser Thr Asp Leu Ile Lys Asn Gln
1 5 10 15

<210> SEQ ID NO 124
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 124

Lys Leu Ser Thr Asp Leu Ile Lys Asn Gln Cys Val Asn Phe Asn
1 5 10 15

<210> SEQ ID NO 125
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 125

Leu Ile Lys Asn Gln Cys Val Asn Phe Asn Phe Asn Gly Leu Thr

-continued 1 5 10 15

<210> SEQ ID NO 126
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 126

Cys Val Asn Phe Asn Phe Asn Gly Leu Thr Gly Thr Gly Val Leu
1 5 10 15

<210> SEQ ID NO 127
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 127

Phe Asn Gly Leu Thr Gly Thr Gly Val Leu Thr Pro Ser Ser Lys
1 5 10 15

<210> SEQ ID NO 128
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 128

Gly Thr Gly Val Leu Thr Pro Ser Ser Lys Arg Phe Gln Pro Phe
1 5 10 15

<210> SEQ ID NO 129
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 129

Thr Pro Ser Ser Lys Arg Phe Gln Pro Phe Gln Gln Phe Gly Arg
1 5 10 15

<210> SEQ ID NO 130
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 130

Arg Phe Gln Pro Phe Gln Gln Phe Gly Arg Asp Val Ser Asp Phe
1 5 10 15

<210> SEQ ID NO 131
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 131

Gln Gln Phe Gly Arg Asp Val Ser Asp Phe Thr Asp Ser Val Arg
1 5 10 15

-continued

<210> SEQ ID NO 132
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 132

Asp Val Ser Asp Phe Thr Asp Ser Val Arg Asp Pro Lys Thr Ser
1 5 10 15

<210> SEQ ID NO 133
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 133

Thr Asp Ser Val Arg Asp Pro Lys Thr Ser Glu Ile Leu Asp Ile
1 5 10 15

<210> SEQ ID NO 134
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 134

Asp Pro Lys Thr Ser Glu Ile Leu Asp Ile Ser Pro Cys Ala Phe
1 5 10 15

<210> SEQ ID NO 135
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 135

Glu Ile Leu Asp Ile Ser Pro Cys Ala Phe Gly Gly Val Ser Val
1 5 10 15

<210> SEQ ID NO 136
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 136

Ser Pro Cys Ala Phe Gly Gly Val Ser Val Ile Thr Pro Gly Thr
1 5 10 15

<210> SEQ ID NO 137
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 137

Gly Gly Val Ser Val Ile Thr Pro Gly Thr Asn Ala Ser Ser Glu
1 5 10 15

-continued

<210> SEQ ID NO 138
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 138

Ile Thr Pro Gly Thr Asn Ala Ser Ser Glu Val Ala Val Leu Tyr
1 5 10 15

<210> SEQ ID NO 139
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 139

Asn Ala Ser Ser Glu Val Ala Val Leu Tyr Gln Asp Val Asn Cys
1 5 10 15

<210> SEQ ID NO 140
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 140

Val Ala Val Leu Tyr Gln Asp Val Asn Cys Thr Asp Val Ser Thr
1 5 10 15

<210> SEQ ID NO 141
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 141

Gln Asp Val Asn Cys Thr Asp Val Ser Thr Ala Ile His Ala Asp
1 5 10 15

<210> SEQ ID NO 142
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 142

Thr Asp Val Ser Thr Ala Ile His Ala Asp Gln Leu Thr Pro Ala
1 5 10 15

<210> SEQ ID NO 143
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 143

Ala Ile His Ala Asp Gln Leu Thr Pro Ala Trp Arg Ile Tyr Ser
1 5 10 15

-continued

<210> SEQ ID NO 144
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 144

Gln Leu Thr Pro Ala Trp Arg Ile Tyr Ser Thr Gly Asn Asn Val
1 5 10 15

<210> SEQ ID NO 145
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 145

Trp Arg Ile Tyr Ser Thr Gly Asn Asn Val Phe Gln Thr Gln Ala
1 5 10 15

<210> SEQ ID NO 146
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 146

Thr Gly Asn Asn Val Phe Gln Thr Gln Ala Gly Cys Leu Ile Gly
1 5 10 15

<210> SEQ ID NO 147
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 147

Phe Gln Thr Gln Ala Gly Cys Leu Ile Gly Ala Glu His Val Asp
1 5 10 15

<210> SEQ ID NO 148
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 148

Gly Cys Leu Ile Gly Ala Glu His Val Asp Thr Ser Tyr Glu Cys
1 5 10 15

<210> SEQ ID NO 149
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 149

Ala Glu His Val Asp Thr Ser Tyr Glu Cys Asp Ile Pro Ile Gly
1 5 10 15

<210> SEQ ID NO 150

-continued

<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 150

Thr Ser Tyr Glu Cys Asp Ile Pro Ile Gly Ala Gly Ile Cys Ala
1 5 10 15

<210> SEQ ID NO 151
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 151

Asp Ile Pro Ile Gly Ala Gly Ile Cys Ala Ser Tyr His Thr Val
1 5 10 15

<210> SEQ ID NO 152
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 152

Ala Gly Ile Cys Ala Ser Tyr His Thr Val Ser Leu Leu Arg Ser
1 5 10 15

<210> SEQ ID NO 153
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 153

Ser Tyr His Thr Val Ser Leu Leu Arg Ser Thr Ser Gln Lys Ser
1 5 10 15

<210> SEQ ID NO 154
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 154

Ser Leu Leu Arg Ser Thr Ser Gln Lys Ser Ile Val Ala Tyr Thr
1 5 10 15

<210> SEQ ID NO 155
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 155

Thr Ser Gln Lys Ser Ile Val Ala Tyr Thr Met Ser Leu Gly Ala
1 5 10 15

<210> SEQ ID NO 156
<211> LENGTH: 15

-continued

<212> TYPE: PRT
<213> ORGANISM: Artificial Sequence
<220> FEATURE:
<223> OTHER INFORMATION: Synthetically generated SARS CoV S peptide

<400> SEQUENCE: 156

Ile Val Ala Tyr Thr Met Ser Leu Gly Ala Asp Ser Ser Ile Ala
1 5 10 15

<210> SEQ ID NO 157
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 157

Met Ser Leu Gly Ala Asp Ser Ser Ile Ala Tyr Ser Asn Asn Thr
1 5 10 15

<210> SEQ ID NO 158
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 158

Asp Ser Ser Ile Ala Tyr Ser Asn Asn Thr Ile Ala Ile Pro Thr
1 5 10 15

<210> SEQ ID NO 159
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 159

Tyr Ser Asn Asn Thr Ile Ala Ile Pro Thr Asn Phe Ser Ile Ser
1 5 10 15

<210> SEQ ID NO 160
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 160

Ile Ala Ile Pro Thr Asn Phe Ser Ile Ser Ile Thr Thr Glu Val
1 5 10 15

<210> SEQ ID NO 161
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 161

Asn Phe Ser Ile Ser Ile Thr Thr Glu Val Met Pro Val Ser Met
1 5 10 15

<210> SEQ ID NO 162
<211> LENGTH: 15
<212> TYPE: PRT

-continued

<213> ORGANISM: Artificial Sequence
<220> FEATURE:
<223> OTHER INFORMATION: Synthetically generated SARS CoV S peptide

<400> SEQUENCE: 162

Ile Thr Thr Glu Val Met Pro Val Ser Met Ala Lys Thr Ser Val
1 5 10 15

<210> SEQ ID NO 163
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 163

Met Pro Val Ser Met Ala Lys Thr Ser Val Asp Cys Asn Met Tyr
1 5 10 15

<210> SEQ ID NO 164
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 164

Ala Lys Thr Ser Val Asp Cys Asn Met Tyr Ile Cys Gly Asp Ser
1 5 10 15

<210> SEQ ID NO 165
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 165

Asp Cys Asn Met Tyr Ile Cys Gly Asp Ser Thr Glu Cys Ala Asn
1 5 10 15

<210> SEQ ID NO 166
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 166

Asp Ser Phe Lys Glu Glu Leu Asp Lys Tyr Phe Lys Asn His Thr
1 5 10 15

<210> SEQ ID NO 167
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 167

Glu Leu Asp Lys Tyr Phe Lys Asn His Thr Ser Pro Asp Val Asp
1 5 10 15

<210> SEQ ID NO 168
<211> LENGTH: 15
<212> TYPE: PRT
<213> ORGANISM: Artificial Sequence -continued
<220> FEATURE:
<223> OTHER INFORMATION: Synthetically generated SARS CoV S peptide

<400> SEQUENCE: 168

Phe Lys Asn His Thr Ser Pro Asp Val Asp Leu Gly Asp Ile Ser
1 5 10 15

<210> SEQ ID NO 169
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 169

Ser Pro Asp Val Asp Leu Gly Asp Ile Ser Gly Ile Asn Ala Ser
1 5 10 15

<210> SEQ ID NO 170
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 170

Leu Gly Asp Ile Ser Gly Ile Asn Ala Ser Val Val Asn Ile Gln
1 5 10 15

<210> SEQ ID NO 171
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 171

Gly Ile Asn Ala Ser Val Val Asn Ile Gln Lys Glu Ile Asp Arg
1 5 10 15

<210> SEQ ID NO 172
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 172

Val Val Asn Ile Gln Lys Glu Ile Asp Arg Leu Asn Glu Val Ala
1 5 10 15

<210> SEQ ID NO 173
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 173

Lys Glu Ile Asp Arg Leu Asn Glu Val Ala Lys Asn Leu Asn Glu
1 5 10 15

<210> SEQ ID NO 174
<211> LENGTH: 15
<212> TYPE: PRT
<213> ORGANISM: Artificial Sequence
<220> FEATURE:

-continued

<223> OTHER INFORMATION: Synthetically generated SARS CoV S peptide

<400> SEQUENCE: 174

Leu Asn Glu Val Ala Lys Asn Leu Asn Glu Ser Leu Ile Asp Leu
1 5 10 15

<210> SEQ ID NO 175
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 175

Lys Asn Leu Asn Glu Ser Leu Ile Asp Leu Gln Glu Leu Gly Lys
1 5 10 15

<210> SEQ ID NO 176
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 176

Ser Leu Ile Asp Leu Gln Glu Leu Gly Lys Tyr Glu Gln Tyr Ile
1 5 10 15

<210> SEQ ID NO 177
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 177

Gln Glu Leu Gly Lys Tyr Glu Gln Tyr Ile Lys Trp Pro Trp Tyr
1 5 10 15

<210> SEQ ID NO 178
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 178

Tyr Glu Gln Tyr Ile Lys Trp Pro Trp Tyr Val Trp Leu Gly Phe
1 5 10 15

<210> SEQ ID NO 179
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 179

Lys Trp Pro Trp Tyr Val Trp Leu Gly Phe Ile Ala Gly Leu Ile
1 5 10 15

<210> SEQ ID NO 180
<211> LENGTH: 15
<212> TYPE: PRT
<213> ORGANISM: Artificial Sequence
<220> FEATURE:
<223> OTHER INFORMATION: Synthetically generated SARS CoV S peptide -continued

<400> SEQUENCE: 180

Val Trp Leu Gly Phe Ile Ala Gly Leu Ile Ala Ile Val Met Val
1 5 10 15

<210> SEQ ID NO 181
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 181

Ile Ala Gly Leu Ile Ala Ile Val Met Val Thr Ile Leu Leu Cys
1 5 10 15

<210> SEQ ID NO 182
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 182

Ala Ile Val Met Val Thr Ile Leu Leu Cys Cys Met Thr Ser Cys
1 5 10 15

<210> SEQ ID NO 183
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 183

Thr Ile Leu Leu Cys Cys Met Thr Ser Cys Cys Ser Cys Leu Lys
1 5 10 15

<210> SEQ ID NO 184
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 184

Cys Met Thr Ser Cys Cys Ser Cys Leu Lys Gly Ala Cys Ser Cys
1 5 10 15

<210> SEQ ID NO 185
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 185

Cys Ser Cys Leu Lys Gly Ala Cys Ser Cys Gly Ser Cys Cys Lys
1 5 10 15

<210> SEQ ID NO 186
<211> LENGTH: 15
<212> TYPE: PRT
<213> ORGANISM: Artificial Sequence
<220> FEATURE:
<223> OTHER INFORMATION: Synthetically generated SARS CoV S peptide -continued

<400> SEQUENCE: 186

Gly Ala Cys Ser Cys Gly Ser Cys Cys Lys Phe Asp Glu Asp Asp
1 5 10 15

<210> SEQ ID NO 187
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 187

Gly Ser Cys Cys Lys Phe Asp Glu Asp Asp Ser Glu Pro Val Leu
1 5 10 15

<210> SEQ ID NO 188
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 188

Phe Asp Glu Asp Asp Ser Glu Pro Val Leu Lys Gly Val Lys Leu
1 5 10 15

<210> SEQ ID NO 189
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 189

Gly Asp Ser Thr Glu Cys Ala Asn Leu Leu Leu Gln Tyr Gly Ser
1 5 10 15

<210> SEQ ID NO 190
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 190

Leu Gln Tyr Gly Ser Phe Cys Thr Gln Leu Asn Arg Ala Leu Ser
1 5 10 15

<210> SEQ ID NO 191
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 191

Asn Arg Ala Leu Ser Gly Ile Ala Ala Glu Gln Asp Arg Asn Thr
1 5 10 15

<210> SEQ ID NO 192
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 192

-continued

Gln Asp Arg Asn Thr Arg Glu Val Phe Ala Gln Val Lys Gln Met
1 5 10 15

<210> SEQ ID NO 193
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 193

Gln Val Lys Gln Met Tyr Lys Thr Pro Thr Leu Lys Tyr Phe Gly
1 5 10 15

<210> SEQ ID NO 194
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 194

Leu Lys Tyr Phe Gly Gly Phe Asn Phe Ser Gln Ile Leu Pro Asp
1 5 10 15

<210> SEQ ID NO 195
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 195

Gln Ile Leu Pro Asp Pro Leu Lys Pro Thr Lys Arg Ser Phe Ile
1 5 10 15

<210> SEQ ID NO 196
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 196

Lys Arg Ser Phe Ile Glu Asp Leu Leu Phe Asn Lys Val Thr Leu
1 5 10 15

<210> SEQ ID NO 197
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 197

Lys Val Thr Leu Leu Ala Asp Ala Gly Phe Met Lys Gln Tyr Gly
1 5 10 15

<210> SEQ ID NO 198
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 198

-continued

Met Lys Gln Tyr Gly Glu Cys Leu Gly Asp Ile Asn Ala Arg Asp
1 5 10 15

<210> SEQ ID NO 199
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 199

Ile Asn Ala Arg Asp Leu Ile Cys Ala Gln Lys Phe Asn Gly Leu
1 5 10 15

<210> SEQ ID NO 200
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 200

Lys Phe Asn Gly Leu Thr Val Leu Pro Pro Leu Leu Thr Asp Asp
1 5 10 15

<210> SEQ ID NO 201
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 201

Leu Leu Thr Asp Asp Met Ile Ala Ala Tyr Thr Ala Ala Leu Val
1 5 10 15

<210> SEQ ID NO 202
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 202

Thr Ala Ala Leu Val Ser Gly Thr Ala Thr Ala Gly Trp Thr Phe
1 5 10 15

<210> SEQ ID NO 203
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 203

Ala Gly Trp Thr Phe Gly Ala Gly Ala Ala Leu Gln Ile Pro Phe
1 5 10 15

<210> SEQ ID NO 204
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 204

Leu Gln Ile Pro Phe Ala Met Gln Met Ala Tyr Arg Phe Asn Gly

-continued 1 5 10 15

<210> SEQ ID NO 205
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 205

Tyr Arg Phe Asn Gly Ile Gly Val Thr Gln Asn Val Leu Tyr Glu
1 5 10 15

<210> SEQ ID NO 206
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 206

Asn Val Leu Tyr Glu Asn Gln Lys Gln Ile Ala Asn Gln Phe Asn
1 5 10 15

<210> SEQ ID NO 207
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 207

Ala Asn Gln Phe Asn Lys Ala Ile Ser Gln Ile Gln Glu Ser Leu
1 5 10 15

<210> SEQ ID NO 208
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 208

Ile Gln Glu Ser Leu Thr Thr Thr Ser Thr Ala Leu Gly Lys Leu
1 5 10 15

<210> SEQ ID NO 209
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 209

Ala Leu Gly Lys Leu Gln Asp Val Val Asn Gln Asn Ala Gln Ala
1 5 10 15

<210> SEQ ID NO 210
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 210

Gln Asn Ala Gln Ala Leu Asn Thr Leu Val Lys Gln Leu Ser Ser
1 5 10 15

-continued

<210> SEQ ID NO 211
<211> LENGTH: 15
<212> TYPE: PRT
<213> ORGANISM: Artificial Sequence
<220> FEATURE:
<223> OTHER INFORMATION: Synthetically generated SARS CoV S peptide

<400> SEQUENCE: 211

Lys Gln Leu Ser Ser Asn Phe Gly Ala Ile Ser Ser Val Leu Asn
1 5 10 15

<210> SEQ ID NO 212
<211> LENGTH: 16
<212> TYPE: PRT
<213> ORGANISM: Artificial Sequence
<220> FEATURE:
<223> OTHER INFORMATION: Synthetically generated SARS CoV S peptide

<400> SEQUENCE: 212

Ser Ser Val Leu Asn Asp Ile Leu Ser Arg Leu Asp Lys Val Glu Ala
1 5 10 15

<210> SEQ ID NO 213
<211> LENGTH: 16
<212> TYPE: PRT
<213> ORGANISM: Artificial Sequence
<220> FEATURE:
<223> OTHER INFORMATION: Synthetically generated SARS CoV S peptide

<400> SEQUENCE: 213

Leu Asp Lys Val Glu Ala Glu Val Gln Ile Asp Arg Leu Ile Thr Gly
1 5 10 15

<210> SEQ ID NO 214
<211> LENGTH: 21
<212> TYPE: PRT
<213> ORGANISM: Artificial Sequence
<220> FEATURE:
<223> OTHER INFORMATION: Synthetically generated SARS CoV S peptide

<400> SEQUENCE: 214

Arg Leu Ile Thr Gly Arg Leu Gln Ser Leu Gln Thr Tyr Val Thr Gln
1 5 10 15

Gln Leu Ile Arg Ala
20

RECEPTOR BINDING POLYPEPTIDES

RELATED APPLICATION

This application claims priority to U.S. Provisional Application Ser. No. 60/535,641, filed on Jan. 9, 2004, the content of which is incorporated by reference in its entirety.

Please insert official copy (copy 2) of sequence listing on the compact disc which has the file name US 11/033,455txt, contains 204 KB, and created on Jun. 10, 2005, is hereby incorporated by reference in to the specification following the Abstract

BACKGROUND

Virus is the cause of various disorders. For example, members of the coronavirus family cause hepatitis in mice, gastroenteritis in pigs, and respiratory infections in birds and humans. Among the more than 30 strains isolated so far, three or four infect humans. The severe acute respiratory syndrome (SARS), a newly found infectious disease, is associated with a novel coronavirus. This life-threatening respiratory coronavirus touched off worldwide outbreaks in 2003. Vaccines and drugs against SARS coronavirus (CoV) are being vigorously sought. Nevertheless, the progress has been rather slow due to safety concerns.

SUMMARY

This invention is based, at least in part, on the discovery of receptor binding domains of the SARS CoV Spike (S) protein. Genomic sequences of a number of SARS CoV strains can be found in GenBank. GenBank Accession No. AY278741 (SEQ ID NO: 1) represents the genomic sequence of the SARS CoV Urbani strain, which contains an open reading frame encoding a polypeptide that is 7,073 amino acid residues (aa.) in length (SEQ ID NO: 2). The nucleic acid encoding the S protein of this strain corresponds to nucleotides (nt) 21,492-25,259 of GenBank Accession No. AY278741. Listed below are the nucleic acid and amino acid sequences of the S protein:

```
21492            atgtttatt ttcttattat ttcttactct cactagtggt agtgaccttg
21541 accggtgcac cacttttgat gatgttcaag ctcctaatta cactcaacat acttcatcta
21601 tgagggggt ttactatcct gatgaaattt ttagatcaga cactctttat ttaactcagg
21661 atttatttct tccattttat tctaatgtta cagggtttca tactattaat catacgtttg
21721 gcaaccctgt catacctttt aaggatggta tttattttgc tgccacagag aaatcaaatg
21781 ttgtccgtgg ttgggttttt ggttctacca tgaacaacaa gtcacagtcg gtgattatta
21841 ttaacaattc tactaatgtt gttatacgag catgtaactt tgaattgtgt gacaaccctt
21901 tctttgctgt ttctaaaccc atgggtacac agacacatac tatgatattc gataatgcat
21961 ttaattgcac tttcgagtac atatctgatg ccttttcgct tgatgtttca gaaaagtcag
22021 gtaattttaa acacttacga gagtttgtgt ttaaaaataa agatgggttt ctctatgttt
22081 ataagggcta tcaacctata gatgtagttc gtgatctacc ttctggtttt aacactttga
22141 aacctatttt taagttgcct cttggtatta acattacaaa ttttagagcc attcttacag
22201 ccttttcacc tgctcaagac atttggggca cgtcagctgc agcctatttt gttggctatt
22261 taaagccaac tacatttatg ctcaagtatg atgaaaatgg tacaatcaca gatgctgttg
22321 attgttctca aaatccactt gctgaactca aatgctctgt taagagcttt gagattgaca
22381 aaggaattta ccagacctct aatttcaggg ttgttccctc aggagatgtt gtgagattcc
22441 ctaatattac aaacttgtgt ccttttggag aggtttttaa tgctactaaa ttcccttctg
22501 tctatgcatg ggagagaaaa aaaatttcta attgtgttgc tgattactct gtgctctaca
22561 actcaacatt tttttcaacc tttaagtgct atggcgtttc tgccactaag ttgaatgatc
22621 tttgcttctc caatgtctat gcagattctt ttgtagtcaa gggagatgat gtaagacaaa
22681 tagcgccagg acaaactggt gttattgctg attataatta taaattgcca gatgatttca
22741 tgggttgtgt ccttgcttgg aatactagga acattgatgc tacttcaact ggtaattata
22801 attataaata taggtatctt agacatggca agcttaggcc ctttgagaga gacatatcta
22861 atgtgccttt ctcccctgat ggcaaacctt gcaccccacc tgctcttaat tgttattggc
22921 cattaaatga ttatggtttt tacaccacta ctggcattgg ctaccaacct tacagagttg
22981 tagtactttc ttttgaactt ttaaatgcac cggccacggt ttgtggacca aaattatcca
23041 ctgaccttat taagaaccag tgtgtcaatt ttaattttaa tggactcact ggtactggtg
```

-continued 23101 tgttaactcc ttcttcaaag agatttcaac catttcaaca atttggccgt gatgtttctg
23161 atttcactga ttccgttcga gatcctaaaa catctgaaat attagacatt tcaccttgct
23221 cttttggggg tgtaagtgta attacacctg gaacaaatgc ttcatctgaa gttgctgttc
23281 tatatcaaga tgttaactgc actgatgttt ctacagcaat tcatgcagat caactcacac
23341 cagcttggcg catatattct actggaaaca atgtattcca gactcaagca ggctgtctta
23401 taggagctga gcatgtcgac acttcttatg agtgcgacat tcctattgga gctggcattt
23461 gtgctagtta ccatacagtt tctttattac gtagtactag ccaaaaatct attgtggctt
23521 atactatgtc tttaggtgct gatagttcaa ttgcttactc taataacacc attgctatac
23581 ctactaactt ttcaattagc attactacag aagtaatgcc tgtttctatg gctaaaacct
23641 ccgtagattg taatatgtac atctgcggag attctactga atgtgctaat ttgcttctcc
23701 aatatggtag cttttgcaca caactaaatc gtgcactctc aggtattgct gctgaacagg
23761 atcgcaacac acgtgaagtg ttcgctcaag tcaaacaaat gtacaaaacc ccaactttga
23821 aatattttgg tggttttaat ttttcacaaa tattacctga ccctctaaag ccaactaaga
23881 ggtcttttat tgaggacttg ctctttaata aggtgacact cgctgatgct ggcttcatga
23941 agcaatatgg cgaatgccta ggtgatatta atgctagaga tctcatttgt gcgcagaagt
24001 tcaatggact tacagtgttg ccacctctgc tcactgatga tatgattgct gcctacactg
24061 ctgctctagt tagtggtact gccactgctg gatggacatt tggtgctggc gctgctcttc
24121 aaataccttt tgctatgcaa atggcatata ggttcaatgg cattggagtt acccaaaatg
24181 ttctctatga gaaccaaaaa caaatcgcca accaatttaa caaggcgatt agtcaaattc
24241 aagaatcact tacaacaaca tcaactgcat tgggcaagct gcaagacgtt gttaaccaga
24301 atgctcaagc attaaacaca cttgttaaac aacttagctc taattttggt gcaatttcaa
24361 gtgtgctaaa tgatatcctt tcgcgacttg ataaagtcga ggcggaggta caaattgaca
24421 ggttaattac aggcagactt caaagccttc aaacctatgt aacacaacaa ctaatcaggg
24481 ctgctgaaat cagggcttct gctaatcttg ctgctactaa aatgtctgag tgtgttcttg
24541 gacaatcaaa aagagttgac ttttgtggaa agggctacca ccttatgtcc ttcccacaag
24601 cagccccgca tggtgttgtc ttcctacatg tcacgtatgt gccatcccag gagaggaact
24661 tcaccacagc gccagcaatt tgtcatgaag gcaaagcata cttccctcgt gaaggtgttt
24721 ttgtgtttaa tggcacttct tggtttatta cacagaggaa cttcttttct ccacaaataa
24781 ttactacaga caatacattt gtctcaggaa attgtgatgt cgttattggc atcattaaca
24841 acacagttta tgatcctctg caacctgagc tcgactcatt caaagaagag ctggacaagt
24901 acttcaaaaa tcatacatca ccagatgttg atcttggcga catttcaggc attaacgctt
24961 ctgtcgtcaa cattcaaaaa gaaattgacc gcctcaatga ggtcgctaaa aatttaaatg
25021 aatcactcat tgaccttcaa gaattgggaa aatatgagca atatattaaa tggccttggt
25081 atgtttggct cggcttcatt gctggactaa ttgccatcgt catggttaca atcttgcttt
25141 gttgcatgac tagttgttgc agttgcctca agggtgcatg ctcttgtggt tcttgctgca
25201 agtttgatga ggatgactct gagccagttc tcaagggtgt caaattacat tacacataa
25259 (SEQ ID NO:3)

MFIFLLFLTLTSGSDLDRCTTFDDVQAPNYTQHTSSMRGVYYPDEIFRSD
TLYLTQDLFLPFYSNVTGFHTINHTFGNPVIPFKDGIYFAATEKSNVVRG
WVFGSTMNNKSQSVIIINNSTNVVIRACNFELCDNPFFAVSKPMGTQTHTM

-continued

```
IFDNAFNCTFEYISDAFSLDVSEKSGNFKHLREFVFKNKDGGLYVYKGYQP

IDVVRDLPSGFNTLKPIFKLPLGINITNFRAILTAFSPAQDIWGTSAAAYF

VGYLKPTTFMLKYDENGTITDAVDCSQNPLAELKCSVKSFEIDKGIYQTSN

FRVVPSGDVVRFPNITNLCPFGEVFNATKFPSVYAWERKKISNCVADYSVL

YNSTFFSTFKCYGVSATKLNDLCFSNVYADSFVVKGDDVRQIAPGQTGVI

ADYNYKLPDDFMGCVLAWNTRNIDATSTGNYNYKYRYLRHGKLRPFERDI

SNVPFSPDGKPCTPPALNCYWPLNDYGFYTTTGIGYQPYRVVVLSFELLN

APATVCGPKLSTDLIKNQCVNFNFNGLTGTGVLTPSSKRFQPFQQFGRDV

SDFTDSVRDPKTSEILDISPCAFGGVSVITPGTNASSEVAVLYQDVNCTD

VSTAIHADQLTPAWRIYSTGNNVFQTQAGCLIGAEHVDTSYECDIPIGAGI

CASYHTVSLLRSTSQKSIVAYTMSLGADSSIAYSNNTIAIPTNFSISITTE

VMPVSMAKTSVDCNMYICGDSTECANLLLQYGSFCTQLNRALSGIAAEQDR

NTREVFAQVKQMYKTPTLKYFGGFNFSQILPDPLKPTKRSFIEDLLFNKVT

LADAGFMKQYGECLGDINARDLICAQKFNGLTVLPPLLTDDMIAAYTAALV

SGTATAGWTFGAGAALQIPFAMQMAYRFNGIGVTQNVLYENQKQIANQFNK

AISQIQESLTTTSTALGKLQDVVNQNAQALNTLVKQLSSNFGAISSVLNDI

LSRLDKVEAEVQIDRLITGRLQSLQTYVTQQLIRAAEIRASANLAATKMSE

CVLGQSKRVDFCGKGYHLMSFPQAAPHGVVFLHVTYVPSQERNFTTAPAIC

HEGKAYFPREGVFVFNGTSWFITQRNFFSPQIITTDNTFVSGNCDVVIGII

NNTVYDPLQPELDSFKEELDKYFKNHTSPDVDLGDISGINASVVNIQKEI

DRLNEVAKNLNESLIDLQELGKYEQYIKWPWYVWLGFIAGLIAIVMVTILLC

CMTSCCSCLKGACSCGSCCKFDEDDSEPVLKGVKLHYT
(SEQ ID NO:4; the two underlines segments represent two receptor binding
domains.)
```

One aspect of the invention features an isolated polypeptide containing SEQ ID NO: 4 or an immunogenic fragment derived from SEQ ID NO: 4. The immunogenic fragment is at least 10 amino acid residues in length, i.e., any number between 10 and 1255 (the length of SEQ ID NO: 4), inclusive. Examples of such an immunogenic fragment include the domains listed below:

| Domain Name | Corresponding aa. position within SEQ ID NO: 4 | SEQ ID NO |
|---|---|---|
| Receptor binding domain 1 (RBD1) | 80-227 | SEQ ID NO: 6 |
| Receptor binding domain 2 (RBD2) | 284-735 | SEQ ID NO: 8 |
| S1 | 1-333 | SEQ ID NO: 18 |
| S2 | 334-666 | SEQ ID NO: 20 |
| S3 | 667-1000 | SEQ ID NO: 22 |
| RBD2-consensus (RBD2-C) | 434-467 | SEQ ID NO: 24 |
| RBD-55 | 564-613 | SEQ ID NO: 26 |
| Transmembrane domain (TM) | 1128-1255 | SEQ ID NO: 28 |

Examples also include the fusions of two or more of the above-listed domains, e.g., RBD1-$(Gly)_8$-TM (SEQ ID NO: 10), RBD2-$(Gly)_8$-TM (SEQ ID NO: 12), RBD1-$(Gly)_8$-RBD2 (SEQ ID NO: 14), and RBD1-$(Gly)_8$-RBD2-$(Gly)_8$-TM (SEQ ID NO: 16). In these fusions, different S protein fragments are joined by a linker of 8 glycines. Additional examples include those listed in Table 2 shown in Example 6 below. Preferably, the polypeptide of this invention contains SEQ ID NO: 24 or 26. In one embodiment, the polypeptide is a glycoprotein containing a polysaccharide, e.g., a polysaccharide from *S. pneumococcal*. In another embodiment, the polypeptide is a fusion protein including a heterologous polypeptide that contains an Fc portion of an immunoglobin, e.g., an IgG. Preferably, the immunoglobin is IgG1, and more preferably, a human IgG1. The fusion protein can also include a heterologous polypeptide that contains a surface portion of a protein of a pathogen, such as the HA or NA of an influenza virus.

An "isolated polypeptide" refers to a polypeptide substantially free from naturally associated molecules, i.e., it is at least 75% (i.e., any number between 75% and 100%, inclusive) pure by dry weight. Purity can be measured by any appropriate standard method, for example, by column chromatography, polyacrylamide gel electrophoresis, or HPLC analysis. An isolated polypeptide of the invention can be purified from a natural source, produced by recombinant DNA techniques, or by chemical methods. A "heterologous" protein or nucleic acid is one that originates from a foreign species, or, if from the same species, is substantially modified from its original form.

The invention also features an isolated nucleic acid that contains a sequence encoding one of the above-mentioned polypeptides. Examples of the sequence include (1) those encoding S, RBD1, RBD2, S1, S2, S3, RBD-2C, RBD-55, and TM, which, respectively, correspond to nt. 21492-25259, 21729-22172, 22341-23696, 21492-22490, 22491-23489, 23490-24491, 22791-22892, 23181-23330, and 24873-25256 of GenBank Accession No. AY278741 (SEQ ID NOs: 3, 5, 7, 17, 19, 21, 23, 25, and 27, respectively)

Listed below are exemplary sequences that encode fusion proteins RBD1-$(Gly)_8$-TM, RBD2-$(Gly)_8$-TM, RBD1-$(Gly)_8$ -RBD2, and RBD1-$(Gly)_8$-RBD2-$(Gly)_8$-TM (SEQ ID NOs: 9, 11, 13, and 15, respectively; linkers shown in the upper case):

SEQ ID NO:9 catacgtttg gcaaccctgt catacctttt aaggatggta tttattttgc tgccacagag
aaatcaaatg ttgtccgtgg ttgggttttt ggttctacca tgaacaacaa gtcacagtcg
gtgattatta ttaacaattc tactaatgtt gttatacgag catgtaactt tgaattgtgt
gacaaccctt tctttgctgt ttctaaaccc atgggtacac agacacatac tatgatattc
gataatgcat ttaattgcac tttcgagtac atatctgatg ccttttcgct tgatgtttca
gaaaagtcag gtaattttaa acacttacga gagtttgtgt ttaaaaataa agatgggttt
ctctatgttt ataagggcta tcaacctata gatgtagttc gtgatctacc ttctggtttt
aacactttga aacctatttt taagttgcct cttggtatta acattacaaa ttttagagcc
GAATTCGGGG GCGGGGGTGG AGGTGGTGGC tcatt caaagaagag ctggacaagt
acttcaaaaa tcatacatca ccagatgttg atcttggcga catttcaggc attaacgctt
ctgtcgtcaa cattcaaaaa gaaattgacc gcctcaatga ggtcgctaaa aatttaaatg
aatcactcat tgaccttcaa gaattgggaa aatatgagca atatattaaa tggccttggt
atgtttggct cggcttcatt gctggactaa ttgccatcgt catggttaca atcttgcttt
gttgcatgac tagttgttgc agttgcctca agggtgcatg ctcttgtggt tcttgctgca
agtttgatga ggatgactct gagccagttc tcaagggtgt caaattacat tacaca

SEQ ID NO:11 gagattgaca aaggaattta ccagacctct aatttcaggg ttgttccctc aggagatgtt
gtgagattcc ctaatattac aaacttgtgt ccttttggag aggtttttaa tgctactaaa
ttcccttctg tctatgcatg ggagagaaaa aaaatttcta attgtgttgc tgattactct
gtgctctaca actcaacatt tttttcaacc tttaagtgct atggcgtttc tgccactaag
ttgaatgatc tttgcttctc caatgtctat gcagattctt ttgtagtcaa gggagatgat
gtaagacaaa tagcgccagg acaaactggt gttattgctg attataatta taaattgcca
gatgatttca tgggttgtgt ccttgcttgg aatactagga acattgatgc tacttcaact
ggtaattata attataaata taggtatctt agacatggca agcttaggcc ctttgagaga
gacatatcta atgtgccttt ctcccctgat ggcaaacctt gcaccccacc tgctcttaat
tgttattggc cattaaatga ttatggtttt tacaccacta ctggcattgg ctaccaacct
tacagagttg tagtactttc ttttgaactt ttaaatgcac cggccacggt ttgtggacca
aaattatcca ctgaccttat taagaaccag tgtgtcaatt ttaattttaa tggactcact
ggtactggtg tgttaactcc ttcttcaaag agatttcaac catttcaaca atttggccgt
gatgtttctg atttcactga ttccgttcga gatcctaaaa catctgaaat attagacatt
tcaccttgct cttttggggg tgtaagtgta attacacctg gaacaaatgc ttcatctgaa
gttgctgttc tatatcaaga tgttaactgc actgatgttt ctacagcaat tcatgcagat
caactcacac cagcttggcg catatattct actggaaaca atgtattcca gactcaagca
ggctgtctta taggagctga gcatgtcgac acttcttatg agtgcgacat tcctattgga -continued gctggcattt gtgctagtta ccatacagtt tctttattac gtagtactag ccaaaaatct
attgtggctt atactatgtc tttaggtgct gatagttcaa ttgcttactc taataacacc
attgctatac ctactaactt ttcaattagc attactacag aagtaatgcc tgtttctatg
gctaaaacct ccgtagattg taatatgtac atctgcggag attctactga atgtgctaat
ttgcttctcc aatatggGCG GCCGCCTGGG GGCGGGGGTG GAGGTGGTGG Ctcatt
caaagaagag ctggacaagt acttcaaaaa tcatacatca ccagatgttg atcttggcga
catttcaggc attaacgctt ctgtcgtcaa cattcaaaaa gaaattgacc gcctcaatga
ggtcgctaaa aatttaaatg aatcactcat tgaccttcaa gaattgggaa aatatgagca
atatattaaa tggccttggt atgtttggct cggcttcatt gctggactaa ttgccatcgt
catggttaca atcttgcttt gttgcatgac tagttgttgc agttgcctca agggtgcatg
ctcttgtggt tcttgctgca agtttgatga ggatgactct gagccagttc tcaagggtgt
caaattacat tacaca

SEQ ID NO:13 catacgtttg gcaaccctgt catacctttt aaggatggta tttattttgc tgccacagag
aaatcaaatg ttgtccgtgg ttgggttttt ggttctacca tgaacaacaa gtcacagtcg
gtgattatta ttaacaattc tactaatgtt gttatacgag catgtaactt tgaattgtgt
gacaaccctt tctttgctgt ttctaaaccc atgggtacac agacacatac tatgatattc
gataatgcat ttaattgcac tttcgagtac atatctgatg ccttttcgct tgatgtttca
gaaaagtcag gtaattttaa acacttacga gagtttgtgt ttaaaaataa agatgggttt
ctctatgttt ataagggcta tcaacctata gatgtagttc gtgatctacc ttctggtttt
aacactttga aacctatttt taagttgcct cttggtatta acattacaaa ttttagagcc
GAATTCGGGG GCGGGGGTGG AGGTGGTGGC gagattgaca aaggaattta ccagacctct
aatttcaggg ttgttccctc aggagatgtt gtgagattcc ctaatattac aaacttgtgt
ccttttggag aggtttttaa tgctactaaa ttcccttctg tctatgcatg ggagagaaaa
aaaatttcta attgtgttgc tgattactct gtgctctaca actcaacatt tttttcaacc
tttaagtgct atggcgtttc tgccactaag ttgaatgatc tttgcttctc caatgtctat
gcagattctt ttgtagtcaa gggagatgat gtaagacaaa tagcgccagg acaaactggt
gttattgctg attataatta taaattgcca gatgatttca tgggttgtgt ccttgcttgg
aatactagga acattgatgc tacttcaact ggtaattata attataaata taggtatctt
agacatggca agcttaggcc ctttgagaga gacatatcta atgtgccttt ctcccctgat
ggcaaacctt gcaccccacc tgctcttaat tgttattggc cattaaatga ttatggtttt
tacaccacta ctggcattgg ctaccaacct tacagagttg tagtactttc ttttgaactt
ttaaatgcac cggccacggt ttgtggacca aaattatcca ctgaccttat taagaaccag
tgtgtcaatt ttaattttaa tggactcact ggtactggtg tgttaactcc ttcttcaaag
agatttcaac catttcaaca atttggccgt gatgtttctg atttcactga ttccgttcga
gatcctaaaa catctgaaat attagacatt tcaccttgct cttttggggg tgtaagtgta
attacacctg gaacaaatgc ttcatctgaa gttgctgttc tatatcaaga tgttaactgc
actgatgttt ctacagcaat tcatgcagat caactcacac cagcttggcg catatattct
actggaaaca atgtattcca gactcaagca ggctgtctta taggagctga gcatgtcgac
acttcttatg agtgcgacat tcctattgga gctggcattt gtgctagtta ccatacagtt -continued

```
tctttattac gtagtactag ccaaaaatct attgtggctt atactatgtc tttaggtgct
gatagttcaa ttgcttactc taataacacc attgctatac ctactaactt ttcaattagc
attactacag aagtaatgcc tgtttctatg gctaaaacct ccgtagattg taatatgtac
atctgcggag attctactga atgtgctaat ttgcttctcc aatatgg
```

SEQ ID NO:15

```
catacgtttg gcaaccctgt catacctttt aaggatggta tttattttgc tgccacagag
aaatcaaatg ttgtccgtgg ttgggttttt ggttctacca tgaacaacaa gtcacagtcg
gtgattatta ttaacaattc tactaatgtt gttatacgag catgtaactt tgaattgtgt
gacaaccctt tctttgctgt ttctaaaccc atgggtacac agacacatac tatgatattc
gataatgcat ttaattgcac tttcgagtac atatctgatg ccttttcgct tgatgtttca
gaaaagtcag gtaattttaa acacttacga gagtttgtgt ttaaaaataa agatgggttt
ctctatgttt ataagggcta tcaacctata gatgtagttc gtgatctacc ttctggtttt
aacactttga aacctatttt taagttgcct cttggtatta acattacaaa ttttagagcc
GAATTCGGGG GCGGGGGTGG AGGTGGTGGC gagattgaca aaggaattta ccagacctct
aatttcaggg ttgttccctc aggagatgtt gtgagattcc ctaatattac aaacttgtgt
ccttttggag aggtttttaa tgctactaaa ttcccttctg tctatgcatg ggagagaaaa
aaaatttcta attgtgttgc tgattactct gtgctctaca actcaacatt tttttcaacc
tttaagtgct atggcgtttc tgccactaag ttgaatgatc tttgcttctc caatgtctat
gcagattctt ttgtagtcaa gggagatgat gtaagacaaa tagcgccagg acaaactggt
gttattgctg attataatta taaattgcca gatgatttca tgggttgtgt ccttgcttgg
aatactagga acattgatgc tacttcaact ggtaattata attataaata taggtatctt
agacatggca agcttaggcc ctttgagaga gacatatcta atgtgccttt ctcccctgat
ggcaaacctt gcaccccacc tgctcttaat tgttattggc cattaaatga ttatggtttt
tacaccacta ctggcattgg ctaccaacct tacagagttg tagtactttc ttttgaactt
ttaaatgcac cggccacggt ttgtggacca aaattatcca ctgaccttat taagaaccag
tgtgtcaatt ttaattttaa tggactcact ggtactggtg tgttaactcc ttcttcaaag
agatttcaac catttcaaca atttggccgt gatgtttctg atttcactga ttccgttcga
gatcctaaaa catctgaaat attagacatt tcaccttgct cttttggggg tgtaagtgta
attacacctg gaacaaatgc ttcatctgaa gttgctgttc tatatcaaga tgttaactgc
actgatgttt ctacagcaat tcatgcagat caactcacac cagcttggcg catatattct
actggaaaca atgtattcca gactcaagca ggctgtctta taggagctga gcatgtcgac
acttcttatg agtgcgacat tcctattgga gctggcattt gtgctagtta ccatacagtt
tctttattac gtagtactag ccaaaaatct attgtggctt atactatgtc tttaggtgct
gatagttcaa ttgcttactc taataacacc attgctatac ctactaactt ttcaattagc
attactacag aagtaatgcc tgtttctatg gctaaaacct ccgtagattg taatatgtac
atctgcggag attctactga atgtgctaat ttgcttctcc aatatggGCG GCCGCCTGGG
GGCGGGGGTG GAGGTGGTGG Ctcatt     caaagaagag ctggacaagt acttcaaaaa
tcatacatca ccagatgttg atcttggcga catttcaggc attaacgctt ctgtcgtcaa
cattcaaaaa gaaattgacc gcctcaatga ggtcgctaaa aatttaaatg aatcactcat
tgaccttcaa gaattgggaa aatatgagca atatattaaa tggccttggt atgtttggct
```

-continued

```
cggcttcatt gctggactaa ttgccatcgt catggttaca atcttgcttt gttgcatgac

tagttgttgc agttgcctca agggtgcatg ctcttgtggt tcttgctgca agtttgatga

ggatgactct gagccagttc tcaagggtgt caaattacat tacaca
```

Additional examples of the nucleic acid of this invention include nucleic acids encoding the peptides listed in Table 2. In a preferred embodiment, the nucleic acid contains SEQ ID NO: 23 or 25.

A "nucleic acid" refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The nucleic acid described above can be used to express the polypeptide of this invention. For this purpose, one can operatively linked the nucleic acid to suitable regulatory sequences to generate an expression vector.

A "vector" refers to a nucleic acid molecule capable of transporting another nucleic acid to which it has been linked. The vector can be capable of autonomous replication or integrate into a host DNA. Examples of the vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. A "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vector can be introduced into host cells to produce the polypeptide of this invention. Also within the scope of this invention is a host cell that contains the above-described nucleic acid. Examples include *E. coli* cells, insect cells (e.g., using baculovirus expression vectors), yeast cells, or mammalian cells. See e.g., Goeddel, (1990) Gene Expression Technology: Methods in Enzymology 185, Academic Press, San Diego, Calif. To produce a polypeptide of this invention, one can culture a host cell in a medium under conditions permitting expression of the polypeptide encoded by a nucleic acid of this invention, and purify the polypeptide from the cultured cell or the medium of the cell. Alternatively, the nucleic acid of this invention can be transcribed and translated in vitro, for example, using T7 promoter regulatory sequences and T7 polymerase.

A polypeptide and a nucleic acid of this invention can be used to induce an immune response (i.e., the production of specific antibodies) in a subject against a coronavirus by administering to the subject an effective amount of the polypeptide or nucleic acid encoding the polypeptide. They also can be used to generate specific antibodies that bind specifically to a polypeptide having the sequence of SEQ ID NO: 4 or its fragment. More specifically, one can generate the antibodies by administering to a non-human animal the polypeptide or nucleic acid. Thus, within the scope of this invention is a composition containing the afore-mentioned polypeptide or nucleic acid; and a pharmaceutically acceptable carrier. The composition can be used to generate the antibodies. One can purify the antibodies from the subject or the non-human animal and generate monoclonal antibodies by standard techniques.

One can use the just-described antibodies to diagnose an infection with a coronavirus, e.g., SARS-CoV, in a subject by determining the presence of a polypeptide containing the sequence of SEQ ID NO: 4 or an immunogenic fragment thereof in a test sample from the subject. Presence of the polypeptide in the test sample indicates the subject is infected with the coronavirus. One can also diagnose an infection with a coronavirus in a subject by determining presence of a specific antibody against a polypeptide having the sequence of SEQ ID NO: 4 or an immunogenic fragment thereof in the test sample. Presence of the antibody in the test sample also indicates the subject is infected with the coronavirus.

Also within the scope of this invention is a method of treating an infection with a coronavirus. The method includes administering to a subject in need thereof an effective amount of one or more of the above-described polypeptides or antibodies. The term "treating" is defined as administration of a composition to a subject with the purpose to cure, alleviate, relieve, remedy, prevent, or ameliorate a disorder, the symptom of the disorder, the disease state secondary to the disorder, or the predisposition toward the disorder. An "effective amount" is an amount of the composition that is capable of producing a medically desirable result, e.g., as described above, in a treated subject.

The details of one or more embodiments of the invention are set forth in the accompanying description below. Other advantages, features, and objects of the invention will be apparent from the detailed description and the claims.

DETAILED DESCRIPTION

This invention relates to receptor binding domains or immunogenic fragments of the S protein of a coronavirus, such as SARS. Since these domains mediate target cell binding and entry of the coronavirus or induce immune response, they can be targeted for diagnosing or treating an infection with the coronavirus.

A polypeptide of this invention contains the sequence of the S protein, such as SEQ ID NO: 4 or an immunogenic fragment thereof. It can also contain the sequence of the S protein of SARS CoV TW1, Tor-2, SIN2500, SIN2774, SIN2748, SIN2677, SIN2679, CUHK-W1, HKU39849, GZ01, BJ01, BJ02, BJ03 BJ04, and other strains. In a particular embodiment, the polypeptide contains a receptor-binding domain of the S protein or a functional equivalent. A functional equivalent of the a protein receptor binding domain refers to a polypeptide derived from the coronavirus S protein, e.g., a fusion polypeptide or a polypeptide having one or more point mutations, insertions, deletions, truncations, or a combination thereof. In particular, such functional equivalents include polypeptides, whose sequences differ from the S protein by one or more conservative amino acid substitutions or by one or more non-conservative amino acid substitutions, deletions, or insertions. Such a functional equivalent can be encoded by a nucleic acid that hybridizes under high stringency conditions to a probe the sequence of which consists of SEQ ID NO: 3, 5, 7, 9, 11, 13, 15, 17, 19, 21, 23, or 25. The term “hybridizes under stringent conditions” refers to conditions for hybridization in 6× sodium chloride/sodium citrate (SSC) at about 45° C., followed by one or more washes in 0.2×SSC, 0.1% SDS at 50-65° C. All of the above-described functional equivalents retain substantially the receptor binding activity of coronavirus, e.g., SRAS CoV S protein, i.e., binding to target cells including VERO E6, NIH3T3. This activity can be determined by the assays described in the examples presented below.

A polypeptide of the invention can be obtained as a synthetic polypeptide or a recombinant polypeptide. To prepare a recombinant polypeptide, a nucleic acid encoding it can be linked to another nucleic acid encoding a fusion partner, e.g., Glutathione-S-Transferase (GST), 6x-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention.

A polypeptide of the invention can be used to generate antibodies in animals (for production of antibodies) or humans (for treatment of diseases). Methods of making monoclonal and polyclonal antibodies and fragments thereof in animals are known in the art. See, for example, Harlow and Lane, (1988) Antibodies: A Laboratory Manual, Cold Spring Harbor Laboratory, New York. The term “antibody” includes intact molecules as well as fragments thereof, such as Fab, $F(ab')_2$, Fv, scFv (single chain antibody), and dAb (domain antibody; Ward, et. al. (1989) Nature, 341, 544). These antibodies can be used for detecting the S polypeptide, e.g., in determining whether a test sample from a subject contains coronavirus or in identifying a compound that binds to the polypeptide. As these antibodies interfere with the cell binding and entry of the coronavirus, they are also useful for treating a coronavirus infection.

In general, to produce antibodies against a polypeptide, the polypeptide is coupled to a carrier protein, such as KLH, mixed with an adjuvant, and injected into a host animal. Antibodies produced in the animal can then be purified by peptide affinity chromatography. Commonly employed host animals include rabbits, mice, guinea pigs, and rats. Various adjuvants that can be used to increase the immunological response depend on the host species and include Freund’s adjuvant (complete and incomplete), mineral gels such as aluminum hydroxide, CpG, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum.*

Polyclonal antibodies, heterogeneous populations of antibody molecules, are present in the sera of the immunized subjects. Monoclonal antibodies, homogeneous populations of antibodies to a polypeptide of this invention, can be prepared using standard hybridoma technology (see, for example, Kohler et al. (1975) Nature 256, 495; Kohler et al. (1976) Eur. J. Immunol. 6, 511; Kohler et al. (1976) Eur J Immunol 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) Nature 256, 495 and U.S. Pat. No. 4,376,110; the human B-cell hybridoma technique (Kosbor et al. (1983) Immunol Today 4, 72; Cole et al. (1983) Proc. Natl. Acad. Sci. USA 80, 2026, and the EBV-hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies of the invention may be cultivated in vitro or in vivo. The ability to produce high titers of monoclonal antibodies in vivo makes it a particularly useful method of production.

In addition, techniques developed for the production of “chimeric antibodies” can be used. See, e.g., Morrison et al. (1984) Proc. Natl. Acad. Sci. USA 81, 6851; Neuberger et al. (1984) Nature 312, 604; and Takeda et al. (1984) Nature 314:452. A chimeric antibody is a molecule in which different portions are derived from different animal species, such as those having a variable region derived from a murine monoclonal antibody and a human immunoglobulin constant region. Alternatively, techniques described for the production of single chain antibodies (U.S. Pat. Nos. 4,946,778 and 4,704,692) can be adapted to produce a phage library of single chain Fv antibodies. Single chain antibodies are formed by linking the heavy and light chain fragments of the Fv region via an amino acid bridge. Moreover, antibody fragments can be generated by known techniques. For example, such fragments include, but are not limited to, $F(ab')_2$ fragments that can be produced by pepsin digestion of an antibody molecule, and Fab fragments that can be generated by reducing the disulfide bridges of $F(ab')_2$ fragments. Antibodies can also be humanized by methods known in the art. For example, monoclonal antibodies with a desired binding specificity can be commercially humanized (Scotgene, Scotland; and Oxford Molecular, Palo Alto, Calif.). Fully human antibodies, such as those expressed in transgenic animals are also features of the invention (see, e.g., Green et al. (1994) Nature Genetics 7, 13; and U.S. Pat. Nos. 5,545,806 and 5,569,825).

A polypeptide of the invention can also be used to prepare an immunogenic composition (e.g., a vaccine) for generating antibodies against coronavirus (e.g., SRAS CoV) in a subject susceptible to the coronavirus. Such compositions can be prepared, e.g., according to the method described in the examples below, or by any other equivalent methods known in the art. The composition contains an effective amount of a polypeptide of the invention, and a pharmaceutically acceptable carrier such as phosphate buffered saline or a bicarbonate solution. The carrier is selected on the basis of the mode and route of administration, and standard pharmaceutical practice. Suitable pharmaceutical carriers and diluents, as well as pharmaceutical necessities for their use, are described in Remington’s Pharmaceutical Sciences. An adjuvant, e.g., a cholera toxin, *Escherichia coli* heat-labile enterotoxin (LT), liposome, immune-stimulating complex (ISCOM), or immunostimulatory sequences oligodeoxynucleotides (ISS-ODN), can also be included in a composition of the invention, if necessary. The S protein, fragments or analogs thereof or peptides may be components of a multivalent composition of vaccine against respiratory diseases. This multivalent composition contains at least one immunogenic fragment of S protein described above, along with at least one protective antigen isolated from influenza virus, para-influenza virus 3, *Strentococcus pneumoniae, Branhamella* (*Moroxella*) *gatarhalis, Staphylococcus aureus*, or respiratory syncytial virus, in the presence or absence of adjuvant.

Methods for preparing vaccines are generally well known in the art, as exemplified by U.S. Pat. Nos. 4,601,903; 4,599,231; 4,599,230; and 4,596,792. Vaccines may be prepared as injectables, as liquid solutions or emulsions. The S protein, fragments or analogs thereof or peptides corresponding to portions of S protein may be mixed with physiologically acceptable and excipients compatible. Excipients may include, water, saline, dextrose, glycerol, ethanol, and combinations thereof. The vaccine may further contain minor amounts of auxiliary substances such as wetting or emulsifying agents, pH buffering agents, or adjuvants to enhance the effectiveness of the vaccines. Methods of achieving adjuvant effect for the vaccine includes use of agents, such as aluminum hydroxide or phosphate (alum), commonly used as 0.05 to 0.1 percent solutions in phosphate buffered saline. Vaccines may be administered parenterally, by injection subcutaneously or intramuscularly. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose, magnesium carbonate and the like. These compositions take the form of solutions, suspensions, tablets, pills, capsules, sustained release formulations or powders and contain 10-95% of the S protein, fragment analogs, or peptides.

The vaccines are administered in a manner compatible with the dosage formulation, and in an amount that is therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the polypeptide of this invention. Suitable regimes for initial administration and booster doses are also variable, but may include an initial administration followed by subsequent administrations. The dosage of the vaccine may also depend on the route of administration and varies according to the size of the host.

Use of polypeptide in vivo may first require chemical modification of the peptides since they may not have a sufficiently long half-life. A chemically modified peptide or a peptide analog includes any functional chemical equivalent of the peptide characterized by its increased stability and/or efficacy in vivo or in vitro in respect of the practice of the invention. The term peptide analog also refers to any amino acid derivative of a peptide as described herein. A peptide analog can be produced by procedures that include, but are not limited to, modifications to side chains, incorporation of unnatural amino acids and/or their derivatives during peptide synthesis and the use of cross-linkers and other methods that impose conformational constraint on the peptides or their analogs. Examples of side chain modifications include modification of amino groups, such as by reductive alkylation by reaction with an aldehyde followed by reduction with $NaBH_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with $NABH_4$. The guanidino group of arginine residues may be modified by the formation of heterocyclic condensation products with reagents such as 2,3-butanedione, phenylglyoxal and glyoxal. The carboxyl group may be modified by carbodiimide activation via o-acylisourea formation followed by subsequent derivatization, for example, to a corresponding amide. Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH. Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

A nucleic acid molecule of this invention may also be used directly for immunization by administration of the nucleic acid directly to a subject via a live vector, such as *Salmonella*, BCG, adenovirus, poxvirus or vaccinia. Immunization methods based on nucleic acids are well known in the art.

A subject susceptible to coronavirus infection can be identified and administered a polypeptide-containing composition of the invention. The dose of the composition depends, for example, on the particular polypeptide, whether an adjuvant is co-administered with the polypeptide, the type of adjuvant co-administered, the mode and frequency of administration, as can be determined by one skilled in the art. Administration is repeated as necessary, as can be determined by one skilled in the art. For example, a priming dose can be followed by three booster doses at weekly intervals. A booster shot can be given at 4 to 8 weeks after the first immunization, and a second booster can be given at 8 to 12 weeks, using the same formulation. Sera or T-cells can be taken from the subject for testing the immune response elicited by the composition against the coronavirus S protein or infection. Methods of assaying antibodies or cytotoxic T cells against a protein or infection are well known in the art. Additional boosters can be given as needed. By varying the amount of polypeptide, the dose of the composition, and frequency of administration, the immunization protocol can be optimized for eliciting a maximal immune response. Before a large scale administering, efficacy testing is desirable. In an efficacy testing, a non-human subject can be administered via an oral or parenteral route with a composition of the invention. After the initial administration or after optional booster administration, both the test subject and the control subject (receiving mock administration) are challenged with an $LD_{95}$ dose of a coronavirus. End points other than lethality can also be used. Efficacy is determined if subjects receiving the composition dies at a rate lower than control subjects. The difference in death rates should be statistically significant.

The above-described S protein and its fragment can be used as a carrier and linked to other antigens of interest to generate antibodies against the antigens. The S protein or its fragment can be generally utilized to prepare chimeric molecules and conjugate compositions against pathogenic bacteria, including encapsulated bacteria. For example, the glycoconjugates of the present inventions may be applied to immunize a subject to generate antibodies against the bacteria and confer protection against infection with any bacteria having polysaccharide antigens, e.g., *Haemophilus influenzae, Streptococcus pneumoniae, Escherichia coli, Neisseria meningitidis, Salmonella typhi, Streptococcus mutans, Cryptococcus neoformans, Klebsiella, Staphylococcus aureus*, and *Pseudomonas aeruginosa*. In addition, as a carrier, the S protein or fragment may be used to induce immunity toward abnormal polysaccharides of tumor cells, thereby to produce anti-tumor antibodies for chemotherapy or diagnosis.

Also within the scope of this invention is a diagnosing method using the above-described polypeptides or antibodies. Presence of the polypeptides or antibodies in a subject indicates that the subject is infected with a coronavirus. To detect the antibodies or polypeptides, one can obtain a test sample from a subject and detect the presence or absence of the antibodies or polypeptides using standard techniques, including ELISAs, immunoprecipitations, immunofluorescence, EIA, RIA, and Western blotting analysis.

The nucleic acid of this invention is useful as a hybridization probe for identifying coronavirus, e.g., SARS CoV, in a sample. The sample can be a clinical sample, including exudates, body fluids (e.g., serum, amniotic fluid, middle ear effusion, sputum, bronchoalveolar lavage fluid) and tissues. A variety of hybridization conditions may be employed to achieve varying degrees of selectivity of the probe toward the target sequences. A high degree of selectivity requires stringent conditions, such as that described in the Summary section A hybridization reaction can be performed both in a solution or on a solid phrase. In a solid phase, a test sequence from a sample is affixed to a selected matrix or surface. The fixed nucleic acid is then subjected to specific hybridization with selected probes comprising the nucleic acid of the present invention under desired conditions. The selected conditions will depend on the particular circumstances based on the particular criteria required depending on, for example, on the G+C contents, type of target nucleic acid, source of nucleic acid, size of hybridization probe etc. Following washing of the hybridization surface to remove non-specifically bound probe molecules, specific hybridization is detected or quantified, by means of the label. The selected probe should be at least 18 bp and may be in the range of 30 bp to 90 bp long.

In addition, A small interference RNA (SiRNA) corresponding to the nucleotide sequences of the present invention comprising the sequence of the S protein receptor binding domains such as RBD1 and RBD2, can be useful to block SARS CoV replication in vivo.

A polypeptide of this invention can also be used in a screening method of identifying a compound for treating an infection with a coronavirus, e.g., SARS CoV. The method includes (1) contacting a polypeptide of this invention with a suitable cell, to which the coronavirus binds to; and (2) determining a binding level between the polypeptide and the cell the presence or absence of a test compound. The binding level in the presence of the test compound, if lower than that in the absence of the test compound, indicates that the test compound can be used to treat an infection with the coronavirus. Examples of the cell include VERO E6 cells, NIH3T3 cells, HeLa cells, BHK-21 cells, and COS-7 cells. One can also use other cells that are capable of binding to a coronavirus.

The above-described polypeptides and antibodies can be used for treating an infection with a coronavirus, e.g., SARS. The invention therefore features a method of treating SARS, e.g., by administering to a subject in need thereof an effective amount of a polypeptide, an antibody, or a compound of the invention. Subjects to be treated can be identified as having, or being at risk for acquiring, a condition characterized by SARS. This method can be performed alone or in conjunction with other drugs or therapy.

Thus, also within the scope of this invention is a pharmaceutical composition that contains a pharmaceutically acceptable carrier and an effective amount of a polypeptide, an antibody, or a compound of the invention. The pharmaceutical composition can be used to treat coronavirus infection, such as SARS. The pharmaceutically acceptable carrier includes a solvent, a dispersion medium, a coating, an antibacterial and antifungal agent, and an isotonic and absorption delaying agent.

In one in vivo approach, a composition of this invention (e.g., a composition containing a polypeptide, an antibody, or a compound of the invention) is administered to a subject. Generally, the antibody or the compound is suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the subject's illness; the subject's size, weight, surface area, age, and sex; other drugs being administered; and the judgment of the attending physician. Suitable dosages are in the range of 0.01-100.0 mg/kg. Wide variations in the needed dosage are to be expected in view of the variety of compositions available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the composition in a suitable delivery vehicle (e.g., polymeric microparticles or implantable devices) may increase the efficiency of delivery, particularly for oral delivery.

A pharmaceutical composition of the invention can be formulated into dosage forms for different administration routes utilizing conventional methods. For example, it can be formulated in a capsule, a gel seal, or a tablet for oral administration. Capsules can contain any standard pharmaceutically acceptable materials such as gelatin or cellulose. Tablets can be formulated in accordance with conventional procedures by compressing mixtures of the composition with a solid carrier and a lubricant. Examples of solid carriers include starch and sugar bentonite. The composition can also be administered in a form of a hard shell tablet or a capsule containing a binder, e.g., lactose or mannitol, conventional filler, and a tableting agent. The pharmaceutical composition can be administered via the parenteral route. Examples of parenteral dosage forms include aqueous solutions, isotonic saline or 5% glucose of the active agent, or other well-known pharmaceutically acceptable excipient. Cyclodextrins, or other solubilizing agents well known to those familiar with the art, can be utilized as pharmaceutical excipients for delivery of the therapeutic agent.

The efficacy of a composition of this invention can be evaluated both in vitro and in vivo. Briefly, the composition can be tested for its ability to inhibit the binding between a coronavirus and its target cell in vitro. For in vivo studies, the composition can be injected into an animal (e.g., a mouse model) and its therapeutic effects are then accessed. Based on the results, an appropriate dosage range and administration route can be determined.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

In this example, the gene encoding S protein of SARS CoV was cloned. A SARS CoV, designated as "SARS-CoV TW1," was isolated from a SARS patient in Taiwan. Seven pairs of PCR primers were designed based on the sequence of the Urbani strain (SEQ ID NO: 1) or the SARS CoV TOR2 strain. The positions of the primers' 5' ends within the Urbani genome were summarized below:

| | 5' primer | 3' primer |
|---|---|---|
| Pair 1 | 21,492 | 22,000 |
| Pair 2 | 22,000 | 22,600 |
| Pair 3 | 22,600 | 23,100 |
| Pair 4 | 23,075 | 23,780 |
| Pair 5 | 23,765 | 24,320 |
| Pair 6 | 24,300 | 24,875 |
| Pair 7 | 24,850 | 25,244 |

Seven products were generated by PCR reactions respectively and ligated together to form a sequence that encoded the S protein. The sequence was then subcloned into pUC19 to produce pUC19/S and used to transform *E. coli* HB101. Plasmid DNA was prepared from two *E. coli* HB101 colonies and sequenced on an ABI 370A DNA sequencer. Subsequent sequence analysis revealed that the sequence differed from that of the TOR2 strain by 3 base pairs and that it is about 30.1% identical to that of human coronavirus 229E.

SARS CoV M and E proteins (GenBank Accession Nos. AAP 13443 and 13444) were also cloned and expressed. The E-M fusion protein corresponds to residues 8751 to 9057 of the first open reading frame of SEQ ID NO: 1. Construction of DNA plasmids containing genes for E and M proteins was performed by standard molecular biology methods (Sambrook et al (1989) Molecular cloning: a laboratory manual. 2$^{nd}$ ed. Cold Spring Harbor Laboratory. Cold Spring Harbor, N.Y.). The constructs utilized a pUC-based expression vector, which was shown to result in optimal expression of reporter genes. Each vector employed the human cytomegalovirus promoter, enhancer, intron A, and the bovine growth hormone termination and polyasenylation sequences. The tissue plasminogen activator signal sequence was use to enhance the level of expression. The M and E proteins were further expressed in host cells to generated virus like particles.

EXAMPLE 2

It is known that, in SARS CoV, the S native protein is expressed in small quantities. To obtain a large amount of the S protein, there is a need to either express it in a heterologous system, such as *E. coli*, or to modify SARS CoV to increase the native S protein expression.

The above-described PUC19/S was transformed into *E. coli.* to express the S protein. It was found that the full-length recombinant S (rS) protein was not expressed in *E. coli*. Vectors encoding different S protein fragments fused to Myc-His tag were then constructed and transformed in *E. coli*. The fragments include the N-terminal amino acids 80-228 of the S protein (receptor binding domain 1; RBD1); the middle region encompassing amino acids 284-735 of the S protein (receptor binding domain 2; RBD2), the transmembrane domain (TM), and fusions of them.

To examine the expressed protein, antisera against various SARS CoV proteins were generated The following SARS CoV polypeptides were synthesized by standard techniques:

```
RBD1-specific  KSGNFKHLREFVFKNKDGFLYVYKGQPIDV
peptide        (SEQ ID NO:29)

RBD2-specific  GNYNYKYRYLRHGKLRPFERDISNVPFSPDGKPC
peptide        (SEQ ID NO:24)

TM-specific    DSFKEELDRY FKNHTSPDVD LGDISGINAS VV
peptide        (SEQ ID NO:30)

E-specific     ALRLCAYCCN IVNVSLVKPT VYVYSRVKNL
peptide        NSSEG (SEQ ID NO:31)

M-specific     MADNGTITVE ELKQLLEQWN LVICFLFLWA IML
peptide        (SEQ ID NO:32)
```

More specifically, 200 μg of each peptide was mixed with the completed Fruend's adjuvant and injected at day 0 and injected into rabbits by standard techniques At day 14 and 56, the rabbits were boosted with half of the amount of the peptide in the incomplete Fruend's adjuvant At day 78, the rabbits were bleed, and the blood were tested for antiserum titer by ELISA The results are shown in Table 1

TABLE 1

Rabbit immunogenicity of SARS CoV peptides
Reactivity of Anti-peptide sera to target peptide

| Peptides | Pre-Immune | Post-booster | Final Bleed |
|---|---|---|---|
| RBD1-specific | 0 | 5120 | 10240 |
| RBD2-specific | 0 | 10240 | 41440 |
| TM-specific | 0 | 5120 | 10240 |
| E-specific | 0 | 1280 | 5120 |
| M-specific | 0 | 5120 | 10240 |

To generate a vector encoding RBD1, the following two primers were used for PCR: 5' primer: GGATCCGCCACC ATG catacgtttg g (SEQ ID NO:33); and 3' primer: aa ttttagagcc GAATTC (SEQ ID NO:34) The two primers contained EcoRI and BamHI sites to facilitate subsequent cloning of PCR products A ~500 base pair (bp) fragment was obtained and subcloned into pcDNA-A4 to generate pcDNA-A4-D1 plasmid, which encoded a fusion protein of Myc-His-RBD This plasmid was transformed into *E coli* HB101 to express recombinant RBD1 (rRBD1) It was found that, upon induction, the transformed clones expressed a 20 kDa protein This protein was expressed at high levels in inclusion bodies and was recognized by anti-RBD-1 antisera and anti-His tag antibody on Western blot analysis It was also found that protein was highly immunogenic, but not able to elicit protective antibodies against live virus challenge A vector encoding RBD2 was also generated More specifically, PCR was conducted using the following two primers 5' primer: GGATCCGCCACCATG gagattgaca (SEQ ID NO:35) and 3' primer: aatatgg GCGGCCGC (SEQ ID NO:36) to generate a 14 kb fragment After being digested by BamH1-Not1, the resulting fragment was also subcloned into pcDNA-A4 The resultant vector was used to express RBD2 in the same manner described above It was found that a 50-kDa protein was expressed at high levels in both soluble form and in inclusion bodies Western blot analysis revealed that this protein was recognized by the S-specific antisera This rRBD2 fragment was highly immunogenic too and elicited even stronger neutralizing antibodies that could block SARS CoV binding to Vero cell (see Example 9 below)

EDTA. The protein-containing factions were collected and the purity was analyzed by SDS-PAGE.

It was estimated that about 10 mg of rRBD2 was recovered from 1 L of *E. coli* bacterial culture. The identity of rRBD2 was confirmed by both immunoblotting and protein sequencing. The N-terminal sequence of this polypeptide was found to be Met-Ala-Glu-Leu-Lys-Cys, which corresponds to residues 284 to 288 of the sequence of S protein.

EXAMPLE 3

In this example, additional fragments of the SARS coronavirus S protein were expressed in baculovirus and SF21 insect cell.

Nucleic acids encoding 1-333, 334-666, and 667-999 amino acid of the S protein (spike1, spike2, and spike3; S1, S2, and S3, respectively) were obtained by PCR with primer sets listed below, respectively, in the manner similar to that described in Example 1

| Amplified fragment | Primer name | Sequence (5' to 3') | Sense |
|---|---|---|---|
| Spike1 | S1F | AGGGATCCATGTTTATTTTCTTATTATTTCTTACTC | S |
| (1-333 aa) | S1R | CCTGGATCCTTTAGTAGCATTAAAAACCTCTCCA | AS |
| Spike2 | S2F | AGGGGATCCTTCCCTTCTGTCTATGCATGGGAGA | S |
| (334-666 aa) | S2R | CCTGGATCCTAATAAAGAAACTGTATGGTAACTA | AS |
| Spike3 | S3F | AGGGGATCCCGTAGTACTAGCCAAAAATCTATTG | S |
| (667-999 aa) | S3R | CCTGGATCCTTCAGCAGCCCTGATTAGTTGTTGT | AS |
| RBD1 | RBD1F | CATACGTTTGGCAACCCTGTC | S |
| (74-253 aa) | RBD1R | AACATTACAAATTTTAGAGCC | AS |
| RBD2 | RBD2F | GAGATTGACAAAGGAATTTAC | S |
| (294-73 9 aa) | RBD2R | CTAATTTGCTTCTCCAATATGG | AS |
| RBD3 | RBD3F | ATGGCTAAAACCTCCGTAGAT | S |
| (713-1113 aa) | RBD3R | AATTGTGATGTCGTTATTGGC | AS |
| TM | TM1F | ACTTCAAAAATCATACATCA | S |
| (1130-1255 aa) | TM1R | GGTGTCAAATTACATTACACATAA | AS |

SEQ ID NOs 37-50, respectively

The above-described recombinant proteins were isolated from *E. coli*. More specifically, *E. coli* pellet from a 250 mL culture was resuspended in 40 mL of 50 mM Tris, pH 8.0, and disrupted by sonication (3×10 minutes, 70% duty circle). The resultant mixture was centrifuged at 20,000×g. The pellet was re-extracted with 40 mL of 50 mM Tris, 0.5% Triton X-100, 10 mM EDTA, pH 8.0. The suspension was then sonicated for 10 minutes at 70% duty circle and centrifuged at 300×g for 5 minutes. The resulting supernatant was centrifuged again at 20,000×g for 30 minutes. The pellet was resuspended in 50 mM Tris, 0.5% Triton X-100, 10 mM EDTA, pH 8.0 and mixed with PBS/8 M urea to a final urea concentration of 6 M urea. The mixture was then dialyzed against PBS to remove urea and centrifuged at 300×g for 10 minutes. The supernatant was saved and stored at 4° C.

Ni-affinity chromatography was used to isolate rRBD1 and rRBD2 fusion proteins from inclusion body. The just described supernatant was loaded onto a Ni affinity column (2 mL) equilibrated with PBS containing 1% Triton X-100. The run-through of the column was discarded. After washing the column with 20 mL of PBS, the affinity column was eluted with 50 mM Tris-HCl buffer, pH 8.0, containing 5 mM The PCR products were inserted into the pCR2.1 vector by TA cloning. The coding sequences were than released by BamHI digestions and ligated to BamHI-cutted pSecTagb/hIgG1.Fc vector, thereby in-frame fusing the S protein-encoding sequence to that encoding the human IgG1 Fc, The resultant vectors encodes fusion proteins spike 1-Fc, spike2-Fc, and spike3-Fc. To generate corresponding baculovirus transfer vectors, the three fusion genes were released by NheI/XhoI digestion and ligated to XbaI/XhoI-cutted pBacPAK9 vectors.

The just-described pBacPAK9 vectors were co-transfected into Sf21 cells with Bsu36 I-digested BacPAK6 viral DNA by Bacfectin (Clontech 6144-1). Each resulting viral plaque was picked by performing plaque assays on the co-transfection supernatant. The recombinant viruses were confirmed by PCR. Sf21 cells were then infected with virus at a small scale to characterize gene expression and to determine the optimum harvest time and infection ratio by standard methods. Recombinant viruses were amplified to high virus titer to obtain working stocks for large-scale infection.

To purify recombinant proteins, Sf21 cells were cultured in spinner flask at a starting concentration of $2\times10^5$/ml in the first 3-5 days. After reaching 1-2×$10^6$ cells/ml, the cells were infected with the above-described recombinant baculoviruses at M.O.I. of 5-10 and cultured for 4-5 days. The supernatants were then collected and cell debris was removed by centrifugation. The supernatant was loaded onto protein A Sepharose® 4 Fast Flow beads (Amersham Biosciences 17-0974). Finally, the bound Fc-fusion protein was eluted with a 0.1 M glycine buffer (pH 3.0), followed by dialysis against PBS. The purity and the concentration of purified proteins were assessed by a standard silver staining method.

Five milligrams of S1-Fc fusion protein crude extract prepared in the manner described above were dissolved in 5 mL of phosphate buffer saline (PBS) containing 1% Triton X-100. The solution was then loaded onto a Protein A-Sepharose 4B column (2 mL) equilibrated with PBS containing 1% Triton X-100. The run-through of the column was discarded. The column was washed with 20 mL of PBS and the S1-Fc fusion protein was eluted with 50 mM Gly-HCl buffer, pH 3.0. Elution was monitored by absorbance at 280 nm. Protein-containing fractions (2 mL/fraction) were collected and pooled. The purity of the protein was assessed by SDS-PAGE.

Certain plasmids described above was deposited with the American Type Culture Collection (ATCC) located at 10801 University Boulevard, Manassas, Va. 20110-2209 U.S.A. pursuant to the Budapest Treaty and prior to the filing of this application. Samples of the deposited plasmids will become available to the public upon grant of a patent based upon this United States patent application.

EXAMPLE 4

The above-described recombinant RBD1, RBD2, S1-FC, and S2-Fc were used to produce of S-specific antisera. The purified recombinant proteins were emulsified in the Freund's complete adjuvant (Difco) and injected intramuscularly (IM) into New Zealand White rabbits (Maple Lane) or guinea pigs (Charles River) at a dose of 10 to 100 μg/injection. The animals were boosted on day 28 with another half of dose of the corresponding S fragment emulsified in Freund's incomplete adjuvant. On day 42, a blood sample was taken from each animal via the marginal ear vein for titer determination by standard methods. Animals that generated specific antibodies were bled to obtain more antisera.

To examine the immunogenicity of the RBD1 or 2 fusion protein, guinea pigs or mice were immunized with RBD1 or 2 of various amounts. The doses between 10 to 100 μg/injection RBD1 induced high IgG titers in guinea pigs when administered in the presence of either Freund's adjuvant or $AlPO_4$. In the mice, RBD1 or 2 appeared to be immunogenic at a dose as low as 5 μg/injection in either Freund's adjuvant.

A ferret model was used to examine the protective ability of anti-RBD1 or 2 sera against a SARS CoV infection. It was found that ferrate passively immunized with guinea pig anti-RBD2 antisera, but not anti-RBD1 sera, were significantly protected than controls injected with pre-immune sera.

The above-described S1-Fc or S2-Fc fusion protein was used to purify S protein-specific polyclonal antibodies by affinity chromatography. The recombinant S1-Fc or S2-Fc fusion protein was conjugated to cyanogen bromide-activated Sepharose to form an affinity column. The affinity column was then used to purify antibodies from a rabbit hyperimmune anti-inactivated SARS CoV antiserum. The affinity purified-antibodies were shown by immunoblotting to react with a 200-kDa component present in the lysates of SARS Cov isolates. Similarly, antisera raised against the recombinant fusion protein or the purified RBD1, RBD2, S1 and S2 can also be purified in the same manner.

EXAMPLE 5

Purified recombinant RBD2 were conjugated with *S. pneumococcal* oligosaccharides 14 (14F) by periodate oxidation in the manner described in U.S. Pat. No. 4,356,170. *S. pneumococcal* oligosaccharides 14 was prepared by controlled acid hydrolysis. The mean molecular size of the 14F molecules used for conjugation was determined as approximately 20,000 Daltons. The conjugation was carried out with or without a linker molecule. A 14/RBD2 molar ratio of approximately 7 was used to provide an excess of 14F hapten.

To prepare 14-BSA conjugates, 0.5 mL of periodate-oxidized 14 (25 mg in 1 mL of 0.1 M sodium phosphate buffer, pH 6.0), prepared from native 14F treated with aqueous periodic acid (Carlone et al, 1986 J. Clin. Microbiol. 24:330-331.), was added to bovine serum albumin (BSA) (1.32 mg; 0.02 μmol) in 0.5 mL of 0.2 M sodium phosphate buffer, pH 8.0, followed by the addition of sodium cyanoborohydride (14 μg; 0.22 μmol; 10 eqv. to BSA). After incubation at 37° C. for 5 days, the reaction mixture was dialyzed against 4 L of 0.1 M phosphate buffer, pH 7.5. The resulting solution was applied onto an analytical Superose 12 column (15×0.300 mm, Pharmacia) equilibrated with 0.2 M sodium phosphate buffer, pH 7.2, and eluted with the same buffer. Fractions were monitored for absorbance at 230 nm. The first major protein peak was pooled and concentrated in a Centriprep 30 to 2.2 mL. The amount of protein was found, by the Bio Rad protein assay, to be 300 ug/mL. The presence of 14 oligosaccharides in the protein conjugate fraction was confirmed by the Orcinol test.

The above-described RBD2-14 *S. pneumococcal* polysaccharide conjugate was then used to produce anti-14 *S. pneumococcal* polysaccharide antisera in animals. Rabbits were immunized intramuscularly with 14-RBD2 conjugates (5 to 50 μg 14 equivalent) mixed with 3 mg $AlPO_4$ per mL, followed by two booster doses (half amount of the same immunogen) at 2-week intervals. Antisera were collected every 2 weeks after the first injection, heat-inactivated at 56° C. for 30 minutes and stored at −20° C. It was found that the immunization elicited both primary and secondary immune responses against PRP-IgG and S protein. Rabbit anti-RBD2-14F antisera also strongly reacted with both native S and rS as determined by immunoblot analysis. These results indicate that RBD2 can be used as a carrier protein in a conjugate vaccine. Since RBD2-14 *S. pneumococcal* polysaccharide conjugate elicited antibodies against both 14F and S, it can be used to d thus should enhance the level of protection against *S. pneumococcal*-related diseases, especially in infants.

EXAMPLE 6

To map the linear B-cell epitopes of the SARS S protein, overlapping synthetic peptides covering the entire S protein were synthesized. These peptides were listed in Table 2 below.

TABLE 2

Synthetic SARS CoV S peptides

| Peptide ID No | MW | Sequence | SEQ ID NO: |
|---|---|---|---|
| RED1-related fragments | | | |
| 1 | 1,6812 | VIPFKDGIYFAATEK | 51 |
| 2 | 1,6520 | DGIYFAATEKSNVVR | 52 |
| 3 | 1,6029 | AATEKSNVVRGWVFG | 53 |
| 4 | 1,6499 | SNVVRGWVFGSTMNN | 54 |
| 5 | 1,6238 | GWVFGSTMNNKSQSV | 55 |
| 6 | 1,6449 | STMNNKSQSVIIINN | 56 |
| 7 | 1,5978 | KSQSVIIINNSTNVV | 57 |
| 8 | 1,6261 | IIINNSTNVVIRACN | 58 |
| 9 | 1,6661 | STNVVIRACNFELCD | 59 |
| 10 | 1,7423 | IRACNFELCDNPFFA | 60 |
| 11 | 1,7272 | FELCDNPFFAVSKPM | 61 |
| 12 | 1,6439 | NPFFAVSKPMGTQTH | 62 |
| 13 | 1,6750 | VSKPMGTQTHTMIFD | 63 |
| 14 | 1,6820 | GTQTHTMIFDNAFNC | 64 |
| 15 | 1,8113 | TMIFDNAFNCTFEYI | 65 |
| 16 | 1,7111 | NAFNCTFEYISDAFS | 66 |
| 17 | 1,7050 | TFEYISDAFSLDVSE | 67 |
| 18 | 1,5849 | SDAFSLDVSEKSGNF | 68 |
| 19 | 1,7412 | LDVSEKSGNFKHLRE | 69 |
| 20 | 1,8334 | KSGNFKHLREFVFKN | 70 |
| 21 | 1,8605 | KHLREFVFKNKDGFL | 71 |
| 22 | 1,8074 | FVFKNKDGFLYVYKG | 72 |
| 23 | 1,7882 | KDGFLYVYKGYQPID | 73 |
| 24 | 1,8101 | YVYKGYQPIDVVRDL | 74 |
| 25 | 1,7019 | YQPIDVVRDLPSGFN | 75 |
| 26 | 1,6381 | VVRDLPSGFNTLKPI | 76 |
| 27 | 1,6543 | PSGFNTLKPIFKLPL | 77 |
| RBD2-related fragments | | | |
| 28 | 1,6362 | AELKCSVKSFEIDKG | 78 |
| 29 | 1,6840 | SVKSFEIDKGIYQTS | 79 |
| 30 | 1,7510 | EIDKGIYQTSNFRVV | 80 |
| 31 | 1,6638 | IYQTSNFRVVPSGDV | 81 |
| 32 | 1,6849 | NFRVVPSGDVVRFPN | 82 |
| 33 | 1,6140 | PSGDVVRFPNITNLC | 83 |
| 34 | 1,6881 | VRFPNITNLCPFGEV | 84 |
| 35 | 1,6361 | ITNLCPFGEVFNATK | 85 |

TABLE 2-continued

Synthetic SARS CoV S peptides

| Peptide ID No | MW | Sequence | SEQ ID NO: |
|---|---|---|---|
| 36 | 1,6850 | PFGEVFNATKFPSVY | 86 |
| 37 | 1,8262 | FNATKFPSVYAWERK | 87 |
| 38 | 1,8103 | FPSVYAWERKKISNC | 88 |
| 39 | 1,7522 | AWERKKISNCVADYS | 89 |
| 40 | 1,6581 | KISNCVADYSVLYNS | 90 |
| 41 | 1,6960 | VADYSVLYNSTFFST | 91 |
| 42 | 1,7593 | VLYNSTFFSTFKCYG | 92 |
| 43 | 1,6692 | TFFSTFKCYGVSATK | 93 |
| 44 | 1,6443 | FKCYGVSATKLNDLC | 94 |
| 45 | 1,6561 | VSATKLNDLCFSNVY | 95 |
| 46 | 1,6891 | LNDLCFSNVYADSFV | 96 |
| 47 | 1,6449 | FSNVYADSFVVKGDD | 97 |
| 48 | 1,6018 | ADSFVVKGDDVRQIA | 98 |
| 49 | 1,5226 | VKGDDVRQIAPGQTG | 99 |
| 50 | 1,5697 | VRQIAPGQTGVIADY | 100 |
| 51 | 1,6179 | PGQTGVIADYNYKLP | 101 |
| 52 | 1,7432 | VIADYNYKLPDDFMG | 102 |
| 53 | 1,7543 | NYKLPDDFMGCVLAW | 103 |
| 54 | 1,7372 | DDFMGCVLAWNTRNI | 104 |
| 55 | 1,6470 | CVLAWNTRNIDATST | 105 |
| 56 | 1,6859 | NTRNIDATSTGNYNY | 106 |
| 57 | 1,8112 | DATSTGNYNYKYRYL | 107 |
| 58 | 1,9276 | GNYNYKYRYLRHGKL | 108 |
| 59 | 2,0017 | KYRYLRHGKLRPFER | 109 |
| 60 | 1,8063 | RHGKLRPFERDISNV | 110 |
| 61 | 1,7580 | RPFERDISNVPFSPD | 111 |
| 62 | 1,5589 | DISNVPFSPDGKPCT | 112 |
| 63 | 1,5229 | PFSPDGKPCTPPALN | 113 |
| 64 | 1,6422 | GKPCTPPALNCYWPL | 114 |
| 65 | 1,7522 | PPALNCYWPLNDYGF | 115 |
| 66 | 1,7832 | CYWPLNDYGFYTTTG | 116 |
| 67 | 1,6789 | NDYGFYTTTGIGYQP | 117 |
| 68 | 1,6989 | YTTTGIGYQPYRVVV | 118 |
| 69 | 1,7651 | IGYQPYRVVVLSFEL | 119 |
| 70 | 1,6731 | YRVVVLSFELLNAPA | 120 |
| 71 | 1,5140 | LSFELLNAPATVCGP | 121 |
| 72 | 1,4689 | LNAPATVCGPKLSTD | 122 |

TABLE 2-continued

Synthetic SARS CoV S peptides

| Peptide ID No | MW | Sequence | SEQ ID NO: |
|---|---|---|---|
| 73 | 1,5990 | TVCGPKLSTDLIKNQ | 123 |
| 74 | 1,7191 | KLSTDLIKNQCVNFN | 124 |
| 75 | 1,7071 | LIKNQCVNFNFNGLT | 125 |
| 76 | 1,5380 | CVNFNFNGLTGTGVL | 126 |
| 77 | 1,4609 | FNGLTGTGVLTPSSK | 127 |
| 78 | 1,6039 | GTGVLTPSSKRFQPF | 128 |
| 79 | 1,7928 | TPSSKRFQPFQQFGR | 129 |
| 80 | 1,8558 | RFQPFQQFGRDVSDF | 130 |
| 81 | 1,7387 | QQFGRDVSDFTDSVR | 131 |
| 82 | 1,6508 | DVSDFTDSVRDPKTS | 132 |
| 83 | 1,6710 | TDSVRDPKTSEILDI | 133 |
| 84 | 1,6181 | DPKTSEILDISPCAF | 134 |
| 85 | 1,4890 | EILDISPCAFGGVSV | 135 |
| 86 | 1,3748 | SPCAFGGVSVITPGT | 136 |
| 87 | 1,3576 | GGVSVITPGTNASSE | 137 |
| 88 | 1,5038 | ITPGTNASSEVAVLY | 138 |
| 89 | 1,5937 | NASSEVAVLYQDVNC | 139 |
| 90 | 1,6087 | VAVLYQDVNCTDVST | 140 |
| 91 | 1,5707 | QDVNCTDVSTAIHAD | 141 |
| 92 | 1,5217 | TDVSTAIHADQLTPA | 142 |
| 93 | 1,7241 | AIHADQLTPAWRIYS | 143 |
| 94 | 1,7019 | QLTPAWRIYSTGNNV | 144 |
| 95 | 1,7668 | WRIYSTGNNVFQTQA | 145 |
| 96 | 1,5047 | TGNNVFQTQAGCLIG | 146 |
| 97 | 1,5708 | FQTQAGCLIGAEHVD | 147 |
| 98 | 1,5791 | GCLIGAEHVDTSYEC | 148 |
| 99 | 1,6310 | AEHVDTSYECDIPIG | 149 |
| 100 | 1,4951 | TSYECDIPIGAGICA | 150 |
| 101 | 1,4991 | DIPIGAGICASYHTV | 151 |
| 102 | 1,5602 | AGICASYHTVSLLRS | 152 |
| 103 | 1,6760 | SYHTVSLLRSTSQKS | 153 |
| 104 | 1,6360 | SLLRSTSQKSIVAYT | 154 |
| 105 | 1,5389 | TSQKSIVAYTMSLGA | 155 |
| 106 | 1,4810 | IVAYTMSLGADSSIA | 156 |
| 107 | 1,5129 | MSLGADSSIAYSNNT | 157 |
| 108 | 1,5489 | DSSIAYSNNTIAIPT | 158 |
| 109 | 1,6240 | YSNNTIAIPTNFSIS | 159 |

TABLE 2-continued

Synthetic SARS CoV S peptides

| Peptide ID No | MW | Sequence | SEQ ID NO: |
|---|---|---|---|
| 110 | 1,5880 | IAIPTNFSISTTTEV | 160 |
| 111 | 1,6380 | NFSISITTEVMPVSM | 161 |
| 112 | 1,5759 | ITTEVMPVSMAKTSV | 162 |
| 113 | 1,6591 | MPVSMAKTSVDCNMY | 163 |
| 114 | 1,5891 | AKTSVDCNMYICGDS | 164 |
| 115 | 1,6211 | DCNMYICGDSTECAN | 165 |
| TM-related Fragments | | | |
| 116 | 1,8833 | DSFKEELDKYFKNHT | 166 |
| 117 | 1,7901 | ELDKYFKNHTSPDVD | 167 |
| 118 | 1,6270 | FKNHTSPDVDLGDIS | 168 |
| 119 | 1,4418 | SPDVDLGDISGINAS | 169 |
| 120 | 1,4818 | LGDISGINASVVNIQ | 170 |
| 121 | 1,6379 | GINASVVNIQKEIDR | 171 |
| 122 | 1,7219 | VVNIQKEIDRLNEVA | 172 |
| 123 | 1,7671 | KEIDRLNEVAKNLNE | 173 |
| 124 | 1,6671 | LNEVAKNLNESLIDL | 174 |
| 125 | 1,6961 | KNLNESLIDLQELGK | 175 |
| 126 | 1,7941 | SLIDLQELGKYEQYI | 176 |
| 127 | 2,0132 | QELGKYEQYIKWPWY | 177 |
| 128 | 2,0604 | YEQYIKWPWYVWLGF | 178 |
| 129 | 1,8315 | KWPWYVWLGFIAGLI | 179 |
| 130 | 1,5843 | VWLGFIAGLIAIVMV | 180 |
| 131 | 1,5254 | IAGLIAIVMVTILLC | 181 |
| 132 | 1,5834 | AIVMVTILLCCMTSC | 182 |
| 133 | 1,6046 | TILLCCMTSCCSCLK | 183 |
| 134 | 1,4824 | CMTSCCSCLKGACSC | 184 |
| 135 | 1,4354 | CSCLKGACSCGSCCK | 185 |
| 136 | 1,5221 | GACSCGSCCKFDEDD | 186 |
| 137 | 1,6260 | GSCCKFDEDDSEPVL | 187 |
| 138 | 1,6730 | FDEDDSEPVLKGVKL | 188 |
| S3 Fragments | | | |
| S3-1 | | GDSTECANLLLQYGS | 189 |
| S3-2 | | LQYGSFCTQLNRALS | 190 |
| S3-3 | | NRALSGIAAEQDRNT | 191 |
| S3-4 | | QDRNTREVFAQVKQM | 192 |
| S3-5 | | QVKQMYKTPTLKYFG | 193 |
| S3-6 | | LKYFGGFNFSQILPD | 194 |

TABLE 2-continued

| Synthetic SARS CoV S peptides | | | |
|---|---|---|---|
| Peptide ID No | MW | Sequence | SEQ ID NO: |
| S3-7 | | QILPDPLKPTKRSFI | 195 |
| S3-8 | | KRSFIEDLLFNKVTL | 196 |
| S3-9 | | KVTLLADAGFMKQYG | 197 |
| S3-10 | | MKQYGECLGDINARD | 198 |
| S3-11 | | INARDLICAQKFNGL | 199 |
| S3-12 | | KFNGLTVLPPLLTDD | 200 |
| S3-13 | | LLTDDMIAAYTAALV | 201 |
| S3-14 | | TAALVSGTATAGWTF | 202 |
| S3-15 | | AGWTFGAGAALQIPF | 203 |
| S3-16 | | LQIPFAMQMAYRFNG | 204 |
| S3-17 | | YRFNGIGVTQNVLYE | 205 |
| S3-18 | | NVLYENQKQIANQFN | 206 |
| S3-19 | | ANQFNKAISQIQESL | 207 |
| S3-20 | | IQESLTTTSTALGKL | 208 |
| S3-21 | | ALGKLQDVVNQNAQA | 209 |
| S3-22 | | QNAQALNTLVKQLSS | 210 |
| S3-23 | | KQLSSNFGAISSVLN | 211 |
| S3-24 | | SSVLNDILSRLDKVEA | 212 |
| S3-25 | | LDKVEAEVQIDRLITG | 213 |
| S3-26 | | RLITGRLQSLQTYVTQQLIRA | 214 |
| RBD2 | GNYNYKYRYLRHGKLRPFERDISNVPF SPDGKPC (SEQ ID NO:24) | | |
| RBD55 | DPKTSEILDISPCAFGGVSVITPGTNA SSEVAVLYQDVNCTDVSTAIHAD (SEQ ID NO:26) | | |

Note: RBD-55 includes the amino acids covering S84 to S91

The peptides were synthesized by an ABI 433A peptide synthesizer and optimized F-Moc chemistry according to the manufacturer's manual. The synthesized peptides were cleaved from the resin by Trifluoroacetic acid (TFA). They were then purified by reversed-phase high performance liquid chromatography (RP-HPLC) on a Vydac C4 semi-preparative column (1×30 cm) using a 15 to 55% acetonitrile gradient in 0.1% trifluoryl acetic acid (TFA) developed over 40 minutes at a flow rate of 2 mL/min. All synthetic peptides used in subsequent biochemical and immunological studies were >95% pure as determined by analytical HPLC. Amino acid compositions of these peptides were determined on a Waters Pico-Tag system. The results indicated a good agreement with their expected compositions.

ELISA was used to map B-cell epitopes. Microtiter wells (Nunc-Immunoplate, Nunc, Denmark) were coated with 50 µL of a coating buffer (15 mM $Na_2CO_3$, 35 mM $NaHCO_3$, pH 9.6) containing 200 ng of purified recombinant S fragments or 500 ng of individual peptides (listed in Table 3 below) for 16 hours at room temperature. The plates were then blocked in 0.1% (w/v) BSA in phosphate buffer saline (PBS) for 30 minutes at room temperature. Serially diluted antisera were added to the wells and incubated for 1 hour at room temperature. After removal of the antisera, the plates were washed five times with PBS containing 0.1% (w/v) Tween-20 and 0.1% (w/v) BSA. Fab'2 fragments from goat anti-rabbit, -guinea pig, -mouse, or -human IgG antibodies conjugated to horseradish peroxidase (Jackson ImmunoResearch Labs Inc., PA) were diluted (1/8,000) with a washing buffer, and added to the microtiter wells. After incubating for 1 hour at room temperature, the wells were washed five times with the washing buffer and then developed using the substrates tetramethylbenzidine (TMB) and $H_2O_2$ (ADI, Toronto). The reaction was stopped by adding 1N $H_2$ $SO_4$ and the optical density was measured at 450 nm by a Titretek Multiskan II (Flow Labs., Virginia). Two irrelevant peptides were used as negative controls. All assays were performed in triplicate, and the reactive titer of each antiserum was defined as the dilution consistently showing 2-fold increase absorbance value over those obtained from the negative controls. Immunodomiant B-cell epitopes were identified to residues 125-146, 334-348, 409-423, 449-468, 589-603, and 1232-1246. These results indicate that these regions contain the linear B-cell epitope sequences and that they can be used as target antigens in, e.g., diagnostic kits to detect the presence of anti-S and anti-SARS CoV antibodies in samples.

EXAMPLE 7

It is known that SRAS CoV binds to VERO E6 cells. The above-described S protein fragments were tests for their ability to bind to VERO E6 cells. Vero E6 cells (1×10$^4$ cells per mL) were incubated with S1-Fc, S2-Fc, S3-Fc, or human IgG1 at various concentrations in a volume of 1 mL for 2 hours at room temperature. The cells were then washed in PBS containing 0.5% BSA and 0.1% NaN3, incubated with FITC-labeled goat anti-human IgG Fc (Sigma), and analyzed by flow cytometry. It was found that S1-Fc and S2-Fc bound to VERO E6 cells at 1 µg/ml and 0.1 g/ml, respectively. In contrast, S3-fc and human IgG1 did not bind to VERO E6 cell even at 10 µg/ml.

The just-described VERO E6 cell model was used to examine the ability of anti-S1-Fc or anti-S2-Fc serum to inhibit the binding of SARS CoV to VERO E6 cells. VERO E6 cells were cultured on a 24-well plate until they reached approximately 50% confluent. The cells were then incubated with SARS-CoV Tw1 strain (MOI 1:10) and human sera that had a 1/128 virus neutralization titer in the presence or absence of 0.1 to 10 µg/mL corresponding S fusion proteins. After 24-48 hours, the cells were examined under a microscope. The presence of multinucleated giant cells indicated infected cells. The results indicated that human sera blocked the viral infection, and that this blocking activity was repressed by the recombinant S fusion proteins.

EXAMPLE 8

Since S2-Fc fusion protein strongly bound to VERO E6 cell and inhibited human neutralizing antibody activity against SARS CoV, it was of interest to identify the protective epitope(s) of this S2 fragment. Eighty-eight peptides from S2 (shown in Table 2 above) were synthesized based upon the sequence of the SARS CoV TW1 S protein.

Five convalescent sera were obtained from patients infected with SARS CoV and three sera were obtained from guinea pigs immunized with RBD2 in the manner described in Examples 5 and 6 above. These antisera were mixed with the peptides shown in Table 3. These peptides covered residues 522 to 600 of the S protein. The reactive titer of each antiserum was determined. The results are summarized in Table 3

TABLE 3

Reactivity of human or guinea pig anti-RBD2 antisera with synthetic peptides

| Peptide ID No. (SEQ ID NO:) | Synthetic peptides | Reactive Titers Human | Reactive Titers Guinea pig |
|---|---|---|---|
| 76 (SEQ ID NO:126) | CVNFNFNGLTGTGVL | 1/5 | 0/3 |
| 77 (SEQ ID NO:127) | FNGLTGTGVLTPSSK | 1/5 | 0/3 |
| 78 (SEQ ID NO:128) | GTGVLTPSSKRFQPF | 0/5 | 0/3 |
| 79 (SEQ ID NO:129) | TPSSKRFQPFQQFGR | 0/5 | 0/3 |
| 80 (SEQ ID NO:130) | RFQPFQQFGRDVSDF | 0/5 | 0/3 |
| 81 (SEQ ID NO:131) | QQFGRDVSDFTDSVR | 1/5 | 0/3 |
| 82 (SEQ ID NO:132) | DVSDFTDSVRDPKTS | 2/5 | 1/3 |
| 83 (SEQ ID NO:133) | TDSVRDPKTSEILDT | 15 | 1/3 |
| 84 (SEQ ID NO:134) | DPKTSEILDISPCAF | 0/5 | 0/3 |
| 85 (SEQ ID NO:135) | EILDISPCAFGGVSV | 1/5 | 0/3 |
| 86 (SEQ ID NO:136) | SPCAFGGVSVITPGT | 0/5 | 0/3 |
| 87 (SEQ ID NO:137) | GGVSVITPGTNASSE | 0/5 | 0/3 |
| 88 (SEQ ID NO:138) | ITPGTNASSEVAVLY | 5/5 | 3/3 |
| 89 (SEQ ID NO:139) | NASSEVAVLYQDVNC | 5/5 | 3/3 |
| 90 (SEQ ID NO:140) | VAVLYQDVNCTDVST | 4/5 | 1/3 |
| 91 (SEQ ID NO:141) | QDVNCTDVSTAIHAD | 1/5 | 0/3 |
| RBD-55 (SEQ ID NO:26) | | 5/5 | 3/3 |

As shown in Table 3, most of the peptides successfully detected the presence of anti-S protein antibody in the samples.

EXAMPLE 9

Further studies were performed to determine whether the binding of S2-Fc to VERO E6 cells could be neutralized by S protein or its fragments.

Recombinant RBD2 was tested first. $10^4$ of VERO E6 cells were incubated with 330 ng/mL of S2-Fc protein in the presence or absence of know amount of RBD2 protein solution. It was found that 1 μg of RBD2 significantly reduced the S2-Fc binding to VERO E6 cells.

The inhibition assays were repeated with 11 cocktails, each containing nine RBD2 fragment and covering (S28 to S115). More specifically, the VERO E6 cells were harvested and washed twice with a FACS staining/washing buffer. $2\times10^5$ cells were incubated with various peptides and then stained in a final volume of 100 ml with recombinant S-Fc protein (1 mg), S2-Fc protein (0.2-0.3 mg), or hIgG1 as isotype control for 30 minutes at 4° C. Cells were washed twice and stained with the RPE-conjugated anti-hIg Abs for 30 minutes at 4° C. After washing, cells were fixed with fixation buffer for 30 minutes at 4° C., and then the fluorescence was detected with FACS Calibur (Becton Dickinson). The results are summarized in Table 4 below. The inhibition level by RBD2 was designated as 100%.

TABLE 4

Inhibition S2-Fc/VERO E6 cell Binding by S Peptides

| Blocking agents | Percent of Inhibition Concentration of Synthetic peptides (μg/mL) 1 | 10 | 100 |
|---|---|---|---|
| Negative control (SEQ ID NOs:) | 0 | 0 | 0 |
| Gp(28-35) (SEQ ID NOs: 78-85) | 0 | 0 | 0 |
| Gp(36-43) (SEQ ID NOs: 86-93) | 0 | 0 | 0 |
| Gp(44-51) (SEQ ID NOs: 94-101) | 0 | 0 | 0 |
| Gp(52-59) (SEQ ID NOs: 102-109) | 0 | 0 | 0 |
| Gp(60-67) (SEQ ID NOs: 110-117) | 0 | 0 | 0 |
| Gp(68-75) (SEQ ID NQs: 118-125) | 0 | 0 | 0 |
| Gp(76-83) (SEQ ID NOs: 126-133) | 0 | 0 | 0 |
| Gp(84-91) (SEQ ID NOs: 134-141) | 0 | 10% | 30% |
| Gp(92-99) (SEQ ID NOs: 142-149) | 0 | 0 | 0 |
| Gp(100-107) (SEQ ID NOs: 150-157) | 0 | 0 | 0 |
| Gp(108-115) (SEQ ID NOs: 158-165) | 0 | 0 | 0 |
| RRBD2 (SEQ ID NO: 24) | 100% | 100% | NA |

As shown in Table 4, the peptide cocktail containing S peptides 84 to 91 (group #8) strongly inhibited the binding between S2-Fc and VERO-6 cells by 30% as compared with those in the RBD2. These results indicate that the major B-cell epitopes of S2 were located within the region covering these 9 peptides, i.e., residues 540 to 600 of S protein.

To more clearly define the protective epitope(s) of the S2 fragment, individual peptides S84-91 were also tested. $10^4$ of VERO E6 cells were incubated with 330 ng per mL of S2-Fc protein in the presence or absence of the peptides, respectively. The inhibitions of the binding of S-Fc to VERO E6 cells were determined in the same manner described above. The same experiment was repeated using a polypeptide containing with 50 amino acids covering S84 to S91 ("RBD-55" shown in Table 2 above). The results are summarized in Table 5 below.

TABLE 5

Inhibition Activity of S Synthetic Peptides against S2-Fc/VERO E6 cell Binding

| Blocking agents | Percent of Inhibition Concentration of Synthetic peptides (μg/mL) 1 | 10 | 100 |
|---|---|---|---|
| Negative control (SEQ ID NOs:) | 0 | 0 | 0 |
| Gp(76-83) (SEQ ID NOs: 126-133) | 0 | 0 | 0 |
| Gp(84-91) (SEQ ID NO: 134-141) | 0 | 10 | 30 |
| S84 (SEQ ID NO: 134) | 0 | 0 | 0 |

TABLE 5-continued

Inhibition Activity of S Synthetic Peptides against S2-Fc/VERO E6 cell Binding

| Blocking agents | Percent of Inhibition Concentration of Synthetic peptides (μg/mL) 1 | 10 | 100 |
|---|---|---|---|
| S85 (SEQ ID NO: 135) | 0 | 0 | 0 |
| S86 (SEQ ID NO: 136) | 0 | 0 | 10 |
| S87 (SEQ ID NO: 137) | 0 | 0 | 0 |
| S88 (SEQ ID NO: 138) | 0 | 0 | 0 |
| S89 (SEQ ID NO: 139) | 0 | 0 | 10 |
| S90 (SEQ ID NO: 140) | 0 | 0 | 0 |
| S91 (SEQ ID NO: 141) | 0 | 0 | 0 |
| S86 + S87 (SEQ ID NOs: 136 and 137) | 0 | 20 | 40 |
| S86 + S88 (SEQ ID NOs: 136 and 138) | 0 | 0 | 0 |
| S86 + S89 (SEQ ID NOs: 136 and 139) | 0 | 20 | 40 |
| S86 + S90 (SEQ ID NOs: 136 and 140) | 0 | 0 | 0 |
| S86 + S91 (SEQ ID NOs: 136 and 141) | 0 | 0 | 0 |
| RBD-55 (SEQ ID NO: 26) | 10 | 30 | 60 |
| rRBD2 (SEQ ID NOs: 24) | 100 | 100 | Not test |

As shown in Table 5, both S86 and S89 statistically significantly inhibited the S2-Fc/VERO cell binding. Furthermore, S86 and S87, or S86 and S89 exhibited synergetic effect and could inhibit 30% of S2-Fc/Vero cell binding. Each of S86 and S89 contains two cysteine residues on both termini, which could form a disulfide bridge and might lead to strong inhibition. RBD-55 inhibited the S2-FCNERO E6 cell binding more significantly than S86 or S89 peptide (60% inhibition vs 10% inhibition). These results indicate that RBD-55 could be used as an immunogen to induce protective antibodies against SARS CoV.

EXAMPLE 10

The above-described peptides were used to generate S peptide-specific antisera. Guinea pigs and rabbits were immunized with peptides cocktail (50 to 200 μg) emulsified with the Freund's complete adjuvant and injected intramuscularly. The animals were boosted with the same amount of peptide cocktails in the incomplete Freund's adjuvant at days 14 and 28. Antisera were collected on day 42 and tested by ELISAs and immunoblotting. Both rabbit and guinea pig antisera were shown to be monospecific for their respective immunizing peptides by the peptide-specific ELISAs. In addition, both guinea pig and rabbit antisera raised against S peptides reacted with SARS CoV on immunoblot analyses. Since most S peptides induced strong anti-peptide antibody responses in at least one animal species, they are appropriate immunogens to be included in immunogenic compositions, e.g., vaccines.

EXAMPLE 11

Infant ferrets were used to examine the protective activity of S-specific antisera against SARS CoV challenge as described by NIH (Yang et al., Nature (2004) 428:561-564.). Five-day old infant ferrates were inoculated subcutaneously (SC) on the dorsum with 0.15 mL of two different rabbit anti-S fragments. Pre-immune sera were used as negative controls. One day after this passive immunization, the infant ferrets were injected intraperitoneally (IP) with 4000 plaqueforming units (cfu) of SARS CoV Tor2 strain (0.1 ml) freshly grown and isolated from a Vero cell culture medium supplemented with cofactors and diluted in PBS containing 0.5 mM $MgCl_2$ and 0.15 mM $CaCl_2$. One day later, blood samples were collected via cardiac puncture under methoxyflurane anaesthesia and cultured in the Vero cell media. The number of virus per mL of blood was determined after 24 hours. The Student's t-test was used to analyze differences observed in the levels of viramia relative to controls. The results indicate that the antibodies protect against SARS CoV challenge The protective ability of anti-RBD1 sera against SARS CoV infection was examined in the ferret model. It was that ferret passively immunized with guinea pig anti-RBD1 antisera were not more protective than pre-bleed serum control.

EXAMPLE 12

Little is known about the cellular immune response to SARS CoV and its role in protecting against SARS CoV infection. To examine the cellular response elicited by SARS CoV, T-cell lines' proliferative responses to S peptides were determined by conventional cytokine assays as described below.

S-specific T-cell lines were generated. BALB/c (H-$2_d$) mice (Charles River Animal Farm, Montreal, Canada) were primed subcutaneously with 20 μg of recombinant S adsorbed to 1.5 mg of aluminium phosphate (alum) in presence of 100 μg of CpG. The mice were boosted twice with the same dose of immunogen at 3-week intervals.

Ten days after the final boost, the spleen of each immunized mouse was removed. Splenocytes were isolated and cultured in 200 μL of RPMI 1640 medium (Flow Lab) at $5.75\times10^5$ cells per well of a microtiter plate. The medium was supplemented with 10% heat-inactivated fetal calf serum (Gibson), 2 mM L-glutamine, 100 U/mL) penicillin, and $5\times0.10^{-5}$ M 2-mercaptoethanol and contained varying concentrations (1, 10 and 100 μg per mL) of individual S peptides. The cultures were kept in a humidified incubator in the presence of 5% $CO_2$/air. Triplicate cultures were performed for each concentration of each peptide. Five days later, 150 μL of 10% rat concanavalin A culture supernatant diluted in the culture medium was added to the microtiter plate wells. The supernatant contained Interleukin-2 (IL-2), which expand peptide-specific T-cells.

Six days later, 150 μL of the supernatant were removed from each microculture, and 150 μL of a fresh IL-2 containing culture supernatant added to further expand and maintain the viability of the peptide-specific T-cells. After another 6 day-incubation, the cells were washed with 200 μL culture medium for three times. Each set of cultures were then stimulated with a peptide at concentrations of 1, 10, and 100 μg/mL, respectively in the presence of $2\times0.10^5$ irradiated (1,500 rad) BALB/c spleen cells in a final volume of 200 μL culture medium. Sixty microliters of the supernatant were then removed from each triplicate culture and pooled. All supernatants were then assayed for IL-2, IL-4, and Interferon-gamma (IFN-gamma) using murine IL-2 and IL-4 ELISA kits (Endogen Inc, MA, U.S.A.) and a mouse IFN-gamma ELISA kit (Genzyme Corporation. MA, U.S.A.). Test culture supernatants were assayed at 1 in 5 dilution according to the manufacturers' instructions.

The results indicated that peptides corresponding to residues 120-134, 649-688, and 699-713 elicited proliferative responses and the release of specific cytokines. Because of this strong ability to induce cellular immune response, these immunodominant T-cell epitopes can be used as carriers for pneumococcal polysaccharides and/or S B-cell epitopes to enhance the immunogenicity. The Th1 cell epitopes identified above can be used in SARS CoV vaccine formulations to induce SARS-specific cellular immune responses.

EXAMPLE 13

In this example, murine anti-S monoclonal antibodies were generated. BALB/c mice were immunized intraperitoneally with 20 to 50 μg of RBD2 emulsified in the Freund's complete adjuvant. Two weeks later, the mice were injected with the same amount of immunogen in the incomplete Freund's adjuvant. The anti-S titers were examined. Positive mice were selected for making hybridomas by standard cell fusion techniques. Three days before the fusion, the mice were boosted again with the same amount of immunogen in the incomplete Freund's adjuvant. Hybridomas were produced by fusion of splenic lymphocytes from immunized mice with non-secreting Sp2/0 myeloma cells in the manner described in Hamel et al. 1987, J. Med. Microbiol. 23:163-170. S-specific hybridomas were cloned by sequential limiting dilutions and screened for anti-S monoclonal antibody production. Eight S-specific hybridoma cell lines were identified, expanded, and frozen in liquid nitrogen by standard techniques.

EXAMPLE 14

The mechanism of SARS CoV infection is unclear although it was reported that infection took place through enteric route, respiratory tract, and skin. As discussed above, S1-Fc and S2-Fc, but not S3-Fc, bind to VERO cells. To test whether S3-Fc binds to any other cells, a panel of cell lines were tested. About $1\times10^4$ cells/mL were incubated with 0.1, 0.3, and 1 μg of S3-Fc or the same amount of S1-Fc or S2-Fc in a volume of 1 mL for 2 hours at room temperature. The cells were washed in PBS with 0.5% BSA and 0.1% NaN3, incubated with FITC-labeled goat anti-human IgG Fc (Sigma), and analyzed by flow cytometry.

It was unexpected that S3-Fc bound strongly to NIH 3T3 cells but not to Jarket cells. S3-Fc showed strong binding to NIH 3T3 cells even at a concentration as low as 0.1 μg/mL. In contrast, S1-Fc did not bind to NIH3T3 cells even at 10 μg/mL, and S2-Fc showed some binding to NIH 3T3 cell at 1 μg/mL. These results indicate that S3-Fc had specificity toward receptors in NIH 3T3 cells.

It was also unexpected that S protein also binds to HeLa, BHK-21, and COS-7 cells. Three separated receptor-binding domains of S protein were identified: (1) the low affinity mapped to the N-terminal 333 residues, (2) a intermediate affinity receptor-binding domain (with 1 μM avidity) mapped to residues 334 to 666, and (3) a high affinity domain within residues 667 to 999. Beside VERO E6 cells, all these cell lines had not been reported before to be the hosts for SARS CoV replication. This explained why SARS CoV could infect patient via skin contact with infected solutions.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. An isolated polypeptide consisting of the sequence selected from the group consisting of SEQ ID NO: 24, 26, 28 and 85-95.

2. The polypeptide of claim 1, wherein the sequence is SEQ ID NO: 24 or 26.

3. An isolated glycoprotein consisting of the polypeptide of claim 1 and a polysaccharide.

4. The glycoprotein of claim 3, wherein the polysaccharide is from *S. pneumococcal*.

5. A fusion protein comprising a SARS CoV spike protein fragment and a heterologous polypeptide wherein the spike protein fragment consists of a polypeptide of claim 1.

6. The fusion protein of claim 5, wherein the heterologous polypeptide contains an Fc portion of an immunoglobin.

7. The fusion protein of claim 6, wherein the immunoglobin is IgG.

8. The fusion protein of claim 7, wherein the immunoglobin is IgG1.

9. The fusion protein of claim 8, wherein the immunoglobin is human IgG1.

10. The fusion protein of claim 5, wherein the heterologous polypeptide contains a surface portion of a protein of a pathogen.

11. The fusion protein of claim 10, wherein the surface portion of a protein contains hemaglutinin or neuramidase of an influenza virus.

12. A composition comprising the polypeptide of claim 1 and a pharmaceutically acceptable carrier.

13. A composition comprising the fusion protein of claim 5 and a pharmaceutically acceptable carrier.

* * * * *